US007820787B2

(12) United States Patent
Meares et al.

(10) Patent No.: US 7,820,787 B2

(45) **Date of Patent: *Oct. 26, 2010**

(54) MULTI-FUNCTIONAL ANTIBODIES

(75) Inventors: Claude F. Meares, Davis, CA (US); Todd M. Corneillie, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/625,047

(22) Filed: Jul. 22, 2003

(65) Prior Publication Data

US 2004/0198962 A1 Oct. 7, 2004

Related U.S. Application Data

(63) Continuation-in-part of application No. 10/350,555, filed on Jan. 23, 2003, now Pat. No. 7,528,235.

(51) Int. Cl.
*A61K 39/395* (2006.01)

(52) U.S. Cl. ................ 530/350; 424/155.1; 424/175.1; 424/178.1

(58) Field of Classification Search ................ 424/1.11, 424/1.49, 1.53, 1.465, 4.69, 155.1, 175.1, 424/178.1, 1.59; 530/388.8
See application file for complete search history.

(56) References Cited

U.S. PATENT DOCUMENTS

| | | | | |
|---|---|---|---|---|
| 4,678,667 | A | 7/1987 | Meares et al. | |
| 4,722,892 | A | 2/1988 | Meares et al. | |
| 5,541,287 | A | 7/1996 | Yau et al. | |
| 5,747,654 | A | 5/1998 | Pastan et al. | |
| 5,789,554 | A | 8/1998 | Leung et al. | |
| 5,837,242 | A | 11/1998 | Holliger et al. | |
| 2002/0006379 | A1 * | 1/2002 | Hansen et al. | 424/1.49 |
| 2003/0124057 | A1 * | 7/2003 | Griffiths et al. | 424/1.49 |

FOREIGN PATENT DOCUMENTS

| | | | |
|---|---|---|---|
| WO | WO 95/15979 A2 | | 6/1995 |
| WO | WO 9966951 A2 | * | 12/1999 |
| WO | WO 00/74729 A2 | | 12/2000 |

OTHER PUBLICATIONS

Sharkey et al. (2002 ASCO Annual Meeting abstract, Orlando, Fl., May 18, 2002).*
Sigma-Aldrich catalog print, DOTA.*
Lovqvist et al. (J. Nucl. Med. 1998; 39: 1776-1777).*
Goodwin et al. (Cancer 1997; 80: 2675-2680).*
Goldberg et al. (Cancer Immunol. Immunother. 2003; 52: 281-296).*
Zhu et al (J. Nucl. Med. 1998; 39: 65-76).*
Paul, Fundamental Immunology, (textbook), 1993, pp. 292-295.*
Rudikoff et al. (Proc. Natl Acad. Sci. USA 1982; 79: 1979).*
Chmura et al. (PNAS 2001; 98: 8480-8484).*
Goodwin, David A. et al.; "Pharmacokinetics of pretargeted monoclonal antibody 2D12.5 and $^{88}$Y-Janus-2-(*p*-nitrobenzyl)-1,4,7,10-tetraazacyclododecanetetraacetic acid (DOTA) in BALB/c mice with KHJJ mouse adenocarcinoma: A model for $^{90}$Y radioimmunotherapy", *Cancer Research*; Nov. 15, 1994; pp. 5937-5946; vol. 54.
Karacay, H. et al.; "Pretargeting for cancer radioimmunotherapy with bispecific antibodies: Role of the bispecific antibody's valency for the tumor target antigen"; *Bioconjugate Chem.*: 2002; pp. 1054-1070; vol. 13; USA.
Lubic, Stephen P. et al.; "Biodistribution and dosimetry of pretargeted monoclonal antibody 2D12.5 and Y-Janus-DOTA in BALB/c mice with KHJJ mouse adenocarcinoma"; *The Journal of Nuclear Medicine*; Apr. 2001; pp. 670-678; vol. 42., No. 4.
Stickney, Dwight R. et al.; "Bifunctional antibody: A binary radiopharmaceutical delivery system for imaging colorectal carcinoma"; *Cancer Research*; Dec. 15, 1991; pp. 6650-6655; vol. 51.
Waldherr, Christian et al.; "Tumor response and clinical benefit in neuroendocrine tumors after 7.4 GBq 90Y-DOTATOC"; *The Journal of Nuclear Medicine*; May 2002; pp. 610-616; vol. 43, No. 5.
M. Chinol, et al., "Biodistrubution in tumour-bearing mice of two $^{90}$Y-labeled biotins using three-step tumour targeting," *Nuclear Medicine Comm.*, 18:176-182, (1997).
David A. Goodwin, et al., "Pre-targeted immunoscintigraphy: murine tumors with indium-111-labeled bifunctional haptens," *J. Nucl. Med.*, 29:226-234, (1998).
David A. Goodwin, et al, "Pretargeted Immunoscintigraphy: Effect of hapten valency on murine tumor uptake,", *J. Nucl. Med.*, 33:2006-20013, (1992).
D.J. Hnatowich, et al., "Investigation of avidin and biotin for imaging applications," *J. Nucl. Med.*, 28:1294-1302, (1987).
H.P. Kalofonos, et al. "Imaging of tumors in patients with indium-111-labeled biotin and streptavidin-conjugated antibodies: Preliminary communication," *J. Nucl. Med.*, 31:1979-1976, (1990).
Alexander L. Klibanov, et al., "Blood clearance of radiolabeled antibodies: Enhancement by lactosamination and treatment with biotin-avidin or anti-mouse IgG antibodies," *J. Nucl. Med.*, 29:1951-1956, (1988).
J. Ian Marsh, et al., "Streptavidin and biotin as potential tumor imaging agents,"*J. Nucl. Med.*, 29(05):728-729, (1988).
Damon L. Meyer, et al., "Kinectics of the dissociation of Indium-(*p*-substituted-benzyl)ethylenediaminetetraacetic acid hapten analogues from the monoclonal anti-hapten antibody CHA255," *Bioconiugate Chem.*, 1:279-284. (1990).
Orlandi et al., *Proc. Natl. Acad. Sci.*, USA 86:3833-3837. (1989).
Jeffrey T. Owens, et al. "Mapping the promoter DNA sites proximal to conserved regions of $a^{70}$ in an *escherichia coli* RNA polymerase-*lac*UV5 open promoter complex," *Biochemistry*, 37:7670-7675, (1998).
Jeffrey T. Owens, et al. "Mapping the $a^{70}$ subunit contact sites on *escherichia coli* RNA polymerase with a $a^{70}$ conjugated chemical protease," *Proc. Natl. Acad. Sci. USA*, 95:6021-6026, (1998).

(Continued)

*Primary Examiner*—Brandon J Fetterolf
(74) *Attorney, Agent, or Firm*—Morgan, Lewis & Bockius LLP; Jeffry S. Mann

(57) ABSTRACT

The present invention provides antibodies comprising an antigen recognition domain that specifically binds to a metal chelate: mutant antibodies comprising a reactive site not present in the wild-type of the antibody, wherein the reactive site is in a position proximate to or within the antigen recognition domain; and methods of using such antibodies to diagnose and treat disease.

19 Claims, 41 Drawing Sheets

OTHER PUBLICATIONS

G. Paganelli, et al., "Three-step monoclonal antibody tumor targeting in carcinoembyonic antigen-positive patients," *Cancer Research*, 51:5980-5966, (1991).

G. Paganelli, et al., "Monoclonal antibody pretargeting techniques for tumor localization: the avidin-biotin system," *Nuclear Medicine Comm.*, 12:211-234, (1991).

Paul et al., *Fundamental Immunology Raven Press. NY*, Chapter 8: 242, (1993).

Dayton T. Reardan, et al., "Antibodies against metal chelates," *Nature*, 316:265-268, (1985).

Bruno Robert, et al., "Cytokine targeting in tumors using a bispecific antibody directed against carinoembryonic antigen and tumor necrosis factor $a^1$," *Cancer Research*, 56:4758-4765, (1996).

Eric Rouvier, et al., "Targeting medullary thyroid carcinomas with bispecific antibodies and bivalent haptens " *Horm, Res.*, 47:163-167. (1997).

Rudikoff, et al. *Proc. Natl. Sci. USA*, 79:1979-1983, (1982).

B. Schechter, et al., "Indirect immunotargeting of CIS-PT to human epidermiod carcinoma KB using the avidin-biotin system," *Int, J. Cancer*, 48:167-172, (1991).

Vladimir V. Sinitsyn, et al., "Rapid blood clearance of biotinylated IgG after Infusion of avidin," *J. Nucl. Med.*, 30:66-69, (1989).

Fan Yuna, et al., "Pharmacokinetic analysis of two step approaches using bifunctional and enzyme-conjugated antibodies," *Cancer Research*, 51:3119-3130, (1991).

* cited by examiner sequence_AA_2D12.5_variable domains.txt

>2D12.5VL_MOUSE
(1) QAVVTQESALTTSPGETVTLTCRSSTGAVTTSNYANWVQEKPDHLFTGLIGGNNNRPPGVPARFSGSLIGDKAALTIAGTQTED
EAIYFCALWYSNHWVFGGGTRLTVLG (2) CDR1 - RSSTGAVTTSNYAN
(3) CDR2 - GNNNRPP
(4) CDR3 - ALWYSNHWV

>2D12.5VH_MOUSE
(5) QVKLQESGPGLVQPSQSLSITCTVSGFSLTDYGVHWVRQSPGKGLEWLGVIWSGGGTAYTAAFISRLNIY
KDNSKNQVFFEMNSLQANDTAMYYCARRGSYPYNYFDVWGQGTTVTVSS (6) CDR1 - DYGVH
(7) CDR2 - VIWSGGGTAYTAAFIS
(8) CDR3 - RGSYPYNYFDV

FIG. 1

Translation of 2D12.5 VH variable genes

```
                                           10        20        30        40        50
                                   ....|....|....|....|....|....|....|....|....|....|
(9)2d12.5 VH native hybridoma    1 VKLQESGPGLVQPSQSLSITCTVSGFSLTDYGVHWVRQSPGKGLEWLGVI 50
(10)2d12.5 VH native cloned      1 .................................................. 50
(11)2d12.5 VH N87D_cloned        1 .................................................. 50
(12)2d12.5 VH N87D_G53C_cloned   1 .................................................. 50
(13)2d12.5 VH_N87D_G54C_cloned   1 .................................................. 50
(14)2d12.5 VH N87D_G55C_cloned   1 .................................................. 50

                                           60        70        80        90       100
                                   ....|....|....|....|....|....|....|....|....|....|
2d12.5 VH native hybridoma       51 WSGGGTAYTAAFISRLNIYKDNSKNQVFFEMNSLQANDTAMYYCARRGSY 100
2d12.5 VH native cloned         51 .................................................. 100
2d12.5 VH N87D_cloned           51 ....................................D............. 100
2d12.5 VH N87D_G53C_cloned      51 ..C.................................D............. 100
2d12.5 VH_N87D_G54C_cloned      51 ...C................................D............. 100
2d12.5 VH N87D_G55C_cloned      51 ....C...............................D............. 100

                                          110
                                   ....|....|....|...
2d12.5 VH native hybridoma      101 PYNYFDVWGQGTTVTVSS 118
2d12.5 VH native cloned        101 .................A 118
2d12.5 VH N87D_cloned          101 .................A 118
2d12.5 VH N87D_G53C_cloned     101 .................A 118
2d12.5 VH_N87D_G54C_cloned     101 .................A 118
2d12.5 VH N87D_G55C_cloned     101 .................A 118
```

FIG. 2

2D12.5 VH variable genes

```
                                      10        20        30        40        50
                                  ....|....|....|....|....|....|....|....|....|....|
(15) 2d12.5 VH native hybridoma 1 GTGAAGCTGCAGGAGTCAGGACCTGGCCTAGTGCAGCCCTCACAGAGCCT 50
(16) 2d12.5 VH native cloned    1 .................T................................ 50
(17) 2d12.5 VH N87D_cloned      1 .................T................................ 50
(18) 2d12.5 VH N87D_G53C_cloned 1 .................T................................ 50
(19) 2d12.5 VH_N87D_G54C_cloned 1 .................T..G............................. 50
(20) 2d12.5 VH N87D_G55C_cloned 1 .................T................................ 50

                                       60        70        80        90       100
                                   ....|....|....|....|....|....|....|....|....|....|
2d12.5 VH native hybridoma 51 GTCCATCACCTGCACGGTCTCTGGTTTCTCATTAACTGACTATGGTGTAC 100
2d12.5 VH native cloned    51 .................................................. 100
2d12.5 VH N87D_cloned      51 .................................................. 100
2d12.5 VH N87D_G53C_cloned 51 .................................................. 100
2d12.5 VH_N87D_G54C_cloned 51 .................................................. 100
2d12.5 VH N87D_G55C_cloned 51 .................................................. 100

                                       110       120       130       140       150
                                    ....|....|....|....|....|....|....|....|....|....|
2d12.5 VH native hybridoma 101 ACTGGGTTCGCCAGTCTCCAGGAAAGGGTCTGGAATGGCTGGGAGTGATA 150
2d12.5 VH native cloned    101 .................................................. 150
2d12.5 VH N87D_cloned      101 .................................................. 150
2d12.5 VH N87D_G53C_cloned 101 .................................................. 150
2d12.5 VH_N87D_G54C_cloned 101 .................................................. 150
2d12.5 VH N87D_G55C_cloned 101 .................................................. 150
```

FIG. 3A

```
                                    160       170       180       190       200
                                ....|....|....|....|....|....|....|....|....|....|
2d12.5 VH native hybridoma  151 TGGAGTGGTGGAGGCACGGCCTATACTGCGGCGTTCATATCCAGACTGAA 200
2d12.5 VH native cloned     151 .................................................. 200
2d12.5 VH N87D_cloned       151 .................................................. 200
2d12.5 VH N87D_G53C_cloned  151 ......T........................................... 200
2d12.5 VH_N87D_G54C_cloned  151 .........T.T...................................... 200
2d12.5 VH_N87D_G55C_cloned  151 ............T..................................... 200

                                    210       220       230       240       250
                                ....|....|....|....|....|....|....|....|....|....|
2d12.5 VH native hybridoma  201 CATCTACAAGGACAATTCCAAGAACCAAGTTTTCTTTGAAATGAACAGTC 250
2d12.5 VH native cloned     201 .................................................. 250
2d12.5 VH N87D_cloned       201 .................................................. 250
2d12.5 VH N87D_G53C_cloned  201 .................................................. 250
2d12.5 VH_N87D_G54C_cloned  201 .................................................. 250
2d12.5 VH_N87D_G55C_cloned  201 .................................................. 250

                                    260       270       280       290       300
                                ....|....|....|....|....|....|....|....|....|....|
2d12.5 VH native hybridoma  251 TGCAAGCTAATGACACAGCCATGTATTACTGTGCCAGAAGGGGTAGCTAC 300
2d12.5 VH native cloned     251 .................................................. 300
2d12.5 VH N87D_cloned       251 ........G......................................... 300
2d12.5 VH N87D_G53C_cloned  251 ........G......................................... 300
2d12.5 VH_N87D_G54C_cloned  251 ........G......................................... 300
2d12.5 VH_N87D_G55C_cloned  251 ........G......................................... 300
```

FIG. 3A (CONT.)

```
                    310        320        330        340        350
                    |....|....|....|....|....|....|....|....|....|....|
2d12.5 VH native hybridoma  301 CCTTACAACTACTTCGATGTCTGGGGCCAAGGGACCACAGTCACCGTCTC 350
2d12.5 VH native cloned     301 ................................G................ 350
2d12.5 VH N87D_cloned       301 ................................G................ 350
2d12.5 VH N87D_G53C_cloned  301 ................................G................ 350
2d12.5 VH N87D_G54C_cloned  301 ................................G................ 350
2d12.5 VH N87D_G55C_cloned  301 ................................G................ 350
```

FIG. 3A (CONT.)

2d12.5 VH variable genes

```
2d12.5 VH native hybridoma   351 CTCA 354
2d12.5 VH native cloned      351 .G.. 354
2d12.5 VH N87D_cloned        351 .G.. 354
2d12.5 VH N87D_G53C_cloned   351 .G.. 354
2d12.5 VH N87D_G54C_cloned   351 .G.. 354
2d12.5 VH N87D_G55C_cloned   351 .G.. 354
```

FIG. 3B

Translation of 2D12.5 VL genes

```
                                          10        20        30        40        50
                                     ....|....|....|....|....|....|....|....|....|....|
(21)2d12.5 VL native hybridoma   1   AVVTQESALTTSPGETVTLTCRSSTGAVTTSNYANWVQEKPDHLFTGLIG 50
(22)2d12.5 VL_native cloned      1   .................................................. 50
(23)2d12.5 VL N53C_cloned        1   .................................................. 50

                                          60        70        80        90       100
                                     ....|....|....|....|....|....|....|....|....|....|
    2d12.5 VL native hybridoma  51   GNNNRPPGVPARFSGSLIGDKAALTIAGTQTEDEAIYFCALWYSNHWVFG100
    2d12.5 VL_native cloned     51   ..................................................100
    2d12.5 VL N53C_cloned       51   .C................................................100

                                     ....|....
    2d12.5 VL native hybridoma 101   GGTRLTVLG109
    2d12.5 VL_native cloned    101   ...K....S109
    2d12.5 VL N53C_cloned      101   ...K....S109
```

FIG. 4

```
2D12.5 VL variable genes
                                              10        20        30        40        50
                                      ....|....|....|....|....|....|....|....|....|....|
(24) 2d12.5 VL native hybridoma   1   GCTGTTGTGACTCAGGAATCTGCACTCACCACATCACCTGGTGAAACAGT 50
(25) 2d12.5 VL_native cloned      1   .................................................. 50
(26) 2d12.5 VL_N53C_cloned        1   .................................................. 50

                                              60        70        80        90       100
                                      ....|....|....|....|....|....|....|....|....|....|
     2d12.5 VL native hybridoma  51   CACACTCACTTGTCGCTCAAGTACTGGGGCTGTTACGACTAGTAACTATG 100
     2d12.5 VL_native cloned     51   .................................................. 100
     2d12.5 VL_N53C_cloned       51   .................................................. 100

                                             110       120       130       140       150
                                      ....|....|....|....|....|....|....|....|....|....|
     2d12.5 VL native hybridoma 101   CCAACTGGGTCCAAGAGAAACCAGATCATTTATTCACTGGTCTAATAGGT 150
     2d12.5 VL_native cloned    101   .................................................. 150
     2d12.5 VL_N53C_cloned      101   .................................................. 150

                                             160       170       180       190       200
                                      ....|....|....|....|....|....|....|....|....|....|
     2d12.5 VL native hybridoma 151   GGTAATAATAACCGACCTCCAGGTGTTCCTGCCAGATTCTCAGGCTCCCT 200
     2d12.5 VL_native cloned    151   .................................................. 200
     2d12.5 VL_N53C_cloned      151   ...TG............................................. 200
```

FIG. 5

```
                                    210       220       230       240       250
                               ....|....|....|....|....|....|....|....|....|....|
2d12.5 VL native hybridoma  201 GATTGGAGACAAGGCTGCCCTCACCATCGCAGGGACACAGACTGAGGATG250
2d12.5 VL_native cloned     201 ..................................................250
2d12.5 VL_N53C_cloned       201 ..................................................250

                                    260       270       280       290       300
                               ....|....|....|....|....|....|....|....|....|....|
2d12.5 VL native hybridoma  251 AGGCAATATATTTCTGTGCTCTATGGTACAGCAACCATTGGGTGTTCGGT300
2d12.5 VL_native cloned     251 ..................................................300
2d12.5 VL_N53C_cloned       251 ..................................................300

                                    310       320
                               ....|....|....|....|....|..
2d12.5 VL native hybridoma  301 GGAGGAACCAGACTGACTGTCCTAGGC327
2d12.5 VL_native cloned     301 ..G.......A.............A..327
2d12.5 VL_N53C_cloned       301 ..G.......A.............A..327
```

FIG. 5 (CONT.)

```
Translation of Mouse 2D12.5 VL - Human TetTox CL kappa (light chain gene)

                                          10        20        30        40        50
                                 ....|....|....|....|....|....|....|....|....|....|
(27) 2dVL-TTCL native_cloned      1   RSAVVTQESALTTSPGETVTLTCRSSTGAVTTSNYANWVQEKPDHLFTGL 50
(28) 2dVL-TTCL N53C_cloned        1   .................................................. 50
(29) 2d12.5 VL native hybridoma   1   --................................................ 50
(30) TTCL template for gene assembl 1 --------------------------------------------------

                                          60        70        80        90       100
                                 ....|....|....|....|....|....|....|....|....|....|
     2dVL-TTCL native_cloned      51  IGGNNNRPPGVPARFSGSLIGDKAALTIAGTQTEDEAIYFCALWYSNHWV 100
     2dVL-TTCL N53C_cloned        51  ...C.............................................. 100
     2d12.5 VL native hybridoma   49  .................................................. 98
     TTCL template for gene assembl 1 --------------------------------------------------

                                         110       120       130       140       150
                                 ....|....|....|....|....|....|....|....|....|....|
     2dVL-TTCL native_cloned      101 FGGGTKLTVLSRTVAAPSVFIFPPSDEQLKSGTASVVCLLNNFYPREAKV 150
     2dVL-TTCL N53C_cloned        101 .................................................. 150
     2d12.5 VL native hybridoma   99  .....R....G                                        100
     TTCL template for gene assembl 1 -----------....................................... 80
```

FIG. 6

```
                                        160       170       180       190       200
                                    ....|....|....|....|....|....|....|....|....|....|
2dVL-TTCL native_cloned         151 QWKVDNALQSGNSQESVTEQDSKDSTYSLSSTLTLSKADYEKHKVYACEV200
2dVL-TTCL N53C_cloned           151 ..................................................200
2d12.5 VL native hybridoma
TTCL template for gene assembl  40  ..................................................80

                                        210       220
                                    ....|....|....|....|.
2dVL-TTCL native_cloned         201 THQGLSLPVTKSFNRGEC*F*221
2dVL-TTCL N53C_cloned           201 ..................*.*221
2d12.5 VL native hybridoma
TTCL template for gene assembl  90  ..................   107
```

FIG. 6 (CONT.)

Mouse 2D12.5 VL - Human TetTox CL kappa (light chain gene)

FIG. 7A

```
                                                10        20        30        40        50
                                       ....|....|....|....|....|....|....|....|....|....|
(31)2dVL-TTCL native_cloned        1   AGATCTGCTGTTGTGACTCAGGAATCTGCACTCACCACATCACCTGGTGA 50
(32)2dVL-TTCL N53C_cloned          1   .................................................. 50
(33)2d12.5 VL native hybridoma     1   ------............................................ 44
(34)TTCL template for gene assem   1   -------------------------------------------------- 1

                                                60        70        80        90       100
                                       ....|....|....|....|....|....|....|....|....|....|
    2dVL-TTCL native_cloned       51   AACAGTCACACTCACTTGTCGCTCAAGTACTGGGGCTGTTACGACTAGTA 100
    2dVL-TTCL N53C_cloned         51   .................................................. 100
    2d12.5 VL native hybridoma    45   .................................................. 94
    TTCL template for gene assem   1   -------------------------------------------------- 1

                                               110       120       130       140       150
                                       ....|....|....|....|....|....|....|....|....|....|
    2dVL-TTCL native_cloned      101   ACTATGCCAACTGGGTCCAAGAGAAACCAGATCATTTATTCACTGGTCTA 150
    2dVL-TTCL N53C_cloned        101   .................................................. 150
    2d12.5 VL native hybridoma    95   .................................................. 144
    TTCL template for gene assem   1   -------------------------------------------------- 1

                                               160       170       180       190       200
                                       ....|....|....|....|....|....|....|....|....|....|
    2dVL-TTCL native_cloned      151   ATAGGTGGTAATAATAACCGACCTCCAGGTGTTCCTGCCAGATTCTCAGG 200
    2dVL-TTCL N53C_cloned        151   .........TG....................................... 200
    2d12.5 VL native hybridoma   145   .................................................. 194
    TTCL template for gene assem   1   -------------------------------------------------- 1
```

```
                                       210       220       230       240       250
                                   ....|....|....|....|....|....|....|....|....|....|
2dVL-TTCL native_cloned        201 CTCCCTGATTGGAGACAAGGCTGCCCTCACCATCGCAGGGACACAGACTG 250
2dVL-TTCL N53C_cloned          201 .................................................. 250
2d12.5 VL native hybridoma     195 .................................................. 244
TTCL template for gene assem   1   -------------------------------------------------- 1

                                       260       270       280       290       300
                                   ....|....|....|....|....|....|....|....|....|....|
2dVL-TTCL native_cloned        251 AGGATGAGGCAATATATTTCTGTGCTCTATGGTACAGCAACCATTGGGTG 300
2dVL-TTCL N53C_cloned          251 .................................................. 300
2d12.5 VL native hybridoma     245 .................................................. 294
TTCL template for gene assem   1   -------------------------------------------------- 1

                                       310       320       330       340       350
                                   ....|....|....|....|....|....|....|....|....|....|
2dVL-TTCL native_cloned        301 TTCGGTGGGGAACCAAACTGACTGTCCTAAGCCGAACTGTGGCTGCACC 350
2dVL-TTCL N53C_cloned          301 .................................................. 350
2d12.5 VL native hybridoma     295 ........A.......G.............G..                 327
TTCL template for gene assem   1   ---------------------------------................. 17

                                       360       370       380       390       400
                                   ....|....|....|....|....|....|....|....|....|....|
2dVL-TTCL native_cloned        351 ATCTGTCTTCATCTTCCCGCCATCTGATGAGCAGTTGAAATCTGGAACTG 400
2dVL-TTCL N53C_cloned          351 .................................................. 400
2d12.5 VL native hybridoma
TTCL template for gene assem   18  .................................................. 67
```

FIG. 7A (CONT.)

```
                                       410       420       430       440       450
                                ....|....|....|....|....|....|....|....|....|....|
2dVL-TTCL native_cloned     401 CCTCTGTTGTGTGCCTGCTGAATAACTTCTATCCCAGAGAGGCCAAAGTA 450
2dVL-TTCL N53C_cloned       401 .................................................. 450
2d12.5 VL native hybridoma
TTCL template for gene assem 68 .................................................. 117
```

FIG. 7A (CONT.)

Mouse 2D12.5 VL - Human TetTox CL kappa (light chain gene)

```
                                             460       470       480       490       500
                                        ....|....|....|....|....|....|....|....|....|....|
2dVL-TTCL native_cloned            451  CAGTGGAAGGTGGATAACGCCCTCCAATCGGGTAACTCCCAGGAGAGTGT 500
2dVL-TTCL N53C_cloned              451  .................................................. 500
2d12.5 VL native hybridoma
TTCL template for gene assem       118  .................................................. 167

                                             510       520       530       540       550
                                        ....|....|....|....|....|....|....|....|....|....|
2dVL-TTCL native_cloned            501  CACAGAGCAGGACAGCAAGGACAGCACCTACAGCCTCAGCAGCACCCTGA 550
2dVL-TTCL N53C_cloned              501  .................................................. 550
2d12.5 VL native hybridoma
TTCL template for gene assem       168  .................................................. 217

                                             560       570       580       590       600
                                        ....|....|....|....|....|....|....|....|....|....|
2dVL-TTCL native_cloned            551  CGCTGAGCAAAGCAGACTACGAGAAACACAAAGTCTACGCCTGCGAAGTC 600
2dVL-TTCL N53C_cloned              551  .................................................. 600
2d12.5 VL native hybridoma
TTCL template for gene assem       218  .................................................. 267
```

FIG. 7B

```
                                            610       620       630       640       650
                                    ....|....|....|....|....|....|....|....|....|....|
2dVL-TTCL native_cloned        601 ACCCATCAGGGCCTGAGCTTGCCCGTCACAAAGAGCTTCAACAGGGGAGA 650
2dVL-TTCL N53C_cloned          601 ...........T...................................... 650
2d12.5 VL native hybridoma
TTCL template for gene assem   268 .................................................. 317

                                            660
                                    ....|....|....
2dVL-TTCL native_cloned        651 GTGTTAATTCTAGA 664
2dVL-TTCL N53C_cloned          651 .............. 664
2d12.5 VL native hybridoma
TTCL template for gene assem   318 .....          322
```

Figure 8:
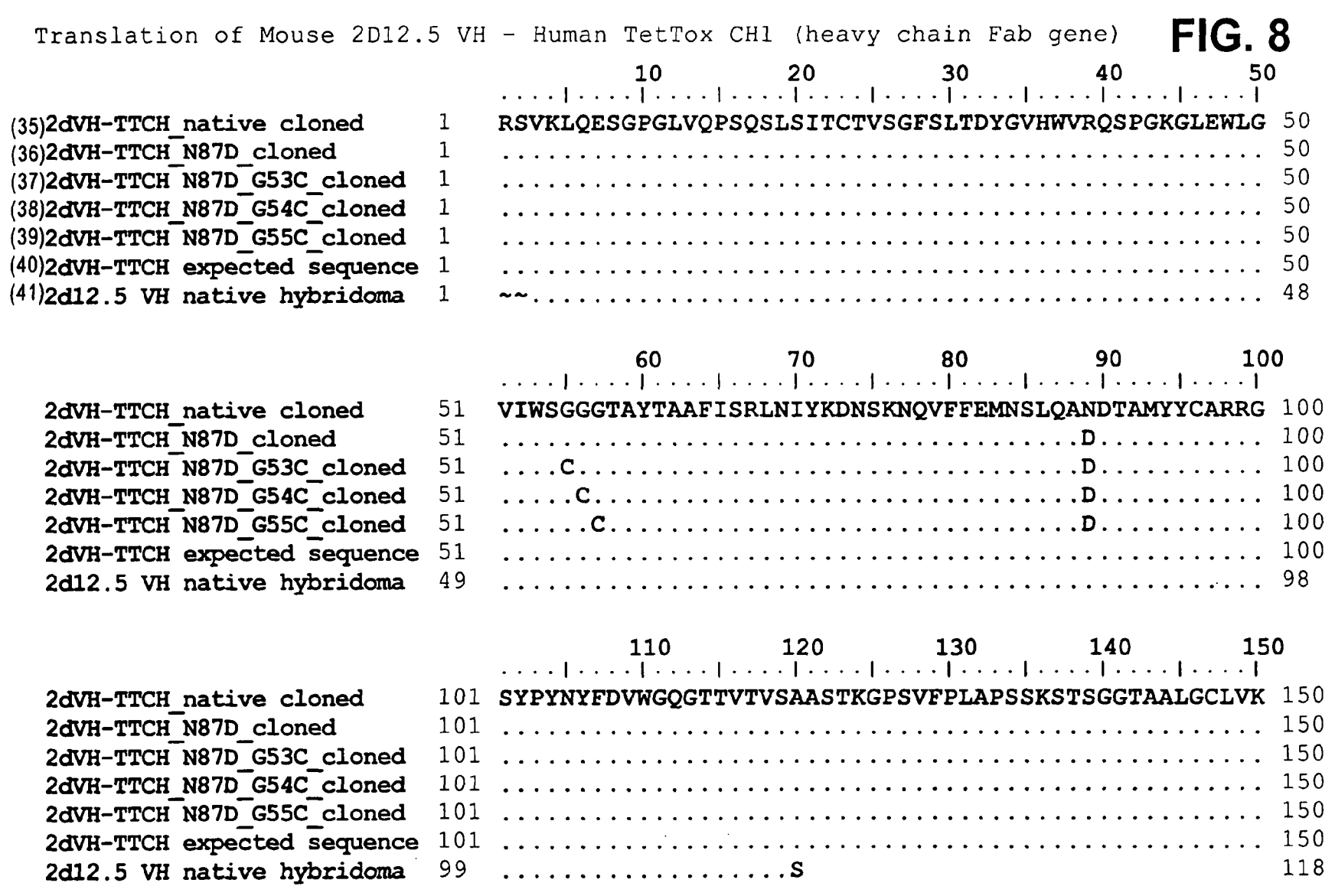

Translation of Mouse 2D12.5 VH - Human TetTox CH1 (heavy chain Fab gene)

```
                                            10        20        30        40        50
                                   ....|....|....|....|....|....|....|....|....|....|
(35)2dVH-TTCH_native cloned     1  RSVKLQESGPGLVQPSQSLSITCTVSGFSLTDYGVHWVRQSPGKGLEWLG 50
(36)2dVH-TTCH_N87D_cloned       1  .................................................. 50
(37)2dVH-TTCH_N87D_G53C_cloned  1  .................................................. 50
(38)2dVH-TTCH_N87D_G54C_cloned  1  .................................................. 50
(39)2dVH-TTCH_N87D_G55C_cloned  1  .................................................. 50
(40)2dVH-TTCH expected sequence 1  .................................................. 50
(41)2d12.5 VH native hybridoma  1  ~~................................................ 48

                                            60        70        80        90       100
                                   ....|....|....|....|....|....|....|....|....|....|
2dVH-TTCH_native cloned        51  VIWSGGGTAYTAAFISRLNIYKDNSKNQVFFEMNSLQANDTAMYYCARRG 100
2dVH-TTCH_N87D_cloned          51  ....................................D............. 100
2dVH-TTCH_N87D_G53C_cloned     51  ....C...............................D............. 100
2dVH-TTCH_N87D_G54C_cloned     51  .....C..............................D............. 100
2dVH-TTCH_N87D_G55C_cloned     51  ......C.............................D............. 100
2dVH-TTCH expected sequence    51  .................................................. 100
2d12.5 VH native hybridoma     49  .................................................. 98

                                           110       120       130       140       150
                                   ....|....|....|....|....|....|....|....|....|....|
2dVH-TTCH_native cloned       101  SYPYNYFDVWGQGTTVTVSAASTKGPSVFPLAPSSKSTSGGTAALGCLVK 150
2dVH-TTCH_N87D_cloned         101  .................................................. 150
2dVH-TTCH_N87D_G53C_cloned    101  .................................................. 150
2dVH-TTCH_N87D_G54C_cloned    101  .................................................. 150
2dVH-TTCH_N87D_G55C_cloned    101  .................................................. 150
2dVH-TTCH expected sequence   101  .................................................. 150
2d12.5 VH native hybridoma     99  ...................S                               118
```

```
                                         160       170       180       190       200
                                 ....|....|....|....|....|....|....|....|....|....|
2dVH-TTCH_native cloned      151 DYFPEPVTVSWNSGALTSGVHTFPAVLQSSGLYSLSSVVTVPSSSLGTQT 200
2dVH-TTCH_N87D_cloned        151 .................................................. 200
2dVH-TTCH_N87D_G53C_cloned   151 .................................................. 200
2dVH-TTCH_N87D_G54C_cloned   151 .................................................. 200
2dVH-TTCH_N87D_G55C_cloned   151 .................................................. 200
2dVH-TTCH expected sequence  151 .................................................. 200
2d12.5 VH native hybridoma

                                         210       220
                                 ....|....|....|....|....|..
2dVH-TTCH_native cloned      201 YICNVNHKPSNTKVDKKAEPKSCDKSR 227
2dVH-TTCH_N87D_cloned        201 ........................... 227
2dVH-TTCH_N87D_G53C_cloned   201 ........................... 227
2dVH-TTCH_N87D_G54C_cloned   201 ........................... 227
2dVH-TTCH_N87D_G55C_cloned   201 ........................... 227
2dVH-TTCH expected sequence  201 ........................... 227
2d12.5 VH native hybridoma
```

Mouse 2D12.5 VH - Human TetTox CH1 (heavy chain Fab gene)

```
                                             10        20        30        40        50
                                    ....|....|....|....|....|....|....|....|....|....|
(42) 2dVH-TTCH_native cloned     1  AGATCTGTGAAGCTGCAGGAGTCTGGACCTGGCCTAGTGCAGCCCTCACA 50
(43) 2dVH-TTCH_N87D_cloned        1  .................................................. 50
(44) 2dVH-TTCH N87D_G53C_cloned  1  .................................................. 50
(45) 2dVH-TTCH_N87D_G54C_cloned  1  ..........................G....................... 50
(46) 2dVH-TTCH N87D_G55C_cloned  1  .................................................. 50
(47) 2dVH-TTCH expected sequence 1  .................................................. 50
(48) 2d12.5 VH native hybridoma  1  ~~~~~~.................A.......................... 44

                                             60        70        80        90       100
                                    ....|....|....|....|....|....|....|....|....|....|
     2dVH-TTCH_native cloned     51 GAGCCTGTCCATCACCTGCACGGTCTCTGGTTTCTCATTAACTGACTATG 100
     2dVH-TTCH_N87D_cloned       51 .................................................. 100
     2dVH-TTCH N87D_G53C_cloned  51 .................................................. 100
     2dVH-TTCH_N87D_G54C_cloned  51 .................................................. 100
     2dVH-TTCH N87D_G55C_cloned  51 .................................................. 100
     2dVH-TTCH expected sequence 51 .................................................. 100
     2d12.5 VH native hybridoma  45 .................................................. 94

                                            110       120       130       140       150
                                    ....|....|....|....|....|....|....|....|....|....|
     2dVH-TTCH_native cloned    101 GTGTACACTGGGTTCGCCAGTCTCCAGGAAAGGGTCTGGAATGGCTGGGA 150
     2dVH-TTCH_N87D_cloned      101 .................................................. 150
     2dVH-TTCH N87D_G53C_cloned 101 .................................................. 150
     2dVH-TTCH_N87D_G54C_cloned 101 .................................................. 150
     2dVH-TTCH N87D_G55C_cloned 101 .................................................. 150
     2dVH-TTCH expected sequence 101 .................................................. 150
     2d12.5 VH native hybridoma  95 .................................................. 144
```

```
                                        160       170       180       190       200
                                    ....|....|....|....|....|....|....|....|....|....|
2dVH-TTCH_native cloned        151  GTGATATGGAGTGGTGGAGGCACGGCCTATACTGCGGCGTTCATATCCAG  200
2dVH-TTCH_N87D_cloned          151  ..................................................  200
2dVH-TTCH_N87D_G53C_cloned     151  ............T.....................................  200
2dVH-TTCH_N87D_G54C_cloned     151  ..............T.T.................................  200
2dVH-TTCH_N87D_G55C_cloned     151  .................T................................  200
2dVH-TTCH expected sequence    151  ..................................................  200
2d12.5 VH native hybridoma     145  ..................................................  194

                                        210       220       230       240       250
                                    ....|....|....|....|....|....|....|....|....|....|
2dVH-TTCH_native cloned        201  ACTGAACATCTACAAGGACAATTCCAAGAACCAAGTTTTCTTTGAAATGA  250
2dVH-TTCH_N87D_cloned          201  ..................................................  250
2dVH-TTCH_N87D_G53C_cloned     201  ..................................................  250
2dVH-TTCH_N87D_G54C_cloned     201  ..................................................  250
2dVH-TTCH_N87D_G55C_cloned     201  ..................................................  250
2dVH-TTCH expected sequence    201  ..................................................  250
2d12.5 VH native hybridoma     195  ..................................................  244

                                        260       270       280       290       300
                                    ....|....|....|....|....|....|....|....|....|....|
2dVH-TTCH_native cloned        251  ACAGTCTGCAAGCTAATGACACAGCCATGTATTACTGTGCCAGAAGGGGT  300
2dVH-TTCH_N87D_cloned          251  ..............G...................................  300
2dVH-TTCH_N87D_G53C_cloned     251  ..............G...................................  300
2dVH-TTCH_N87D_G54C_cloned     251  ..............G...................................  300
2dVH-TTCH_N87D_G55C_cloned     251  ..............G...................................  300
2dVH-TTCH expected sequence    251  ..................................................  300
2d12.5 VH native hybridoma     245  ..................................................  294

                                        310       320       330       340       350
                                    ....|....|....|....|....|....|....|....|....|....|
```

Mouse 2D12.5 VH - Human TetTox CH1 (heavy chain Fab gene)

```
2dVH-TTCH_native cloned          301 AGCTACCCTTACAACTACTTCGATGTCTGGGGCCAAGGGACCACGGTCAC 350
2dVH-TTCH_N87D_cloned            301 .................................................. 350
2dVH-TTCH_N87D_G53C_cloned       301 .................................................. 350
2dVH-TTCH_N87D_G54C_cloned       301 .................................................. 350
2dVH-TTCH_N87D_G55C_cloned       301 .................................................. 350
2dVH-TTCH expected sequence      301 .................................................. 350
2d12.5 VH native hybridoma       295 ............................................A..... 344

                                              360       370       380       390       400
                                     ....|....|....|....|....|....|....|....|....|....|
2dVH-TTCH_native cloned          351 CGTCTCCGCAGCCTCCACCAAGGGCCCATCGGTCTTCCCCCTGGCACCCT 400
2dVH-TTCH_N87D_cloned            351 .................................................. 400
2dVH-TTCH_N87D_G53C_cloned       351 .................................................. 400
2dVH-TTCH_N87D_G54C_cloned       351 .................................................. 400
2dVH-TTCH_N87D_G55C_cloned       351 .................................................. 400
2dVH-TTCH expected sequence      351 .................................................. 400
2d12.5 VH native hybridoma       345 .......T..                                         354

                                              410       420       430       440       450
                                     ....|....|....|....|....|....|....|....|....|....|
2dVH-TTCH_native cloned          401 CCTCCAAGAGCACCTCTGGGGGCACAGCGGCCCTGGGCTGCCTGGTCAAG 450
2dVH-TTCH_N87D_cloned            401 .................................................. 450
2dVH-TTCH_N87D_G53C_cloned       401 .................................................. 450
2dVH-TTCH_N87D_G54C_cloned       401 .................................................. 450
2dVH-TTCH_N87D_G55C_cloned       401 .................................................. 450
2dVH-TTCH expected sequence      401 .................................................. 450
2d12.5 VH native hybridoma
```

```
                                       460       470       480       490       500
                                  ....|....|....|....|....|....|....|....|....|....|
2dVH-TTCH_native cloned       451 GACTACTTCCCCGAACCGGTGACGGTGTCTTGGAACTCAGGCGCCCTGAC 500
2dVH-TTCH_N87D_cloned         451 .................................................. 500
2dVH-TTCH_N87D_G53C_cloned    451 .................................................. 500
2dVH-TTCH_N87D_G54C_cloned    451 .................................................. 500
2dVH-TTCH_N87D_G55C_cloned    451 .................................................. 500
2dVH-TTCH expected sequence   451 .............................G.................... 500
2d12.5 VH native hybridoma

                                       510       520       530       540       550
                                  ....|....|....|....|....|....|....|....|....|....|
2dVH-TTCH_native cloned       501 CAGCGGCGTGCACACCTTCCCGGCTGTCCTACAGTCCTCAGGACTCTACT 550
2dVH-TTCH_N87D_cloned         501 .................................................. 550
2dVH-TTCH_N87D_G53C_cloned    501 .................................................. 550
2dVH-TTCH_N87D_G54C_cloned    501 .................................................. 550
2dVH-TTCH_N87D_G55C_cloned    501 .................................................. 550
2dVH-TTCH expected sequence   501 .................................................. 550
2d12.5 VH native hybridoma

                                       560       570       580       590       600
                                  ....|....|....|....|....|....|....|....|....|....|
2dVH-TTCH_native cloned       551 CCCTCAGCAGCGTGGTGACCGTGCCCTCCAGCAGCTTGGGCACCCAGACC 600
2dVH-TTCH_N87D_cloned         551 .................................................. 600
2dVH-TTCH_N87D_G53C_cloned    551 .................................................. 600
2dVH-TTCH_N87D_G54C_cloned    551 .................................................. 600
2dVH-TTCH_N87D_G55C_cloned    551 .................................................. 600
2dVH-TTCH expected sequence   551 .................................................. 600
2d12.5 VH native hybridoma

                                       610       620       630       640       650
                                  ....|....|....|....|....|....|....|....|....|....|
2dVH-TTCH_native cloned       601 TACATCTGCAACGTGAATCACAAGCCCAGCAACACCAAGGTGGACAAGAA 650
2dVH-TTCH_N87D_cloned         601 .................................................. 650
```

Mouse 2D12.5 VH - Human TetTox CH1 (heavy chain Fab gene)

```
2dVH-TTCH_N87D_G53C_cloned    601 .................................................. 650
2dVH-TTCH_N87D_G54C_cloned    601 .................................................. 650
2dVH-TTCH_N87D_G55C_cloned    601 .................................................. 650
2dVH-TTCH expected sequence   601 .................................................. 650
2d12.5 VH native hybridoma

                                           660       670       680
                                  ....|....|....|....|....|....|.
2dVH-TTCH_native cloned       651 AGCAGAGCCCAAATCTTGTGACAAATCTAGA 681
2dVH-TTCH_N87D_cloned         651 ............................... 681
2dVH-TTCH_N87D_G53C_cloned    651 ............................... 681
2dVH-TTCH_N87D_G54C_cloned    651 ............................... 681
2dVH-TTCH_N87D_G55C_cloned    651 ............................... 681
2dVH-TTCH expected sequence   651 ............................... 681
2d12.5 VH native hybridoma
```

FIG. 9C

Strategy for Assembly of Chimeric 2D12.5
Heavy Chain
Step 1

PCR Reaction A PCR Reaction B

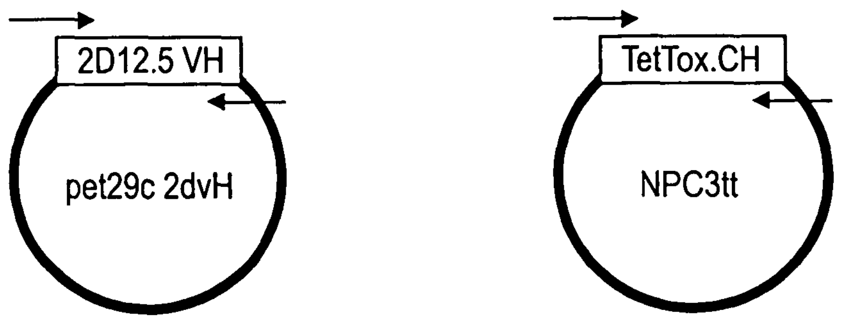

PCR Products

A

B

| PCR cycle - 2DTTover | Example reaction | |
|---|---|---|
| 1 - 94° C 10 min | d2H2O | 63ul |
| 2 - 94° C 1 min | 10x buffer | 10uL |
| 3 - 62° C 1 min | 25mM MgCl2 | 8uL |
| 4 - 72° C 2 min | 2mM dNTP | 10uL |
| 5 - 25x to step 2 | Template 1 (1ng/ uL) | 1uL |
| 6 - 72° C 5 min | Top Primer 25pmol/ uL | 4uL |
| 7 - 4° C 18 hr | Bottom Primer 25 pmol/ uL | 4uL |
| 8 - END | Taq Polymerase | 0.5uL |
| Taq added before step 2 | | |

Primers

→ VH2D5' BglII
GAAGATCTGTGAAGCTGCAGGAGTCTGGAC

← VH2DTTMi
GCCCTTGGTGGAGGCTGCGGAGACGGTGACC-GTGG

→ CHTT2DMi
CCACGGTCACCGTCTCCGCAGCCTCCAC-CAAGGGC

← TTCH3' Xba
CGATCTAGATTTGTCACAAGATTTGGGCTCTGC

FIG. 10A

Strategy for Assembly of Chimeric 2D12.5
Heavy Chain
Step 2

PCR Reaction

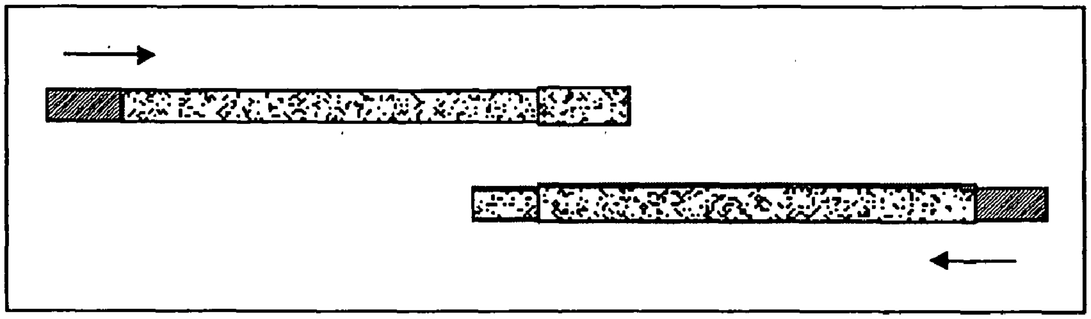

PCR cycle - 2DTTVent
1 - 95°C 10 min
2 - 94°C 1 min
3 - 60°C 1 min
4 - 75°C 2 min
5 - 4x to step 2
6 - 94°C 1 min
7 - 63°C 1 min
8 - 75°C 2 min
9 - 25x to step 6
10 - 72°C 5 min
11 - 4°C 18 hr
12 - END
Vent added before step 2
Primers added before step 6

Primers

→ VH2D5' BglII
GAAGATCTGTGAAGCTGCAGGAGTCTGGACC

← TTCH3' Xba
CGATCTAGATTTGTCACAAGATTTGGGCTCTGC

Example reaction

| | |
|---|---|
| d2H2O | 70ul |
| 10x buffer | 10uL |
| 100mM MgSO4 | 0uL |
| 2mM dNTP | 10uL |
| Template 1(1ng/ uL) | 1uL |
| Template 2(1ng/ uL) | 1uL |
| Top Primer 25pmol/ uL | 4uL |
| Bottom Primer 25 pmol/ uL | 4uL |
| Vent Polymerase | 0.5uL |

PCR Assembly Product

FIG. 10B

Strategy for Assembly of Chimeric 2D12.5
Heavy Chain
Step 3
Desired PCR Assembly Product
Restriction Digest PCR Product with Bgl II & Xba I
Ligate Restriction Digested PCR Product into pMTBipV5His
(S2 Cell Expression Vector, Propagated in XL-1 Blue E. Coli)
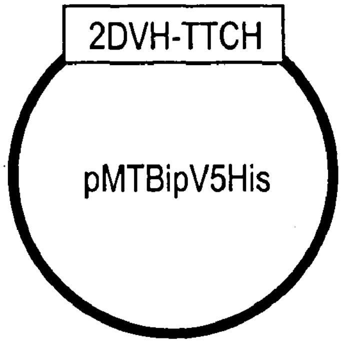
FIG. 10C Step 2 - Mutation Methodology (PCR Reaction VHMUTTAQ)

2nd PCR Reaction (Mix Products of reaction A and B)
    1) Extend
       2) Amplify with outer primers (MTforward and BGHreverse)

2nd PCR Reaction Products (Mixture - 2 Products of equal size)

Restriction Digest PCR Product Mixture with BglII and Xba1

Step 1 - PCR Reaction MT-VENT

PCR cycle - MT-VENT
1 - 95° C 10 min
2 - 94° C 1 min
3 - 50° C 1 min
4 - 75° C 2 min
5 - 24x to step 2
6 - 75° C 5 min
7 - 4° C 18 hr
8 - END
VENT added before step 2
Primers added before step 1

| Example reaction | |
|---|---|
| d2H2O | 70ul |
| 10x buffer | 10uL |
| 100mM MgSO4 | 0uL |
| 2mM dNTP | 10uL |
| Template (1ng/uL) | 1uL |
| Top Primer 25pmol/uL | 4uL |
| Bottom Primer 25pmol/uL | 4uL |
| Vent Polymerase | 0.5uL |

Step 2 - PCR Reaction VHMUTTAQ

PCR cycle - VHMUTTAQ
1 - 95° C 10 min
2 - 94° C 1 min
3 - 68° C 1 min
4 - 72° C 2 min
5 - 4x to step 2
6 - 94° C 1 min
7 - 50° C 2 min
8 - 72° C 2 min
9 - 24x to step 6
10 - 72° C 5 min
11 - 4° C 18 hr
12 - END
Taq added before step 2
Primers added before step 6

| Example reaction | |
|---|---|
| d2H2O | 61ul |
| 10x buffer | 10uL |
| 25mM MgCl2 | 8uL |
| 2mM dNTP | 10uL |
| Template 1 (1ng/uL) | 1uL |
| Template 2 (1ng/uL) | 1uL |
| Top Primer 25pmol/uL | 4uL |
| Bottom Primer 25pmol/uL | 4uL |
| Taq Polymerase | 0.5uL |

FIG. 10F

Strategy for Assembly of Chimeric 2D12.5
Light Chain
Step 1

Primers

→ 2dVL5' Bgl
GAAGATCTGCTGTTGTGACTCAGGAATCT

← 2dVLMiBot
AGATGGTGCAGCCACAGTTCGGCTTAGGA-
CAGTCAGTTTGGT

→ 2dVLMiTop
ACCAAACTGACTGTCCTAAGCCGAACTGT-
GGCTGCACCATCT

← TTCL3' Xba
CGATCTAGAATTAACACTCTCCCCTG

Strategy for Assembly of Chimeric 2D12.5
Light Chain
Step 2

PCR Reaction

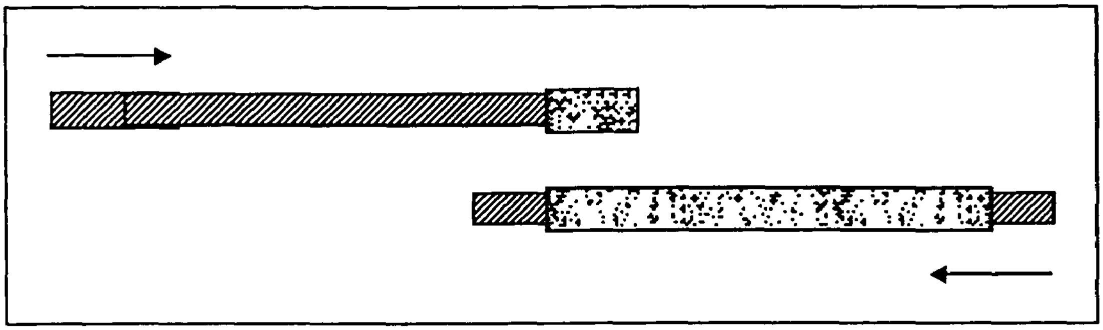

Primers

2dVL5' Bgl
GAAGATCTGCTGTTGTGACTCAGGAATCT

TTCL3' Xba
CGATCTAGAATTAACACTCTCCCCTG

PCR Assembly Product

Problem: There is an unwanted G48S mutation in the variable domain.

Solution: Repair with an S48G primer using the method of Ito. Also institute a mutation at N53C and repair point mutation with a single primer named S48G_N53C.

FIG. 11B

Strategy for Assembly of Chimeric 2D12.5 Light Chain
Step 3

Desired PCR Assembly Product

Restriction Digest PCR Product with Bgl II & Xba I

Ligate Restriction Digested PCR Product into pMTBipV5His
(S2 Cell Expression Vector, Propagated in XL-1 Blue E. Coli)

Step 1 - Mutation Methodology (PCR Reaction MT-VENT)

```
                       Start of transcription              MT Forward priming site
771   GCCAATGTGC ATCAGTTGTG GTCAGCAGCA AAATCAAGTG AATCATCTCA GTGCAACTAA
                                              BiP signal sequence
831   AGGGGGGATC CGATCTCAAT ATG AAG TTA TGC ATA TTA CTG GCC GTC GTG GCC TTT
                               Met Lys Leu Cys Ile Leu Leu Ala Val Val Ala Phe
                        Bgl II
887   GTT GGC CTC TCG CTC GGG AGATCT [░░░░░░░░2DVH░░░░░░░░]
      Val Gly Leu Ser Leu Gly  Signal cleavage site
                           AGATGT                   Xba I      Aba I
945   [░░░░░░░░░░░░░░░░░░░░░░░░░░] TAGAGGGC CGTTCGAA GGT AAG
                                                             Gly Lys
                 V5 epitope                    STOP   Age I   Polyhistidine
1009  CCT ATC CCT AAC CCT CTC CTC GGT CTC GAT TCT ACG CGT ACC GGT CAT CAT CAC
      Pro Ile Pro Asn Pro Leu Leu Gly Leu Asp Ser Thr Arg Thr Gly His His His
      Region           Pme I                  pcDNA 3.1/BGH Reverse priming site
1063  CAT CAC CAT TGA GTTTAAACCC GCTGATCAGC CTCGACTGTG CCTTCTAAGG CCTGAGCTCG
      His His His ***
```

1st Set of PCR Reactions Producta A and B)

| | |
|---|---|
| CATCTCAGTGCAACTAAA | MTforward |
| CACCTATTAGACCAGTGAATAAATG | 2dvL_S48G_pMTBip |
| | OR |
| CGGTTATTACAACCACCTATTAGACCAGT-GAATAAATG | S48G_N53C_pMTBip |

| | |
|---|---|
| GCTCGGGAGATGTGCTGTTGTG | 2dvLKGglII_pMTBip |
| TAGAAGGCACAGTCGAGG | BGHreverse |

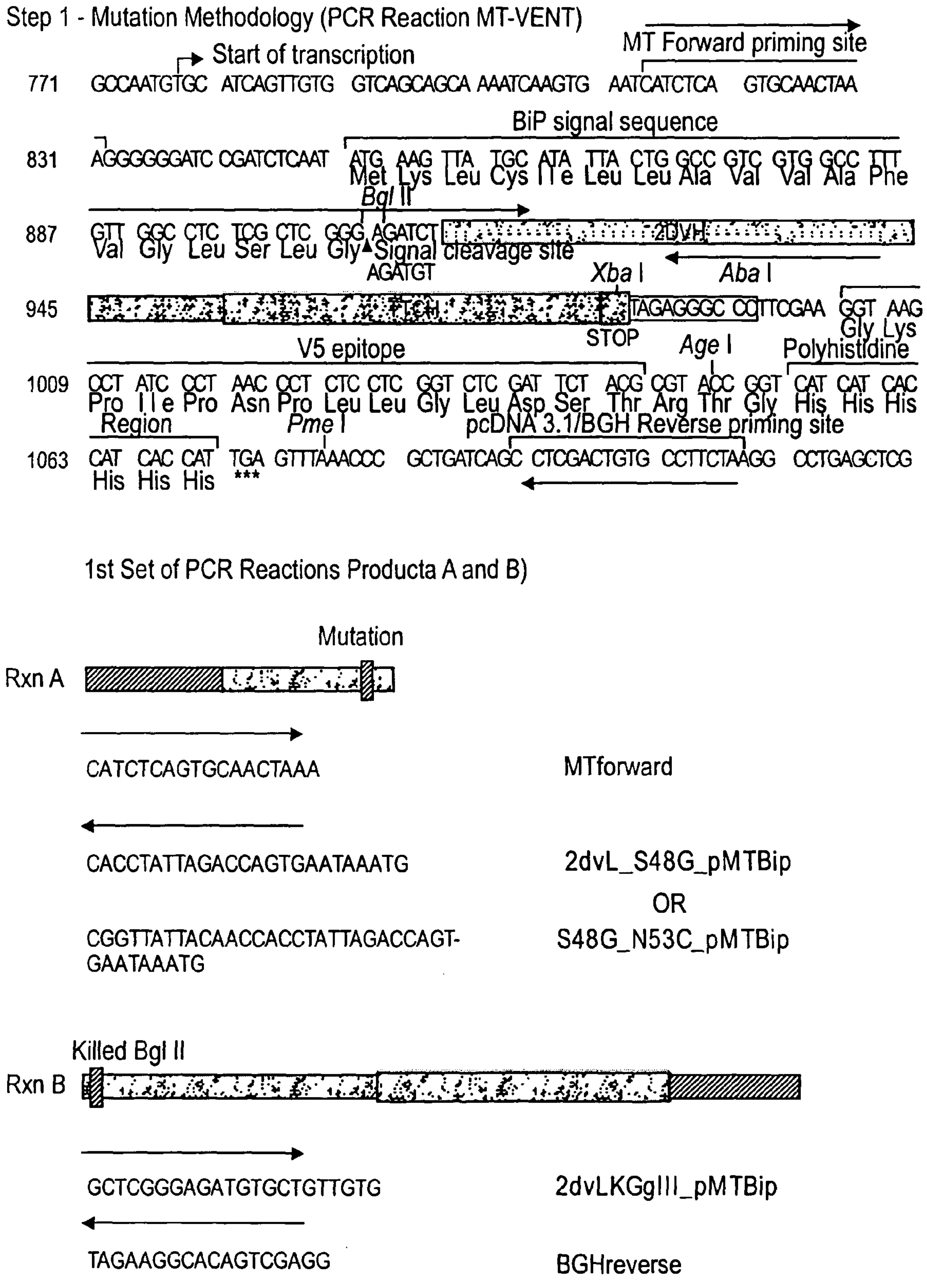

FIG. 11D

Step 2 - Mutation Methodology (PCR Reaction VHMUTTAQ)

2nd PCR Reaction Mix Products of reaction B)
    1) Extend
    2) Amplify with outer primers (MTforward and BGHreverse)

Mutation

Rxn A

Killed Bgl II

Rxn B

2nd PCR Reaction Products (Mixture - 2 Products of equal size)
                                  Mutation Killed Bgl II Restriction Digest PCR Product Mixture with BglII and Xba1

Killed Bgl II

Strategy for Assembly of Chimeric 2D12.5
Light Chain
Step 4

PCR Reaction A

PCR Reaction B

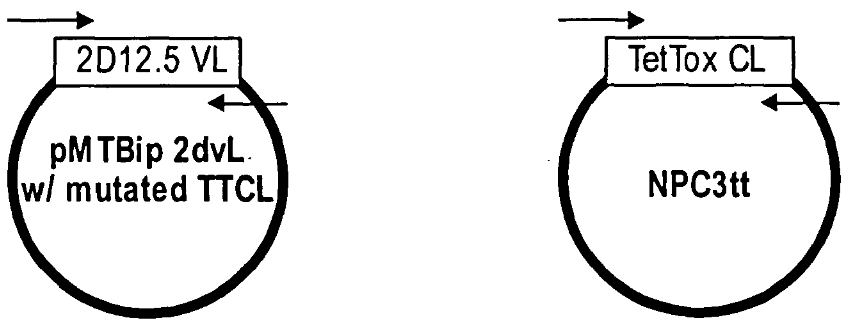

PCR Products

A

B

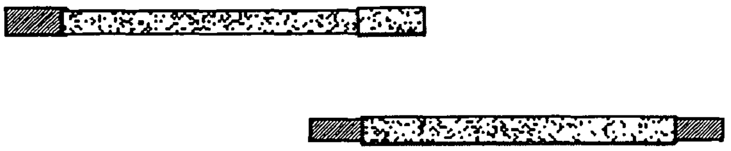

| PCR cycle - 2DTTover | Example reaction | |
|---|---|---|
| 1 - 94° C 10 min | d2H2O | 63ul |
| 2 - 94° C 1 min | 10x buffer | 10uL |
| 3 - 62° C 1 min | 25mM MgCl2 | 8uL |
| 4 - 72° C 2 min | 2mM dNTP | 10uL |
| 5 - 25x to step 2 | Template 1 (1ng/ uL) | 1uL |
| 6 - 72° C 5 min | Top Primer 25pmol/ uL | 4uL |
| 7 - 4° C 18 hr | Bottom Primer 25 pmol/ uL | 4uL |
| 8 - END | Taq Polymerase | 0.5uL |
| Taq added before step 2 | | |

Primers

→ Mtforward
CATCTCAGTGCAACTAAA

→ 2dVLMiTop
ACCAAAACTGACTGTCCTAAGCCGAACT-
GTGGCTGCACCATCT

← 2dVLMiBot
AGATGGTGCAGCCACAGTTCGGCTTAGGA-
CAGTCAGTTTGGT

← TTCL3' Xba
CGATCTAGAATTAACACTCTCCCCTG

FIG. 11F

MULTI-FUNCTIONAL ANTIBODIES

CROSS-REFERENCES TO RELATED APPLICATIONS

This application is a continuation-in-part of U.S. patent application Ser. No. 10/350,555, filed Jan. 23, 2003, the disclosure of which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. CA16861, awarded by the NIH/NCI to C. F. Meares. The Government has certain rights in this invention.

BACKGROUND OF THE INVENTION

Over a million new cases of cancer will be diagnosed this year in the United States. While surgery can often provide definitive treatment of cancer in its early stages, the eradication of metastases is crucial to the cure of more advanced disease. Chemotherapeutic drugs are used in combinations for this purpose, with considerable success. Nonetheless, over half a million Americans will die from cancer this year. Progressions and relapses following surgery and chemotherapy/radiation are not uncommon, and in most cases the second line of treatment is of limited use. Despite the expenditure of large amounts of public and private resources over many years, better treatments for cancer are sorely needed.

Currently there are approximately 100 antineoplastic drugs on the market. Their systemic use is associated with undesirable side effects including toxicity to normal cells, which limits the doses used for treatment of the disease. Most pharmaceuticals consist of small organic molecules, which effectively traverse cell membranes and become widely distributed through the body. As reviewed by Langer, polymer-based pharmaceutical agents provide a variety of new approaches to safer and better therapies (see, Langer R, *Nature,* 392 (6679) SUPPS: 5-10 (1998)). Polymers and other macromolecules do not traverse membranes; however, they may be selectively accumulated in the interstitial space of a tumor, since tumors typically do not possess an efficient lymphatic drainage system (Yuan et al., *Cancer Research* 51(12): 3119-30 (1991)). Developing technology to target therapeutic drugs to cancer cells, while sparing normal cells, is a promising approach to improved treatment; visualizing small cancers by means of targeting reagents is already a productive area of investigation.

The residence of macromolecules in tumors may be prolonged if they become anchored to immobile elements, such as polymorphic epithelial mucin (PEM), the secreted product of the MUC1 gene (Taylor-Papadimitriou et al., *Trends Biotechnol.,* 12(6): 227-33 (1994)); or HLA-DR, a long-lived cell surface protein (Rose et al., *Cancer Immunology Immunotherapy,* 43: 26-30 (1996). The reagents of choice for this anchoring reaction are monoclonal antibodies and their derivatives. Currently there is a good selection of such macromolecules that bind to highly expressed tumor antigens, and that do not bind significantly to normal cells. Examples include, HMFG1 (Nicholson et al., *Oncology Reports* 5: 223-226 (1998)); L6 (DeNardo et al., *Journal of Nuclear Medicine* 39: 842-849 (1998)); and Lym-1 (DeNardo et al., *Clinical Cancer Research,* 3: 71-79 (1997)). The latter three antibodies have been conjugated to metal chelates for radioimmunotherapy and studied extensively in recent years, and are in clinical trials at various stages.

Recent data indicate that immunoconjugates have efficacy comparable to conventional antineoplastic drugs, and work in synergy with them (see, for example, Nicholson et al., *Oncology Reports* 5: 223-226 (1998); and DeNardo et al., *Proceedings of the National Academy of Sciences USA* 94: 4000-4004 (1997)). The emerging success of metal radioimmunoconjugates for cancer detection and treatment owes much to the development of metal-binding molecules (bifunctional chelating agents) appropriate for use in vivo, and to the further development of linkers that reduce concentrations of the metal binding molecules in nontarget tissues (see, Sundberg et al., *Nature* 250: 587-588 (1974); Yeh et al., *Analytical Biochemistry* 100: 152-159 (1979); Moi et al., *Analytical Biochemistry* 148: 249-253 (1985); Moi et al., *Journal of the American Chemical Society* 110: 6266-6267 (1988); and Li et al., *Bioconjugate Chemistry* 4: 275-283 (1993).

An alternative view of the potential for use of antibodies in cancer diagnosis and therapy is that, rather than carrying a radionuclide to a tumor, they can carry a receptor for a radionuclide (e.g., for a metal chelate). Antibodies against metal chelates can bind target molecules with high affinity and exquisite specificity and thus, can conveniently be used for applications in chemistry, environmental science, and medicine (see, e.g., Reardan et al., *Nature* 316: 265-268 (1985); Barbas et al., *Proc. Natl. Acad. Sci. U.S.A.* 90: 6385-6389 (1993); Blake et al., *J. Biol. Chem.* 271: 27677-27685 (1996); Brummer et al., *Bioorg. Med. Chem.* 9: 2253-2257 (2001); Schuhmacher et al., *Cancer Res.* 61: 3712-3717 (2001); Johnson et al., *Environ. Sci. Technol.* 36: 1042-1047 (2002)). For example, an antibody that binds rare earth complexes selectively could be used as a docking station for a set of probe molecules, of particular interest for medical imaging and therapy (see, e.g., Lubic et al., *J. Nucl. Med.* 42: 670-678 (2001) and Bosslet et al., *Br. J. Cancer* 63: 681-686 (1991)). The rare earths are rich in probe properties, such as the paramagnetism of Gd, the luminescence of Th and Eu, and the nuclear properties of Y and Lu. The chelating ligand DOTA (1,4,7,10-tetraazacyclododecane-N,N',N",N'"-tetraacetic acid) is generally useful for binding transition metals and rare earths with extreme stability under physiological conditions, leading to their use in vivo for targeted imaging and therapy (see, e.g., Loncin et al., *Inorg. Chem.* 25: 2646-2648 (1986); Geraldes et al., *Magn. Reson. Med.* 3: 242-250 (1986); Wu et al., *Proc. Natl. Acad. Sci. U.S.A.* 97: 8495-8500 (2000); and Waldherr et al., *J. Nucl. Med.* 43: 610-616 (2002)).

Antibodies with dual binding specificity have been prepared which can, e.g., cross-link tumor cells to cytokines such as tumor necrosis factor (Bruno et al., *Cancer Res.* 56(20): 4758-4765 (1996)). Likewise, bispecific antibodies that can bind to tumors and to metal chelates have been developed (Stickney et al., *Cancer Res.* 51(24): 6650-5 (1991); Rouvier et al., *Horm. Res.* 47(4-6): 163-167 (1997)). When pretargeted to tumors, these bispecific antibodies bind to antigens and remain on the target, providing receptors for metal chelates. Subsequent administration of small, hydrophilic metal chelates leads to their capture by the targeted chelate receptors. Uncaptured chelates clear quickly through the kidneys and out of the body, leaving very little radioactivity in normal tissues. This strategy is known as "pretargeting."

A triumph of this approach was the imaging of metastatic cancer in the liver by an indium-111 chelate (Stickney et al., *Cancer Res.* B(24): 6650-5 (1991)). Antibodies conventionally conjugated to metal chelates are catabolized in the liver, and generally produce a radioactive background that masks tumors in that organ. The excellent tumor-to-background uptake ratios achieved by the pretargeting approach have led to considerable exploration of improvements in methodology. The anti-chelate antibody CHA255, initially developed for this purpose, possesses a high binding constant for (S)-benzyl-EDTA-indium chelates ($K_S \approx 4\times10^9$) and exquisite specificity for these haptens (Dayton et al., *Nature* 316: 265-268 (1985). On CHA255, the bound lifetimes of various indium chelates at 37° C. were found to be in the 10-40 min range (Meyer, et al, *Bioconjugate Chem.* 1(4): 278-84 (1990)).

Another anti-chelate antibody, 2D12.5, possesses a high binding constant for (S) nitrobenzyl-DOTA chelates and Janus-DOTA, a bivalent form of DOTA ($K_S \approx 10^8$) (Goodwin et al., *Canc. Res.* 54(22): 5937-46 (1994) and Lubic et al., *J. Nucl. Med.* 42(4): 670-78 (2001)). In vivo clearance studies have demonstrated that 74-96% of 2D12.5 bound to metal chelates is present 24 hours after administration of the bound complex.

The need to enhance the antibody-hapten bound lifetime has led to the use of the long-lived avidin-biotin interaction, employing biotinylated metal chelates (Chinol et al., *Nuclear Medicine Communications* 18: 176-182 (1997)) in place of the original antibody-hapten interaction between CHA255 and benzyl-EDTA-indium derivatives. Here one assembles an antibody-avidin-chelate complex at the target in two or three steps, by sequential administration of nonradiolabeled proteins with a final administration of a biotinyl chelate carrying a radiometal. The extremely high affinity biotin-avidin association is adequately long-lived even for therapeutic applications (Theodore L J. et al, WO 9515979). Hen egg avidin and bacterial streptavidin, however, are both nonhuman, tetrameric proteins: their immunogenic properties are inconvenient, and the reversible associations between their subunits may limit their effectiveness. Thus, an improved strategy is still needed.

A delivery strategy based on the formation of a covalent bond between a chelate and an antibody that specifically recognizes and binds the chelate would represent a significant improvement over the methods now in use. The present invention provides engineered antibodies and chelates that react with one another to form covalent bonds and methods of using the engineered constructs to perform analyses and treat diseases.

SUMMARY OF THE INVENTION

An object of the present invention is the engineering of antibodies that recognize chelating agents and metal chelates, particularly macrocyclic metal chelates. The antibodies of the invention are desirable for use as analytical reagents and in diagnosis and therapy. For example, certain antibodies of the invention recognize and bind chelates formed between a metal ion that is a radionuclide and a chelating agent. The decay of the radionuclide is utilized to locate a region of disease, e.g., a tumor or to treat the disease through radiotherapy.

Thus, in a first aspect there is provided an antibody that has an antigen recognition domain that recognizes a macrocylic metal chelate. The macrocyclic metal chelate preferably includes four heteroatoms (e.g., O, S, N and combinations thereof) within its structure. Exemplary macrocyclic chelates include four nitrogen atoms. One of skill in the art will appreciate that the metal ion may be any lanthanide, actinide, group IIIb transition metal, alkaline earth metal, or metal so long as X does not substantially affect the binding affinity of the antibody and the metal chelate. Typically, the lanthanide is La, Ce, Pr, Nd, Sm, Eu, Gd, Th, Dy, Ho, Er, Ym, Yb, Lu, or Pm. Typically, the actinide is Ac, Pa, or Am. Typically, the group IIb transition metal is Y or Sc. Typically, the alkaline earth metal is Sr. Typically, the metal is In, Ti, or Bi. In addition, $R^2$ may comprise an amino acid side chain, e.g., Lys, Cys, Glu, or Asp.

In an exemplary embodiment, the $V_L$ chain of the antibody is not encoded by the nucleic acid sequence set forth in SEQ ID NO:1 and the $V_H$ chain of the antibody is not encoded by the nucleic acid sequence set forth in SEQ ID NO:5.

In a preferred embodiment, the antibody recognizes and binds to an array of macrocyclic metal chelates that are structurally distinct. The "promiscuity" of the antibodies of this embodiment is a unique feature of the present invention, allowing for the design of different diagnostic and treatment regimens using a single antibody or a small cohort of antibodies.

In another aspect, the invention provides a mutant antibody comprising a reactive site not present in the wildtype of said antibody and an antigen recognition domain that recognizes a macrocyclic metal chelate comprising four nitrogen atoms, wherein said reactive site is in a position proximate to or within said antigen recognition domain. The presence of the complementary reactive functional groups on the antibody and the chelate allow for the formation of a covalent bond between the antibody and the chelate, essentially forming an irreversible adduct between the antibody and chelate. By varying the pendant reactive functional group present on a chelate and/or antibody it is possible to prepare a library of chelate/antibody pairs that include functional groups exhibiting a range of reactivities. The chelate-antibody pairs of the invention are useful as analytical agents and in clinical diagnosis and therapy. When the chelate-antibody pairs are used as a clinical therapeutic or diagnostic agent, the chelate circulates throughout the body of the patient to whom it is administered prior to reaching the targeting antibody, which has been pretargeted to a tissue or other site. To assure that a useful quantity of an administered dose of the chelate reaches the target antibody, the reactive group of the reactive group on the chelate is preferably selected such that it does not react substantially with elements of, for example, blood and plasma, but readily reacts with the complementary reactive site on the antibody following the formation of an antibody-antigen (chelate) complex.

In a second aspect, the invention provides a composition having the structure:

$$(Ab)_{n'}\text{-L-T}$$

wherein n' is an integer from 1-10. The symbol Ab represents an antibody of the invention. The symbol L represents a chemical bond or linking group that may contain one or more functional groups; and T is a targeting moiety.

For purposes of illustration, the invention is described further by reference to an exemplary antibody-chelate pair. The description is for clarity of illustration, and is not intended to define or limit the scope of the present invention.

In an exemplary embodiment, a reactive site is incorporated into an anti-chelate antibody by engineering a cysteine at one of several locations that are near to the region of the antibody to which the chelate binds. The engineering is typically accomplished by site-directed mutagenesis of a nucleic acid encoding the wild-type of the anti-chelate antibody. The resulting mutant antibodies comprise a library of single-Cys mutants. Mutated antibodies, such as the single-Cys mutants can be prepared using methods that are now routine in the art (see, for example, Owens et al., *Proceedings of the National Academy of Sciences USA* 95: 6021-6026 (1998); Owens et al., *Biochemistry* 37: 7670-7675 (1998)). The library members are then tested against a library of electrophilic chelates, differing in structure and reactivity, to determine the best pairs for further study. As discussed above, the electrophilic chelates preferably do not react prematurely with nucleophiles normally present in the blood. The reactivity of the chelates with physiologically relevant groups is easily determined in vitro. In the present example, in which the nucleophile is the cysteine —SH group, important potentially interfering groups are, for example, thiols on glutathione and other small molecules, and cysteine in albumin (Geigy Scientific Tables Vol. 3, C. Lentner, ed., Ciba-Geigy Ltd., Basel, Switzerland 1984). The mildly electrophilic groups on alkylating agents used in cancer chemotherapy (nitrogen mustards, ethyleneimine derivatives, mesylate esters, etc.) provide guidance concerning the practical limits of reactivity.

In a third aspect, the present invention provides a mutant antibody comprising a reactive cysteine residue that is not present in the wild-type of the antibody. The antibody also includes an antigen recognition domain that specifically binds to a metal chelate against which the antibody is raised. The reactive —SH of the cysteine is in a position proximate to or within the antigen recognition domain, such that the —SH group and the pendant reactive group on the antibody are able to form a covalent bond.

Because of the high local concentrations of nucleophile and electrophile in the antibody-hapten (chelate) complex, weaker electrophiles than those found on anticancer drugs are preferred. As discussed by Fersht, the effect of local concentration can be appreciated by comparing rate constants for the same chemical reaction between two separate reactants, and between two reactive groups joined by a linker (Alan Fersht, Enzyme Structure and Mechanism, 2nd Ed., Freeman, N.Y., 1985, pp. 56-63). The effect of high local concentration is displayed schematically in Scheme 1:

Scheme 1

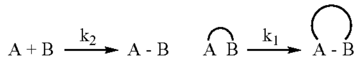

in which effective local concentration of A in the presence of B in the unimolecular reaction=$k_1/k_2$.

Fersht cites examples in which the effective local concentration defined in this way is enormous (e.g., >$10^5$ M). The enormous effective local concentrations leads to the insight that a hapten bearing a weakly reactive electrophile can diffuse intact through a dilute solution of nucleophiles, and still bind to the antibody antigen recognition domain and undergo attack by a nucleophilic sidechain of the antibody.

In addition to the antibodies and antibody-chelate pairs of the invention, in a fourth aspect, there is also provided a method of using the compositions of the invention to treat a patient for a disease or condition or to diagnose the disease or condition. The method comprises the steps of: (a) administering to the patient an antibody comprising; (i) a antigen recognition domain that specifically binds to the metal chelate; and (ii) a targeting moiety that binds specifically to a cell thereby forming a complex between the antibody and the cell. The binding of antibody to the cell can be mediated by any cell surface structure, for example, cell surface receptors and cell surface antigens. Following step (a), the metal chelate is administered to the patient and the chelate and the antibody bind to form a antibody-antigen (chelate) pair.

In some embodiments, the antibody is a mutant antibody comprising a reactive site not present in the wild-type of the antibody (with the reactive site in a position proximate to or within the antigen recognition domain) and the metal chelate comprises a pendant reactive functional group having a reactivity complementary to the reactivity of the reactive site of the antibody. The chelate and the mutant antibody bind to form an antibody-antigen (chelate) pair, the reactive groups of which subsequently react to form an irreversible bond (i.e., a bond that remains essentially permanent under physiologically relevant conditions) between the antibody and the antigen.

In addition to the method described above, the present invention also provides a method in which the tissue is pretargeted with the antibodies described herein. In this aspect, the method comprises the steps of: (a) administering to a patient an antibody of the invention, i.e., an antibody that has an antigen recognition domain that recognizes a macrocyclic metal chelate. In some embodiments, the antibody comprises a targeting moiety that binds specifically to a component or structure on the cell surface, thereby forming a complex between the cell and the antibody. The binding of antibody to the cell can be mediated by any cell surface structure, for example, cell surface receptors and cell surface antigens. Following step (a), the metal chelate is administered to the patient. The chelate specifically binds to the antibody forming an antibody-antigen complex.

In some embodiments, the antibody is a mutant antibody comprising a reactive site not present in the wild-type of the antibody, wherein the reactive site is in a position proximate to or within the antigen recognition domain and the metal chelate comprises a pendant reactive functional group having a reactivity complementary to the reactivity of the reactive site of the antibody. After the antibody-antigen complex is formed, the reactive site of the antibody and that of the metal chelate react to form a covalent bond between the antibody and the metal chelate.

The compositions and methods of the present invention are described in greater detail below.

BRIEF DESCRIPTION OF THE DRAWINGS

FIG. 1 shows the sequences for the $V_L$ chain of 2D12.5 (SEQ ID NO: 1) and the sequences for CDR1, CDR2, and CDR3 for the $V_L$ chain of 2D12.5 (SEQ ID NOS: 2, 3, and 4, respectively). FIG. 1 also shows the sequences for the $V_H$ chain (SEQ ID NO:5) and the sequences for CDR1, CDR2, and CDR3 for the $V_H$ chain of 2D12.5 (SEQ ID NOS: 6, 7, and 8, respectively).

FIG. 2 shows the alignment of the amino acid sequence of the $V_H$ chain of 2D12.5. In particular, FIG. 2 shows the alignment of the native hybridoma sequence, the native cloned hybridoma sequence, the N87D sequence, the N87D_G53C sequence, the N87D_G54C sequence, and the N87D_G55C sequence (SEQ ID NOS:9, 10, 11, 12, 13, and 14, respectively). Note that the native hybridoma sequence shown corresponds to amino acids 2-119 of the $V_H$ chain of 2D12.5 as set forth in SEQ ID NO:5. Therefore, N87D is N88D, G53C is G54C, G55C is G55C, and G55C is G56C if the Kabat standard numbering system is used to determine the positions of amino acid residues in an antibody heavy chain or light chain (see, e.g., Kabat et al., *Sequences of Proteins of Immunological Interest* 5th Ed., NIH Publication No. 91-3242 (1991)).

FIG. 3 shows the alignment of the nucleotide sequence of the $V_H$ chain of 2D12.5. In particular, FIG. 3 shows the alignment of the native hybridoma sequence, the native cloned hybridoma sequence, the N87D sequence, the N87D_G53C sequence, the N87D_G54C sequence, and the N87D_G55C sequence (SEQ ID NOS:15, 16, 17, 18, 19, and 20, respectively).

FIG. 4 shows the alignment of the amino acid sequence of the $V_L$ chain of 2D12.5. In particular, FIG. 4 shows the alignment of the native hybridoma sequence, the native cloned hybridoma sequence, and the N53C sequence (SEQ ID NOS: 21, 22, and 23, respectively). Note that the native hybridoma sequence shown corresponds to amino acids 2-110 of the $V_L$ chain of 2D12.5 as set forth in SEQ ID NO:1. Therefore, N53C is N54C, if the Kabat standard numbering system is used.

FIG. 5 shows the alignment of the nucleotide sequence of the $V_L$ chain of 2D12.5. In particular, FIG. 5 shows the alignment of the native hybridoma sequence, the native cloned hybridoma sequence, and the N53C sequence (SEQ ID NOS: 24, 25, and 26, respectively).

FIG. 6 shows the alignment of the amino acid sequence of the chimeric $V_L$ chain of 2D12.5 fused to the $C_L$ kappa chain of a human anti-tetanus toxoid antibody. In particular, FIG. 6 shows the alignment of the native cloned hybridoma sequence fused to the $C_L$ kappa chain, the N53C $V_L$ sequence fused to the $C_L$ kappa chain, the native hybridoma sequence, and the $C_L$ kappa chain of the human anti-tetanus toxoid antibody template for gene assembly (SEQ ID NOS:27, 28, 29 and 30, respectively).

FIG. 7 shows the alignment of the nucleotide sequence of the chimeric $V_L$ chain of 2D12.5 fused to the $C_L$ kappa chain of a human anti-tetanus toxoid antibody. In particular, FIG. 7 shows the alignment of the native cloned hybridoma sequence fused to the $C_L$ kappa chain, the N53C $V_L$ sequence fused to the $C_L$ kappa chain, the native $V_L$ hybridoma sequence, and the $C_L$ kappa chain of the human anti-tetanus toxoid antibody template for gene assembly (SEQ ID NOS: 31, 32, 33, and 34, respectively).

FIG. 8 shows the alignment of the amino acid sequence of the chimeric $V_H$ chain of 2D12.5 fused to the CH1 chain of a human anti-tetanus toxoid antibody. In particular, FIG. 8 shows the alignment of the native cloned hybridoma sequence fused to the CH1 chain, the N87D $V_H$ sequence fused to the CH1 chain, the N87D_G53C $V_H$ sequence fused to the CH1 chain, the N87D_G54C $V_H$ sequence fused to the CH1 chain, and the N87D_G55C $V_H$ sequence fused to the CH1 chain, the $V_H$ chain of 2D12.5 fused to the CH1 chain expected sequence, and the native $V_H$ hybridoma sequence, (SEQ ID NOS:35, 36, 37, 38, 39, 40, and 41, respectively).

FIG. 9 shows the alignment of the nucleotide sequence of the chimeric $V_H$ chain of 2D12.5 fused to the CH1 chain of a human anti-tetanus toxoid antibody. In particular, FIG. 9 shows the alignment of the native cloned hybridoma sequence fused to the CH1 chain, the N87D $V_H$ sequence fused to the CH1 chain, the N87D_G53C $V_H$ sequence fused to the CH1 chain, the N87D_G54C $V_H$ sequence fused to the $V_H$ chain of 2D12.5 fused to the CH1 chain, and the N87D_G55C $V_H$ sequence fused to the CH1 chain, the CH1 chain expected sequence, and the native $V_H$ hybridoma sequence, (SEQ ID NOS:42, 43, 44, 45, 46, 47, and 48, respectively).

FIG. 10D PCR Reaction Primers=SEQ ID NOS:57-63.

FIG. 11D PCR Reaction Primers=SEQ ID NOS:57, 69, 70, 71 and 63.

DEFINITIONS

Figure 10D:
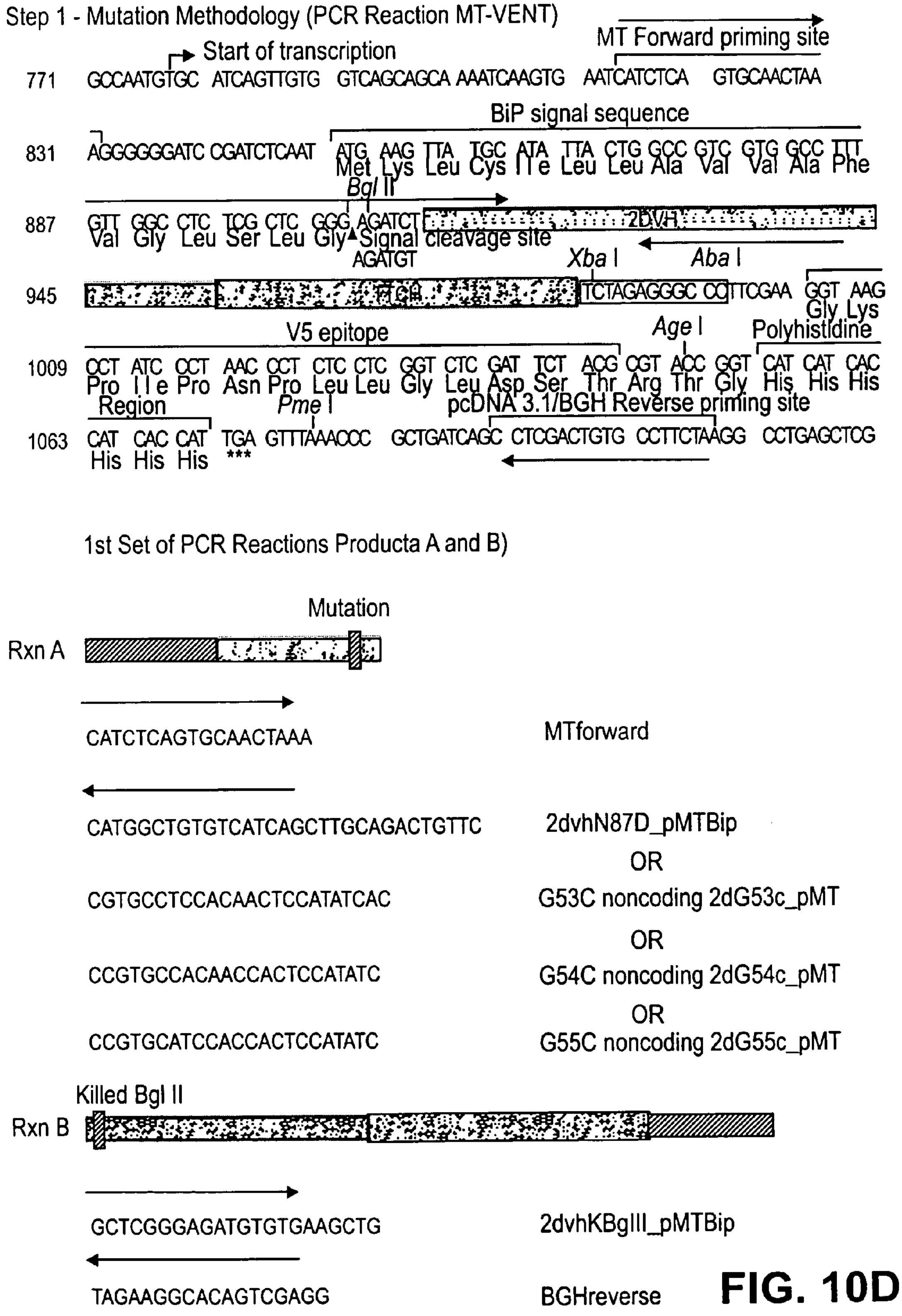
FIG. 10D Mutation Methodology sequencess=SEQ ID NOS: 53-56.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

"Antibody" refers to a polypeptide encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition, i.e., an antigen recognition domain. As used herein, "antigen recognition domain" means that part of the antibody, recombinant molecule, the fusion protein, or the immunoconjugate of the invention which recognizes the target or portions thereof. Typically the antigen recognition domain comprises the variable region of the antibody or a portion thereof, e.g., one, two, three, four, five, six, or more hypervariable regions. The terms "$V_H$" or "VH" refer to the variable region of an immunoglobulin heavy chain, including an Fv, scFv, dsFv or Fab. The terms "$V_L$" or "VL" refer to the variable region of an immunoglobulin light chain, including an Fv, scFv, dsFv or Fab.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). Thus, the term antibody, as used herein, also includes antibody fragments either produced by the modification of whole antibodies.

As used herein, "fragment" is defined as at least a portion of the variable region of the immunoglobulin molecule, which binds to its target, i.e. the antigen recognition domain or the antigen binding region. Some of the constant region of the immunoglobulin may be included. Examples of antibody functional fragments include, but are not limited to, complete antibody molecules, humanized antibodies, antibody fragments, such as Fv, single chain Fv (scFv), hypervariable regions ro complementarity determining regions (CDRs), $V_L$ (light chain variable region), $V_H$ (heavy chain variable region), Fab, F(ab)2' and any combination of those or any other portion of an immunoglobulin peptide capable of binding to target antigen (see, e.g., Fundamental Immunology (Paul ed., 4th. 1999). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) Nature 348:552). The term antibody also includes bivalent or bispecific molecules, diabodies, triabodies, and tetrabodies. Bivalent and bispecific molecules are described in, e.g., Kostelny et al., *J. Immunol.* 148: 1547 (1992), Pack and Pluckthun, *Biochemistry* 31: 1579 (1992), Zhu et al. *Protein Sci.* 6: 781 (1997), Hu et al. *Cancer Res.* 56: 3055 (1996), Adams et al., *Cancer Res.* 53: 4026 (1993), and McCartney, et al., *Protein Eng.* 8: 301 (1995).

A "humanized antibody" refers to an antibody in which the antigen binding loops, i.e., complementarity determining regions (CDRs), comprised by the $V_H$ and $V_L$ regions are grafted to a human framework sequence. Typically, the humanized antibodies have the same binding specificity as the non-humanized antibodies described herein. Techniques for humanizing antibodies are well known in the art and are described in e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al., *Nature* 321: 522 (1986); and Verhoyen et al., *Science* 239: 1534 (1988). Humanized antibodies are further described in, e.g., Winter and Milstein, *Nature* 349: 293 (1991).

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Rossolini et al.

(1994) Mol. Cell. Probes 8:91-98). The term nucleic acid is used interchangeably with gene, cDNA, mRNA, oligonucleotide, and polynucleotide.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99% or higher, compared to a reference sequence using the programs described herein, preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like. "Substantial identity" of amino acid sequences for these purposes normally means that a polypeptide comprises a sequence that has at least 40% sequence identity to the reference sequence. Preferred percent identity of polypeptides can be any integer from 40% to 100%. More preferred embodiments include at least 60%, 65%, 70%, 75%, 80%, 85%, 90%, 95%, or 99%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Optimal alignment of sequences for comparison may be conducted by the local identity algorithm of Smith and Waterman (1981) Add. APL. Math. 2:482, by the identity alignment algorithm of Needleman and Wunsch (1970) J. Mol. Biol. 48:443, by the search for similarity method of Pearson and Lipman (1988) Proc. Natl. Acad. Sci. U.S.A. 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

A preferred example of algorithms that are suitable for determining percent sequence identity and sequence similarity are the BLAST and BLAST 2.0 algorithms, which are described in Altschul et al. (1977) Nuc. Acids Res. 25:3389-3402 and Altschul et al. (1990) J. Mol. Biol. 215:403-410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both Another indication that nucleotide sequences are substantially identical is if two molecules hybridize to each other, or to a third nucleic acid, under moderately, and preferably highly, stringent conditions. Stringent conditions are sequence dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

For the purpose of the invention, suitable "moderately stringent conditions" include, for example, prewashing in a solution of 5×SSC, 0.5% SDS, 1.0 mM EDTA (pH 8.0), hybridizing at 50° C.-65° C., 5×SSC overnight, followed by washing twice at 65° C. for 20 minutes with each of 2×, 0.5× and 0.2×SSC (containing 0.1% SDS). Such hybridizing DNA sequences are also within the scope of this invention. As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore or another moiety.

"Peptide," "polypeptide" or "protein" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983). The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups alos include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2,—S(O)—CH_3$, $—CH_2—CH_2—S(O)_2—CH_3$, $—CH=CH—O—CH_3$, $—Si(CH_3)_3$, $—CH_2—CH=N—OCH_3$, and $—CH=CH—N(CH_3)—CH_3$. Up to two heteroatoms may be consecutive, such as, for example, $—CH_2—NH—OCH_3$ and $—CH_2—O—Si(CH_3)_3$. Similarly, the term "heteroalkylene" by itself or as part of another substituent means a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R" R'", —OC(O)R', —C(O)R', —$CO_2$R', —CONR'R", —OC(O)NR'R", —NR"C(O)R', —NR'—C(O)NR"R'", —NR"$C(O)_2$R', —NR—C(NR'R" R'")=NR"", —NR—C(NR'R")=NR'", —S(O)R', —$S(O)_2$R', —$S(O)_2$NR'R", —$NRSO_2$R', —CN and —$NO_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R" R'", —OC(O)R', —C(O)R', —$CO_2$R', —CONR'R", —OC(O)NR'R", —NR"C(O)R', —NR'—C(O)NR"R'", —NR"$C(O)_2$R', —NR—C(NR'R" R'")=NR"", —NR—C(NR'R")=NR'", —S(O)R', —$S(O)_2$R', —$S(O)_2$NR'R", —$NRSO_2$R', —CN and —$NO_2$, —R', —$N_3$, —$CH(Ph)_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R'" and R"" groups when more than one of these groups is present.

The symbol ∿∿∿, whether utilized as a bond or displayed perpendicular to a bond indicates the point at which the displayed moiety is attached to the remainder of the molecule, solid support, etc.

"Non-covalent protein binding groups" are moieties that interact with an intact or denatured polypeptide in an associative manner. The interaction may be either reversible or irreversible in a biological milieu, i.e., under physiologically relevant conditions. The incorporation of a "non-covalent protein binding group" into a chelating agent or complex of the invention provides the agent or complex with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, sulfonate, thiosulfate, and thiosulfonate.

The term "targeting moiety" is intended to mean a moiety that is (1) able to direct the entity to which it is attached (e.g., therapeutic agent or marker) to a target cell, for example to a specific type of tumor cell or (2) is preferentially activated at a target tissue, for example a tumor. The targeting group can be a small molecule, which is intended to include both non-peptides and peptides. The targeting group can also be a macromolecule, which includes saccharides, lectins, receptors, ligand for receptors, proteins such as BSA, antibodies, bispecific antibodies, and so forth.

As used herein, an "immunoconjugate" means any molecule or ligand such as an antibody or growth factor (i.e., hormone) chemically or biologically linked to a cytotoxin, a radioactive agent, an anti-tumor drug or a therapeutic agent. The antibody or growth factor may be linked to the cytotoxin, radioactive agent, anti-tumor drug or therapeutic agent at any location along the molecule so long as the antibody is able to bind its target. Examples of immunoconjugates include immunotoxins and antibody conjugates.

As used herein, "selectively killing" means killing those cells to which the antibody binds.

As used herein, examples of "carcinomas" include bladder, breast, colon, larynx, liver, lung, ovarian, pancreatic, rectal, skin, spleen, stomach, testicular, thyroid, and vulval carcinomas.

As used herein, an "effective amount" is an amount of the antibody, immunoconjugate, which selectively kills cells or selectively inhibits the proliferation thereof.

As used herein, "therapeutic agent" means any agent useful for therapy including anti-tumor drugs, cytotoxins, cytotoxin agents, and radioactive agents.

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), interferons and radioactive agents.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, "a radioactive agent" includes any radioactive agent (e.g., α, β, or γ emitters), which is effective in destroying a tumor. Examples include, but are not limited to, $Bi^{213}$, $Ac^{225}$, $Y^{90}$, $Lu^{177}$, $Am^{241}$, $I^{125}$. Additionally, naturally occurring radioactive elements such as uranium, radium, and thorium, which typically represent mixtures of radioisotopes, are suitable examples of a radioactive agent.

As used herein, "administering" means oral administration, administration as a suppository, topical contact, intravenous, intraperitoneal, intramuscular, intralesional or subcutaneous administration, or the implantation of a slow-release device e.g., a miniosmotic pump, to the subject.

As used herein, "cell surface antigens" means any cell surface antigen which is generally associated with cells involved in a pathology (e.g., tumor cells), i.e., occurring to a greater extent as compared with normal cells. Such antigens may be tumor specific. Alternatively, such antigens may be found on the cell surface of both tumorigenic and non-tumorigenic cells. These antigens need not be tumor specific. However, they are generally more frequently associated with tumor cells than they are associated with normal cells.

As used herein, "tumor targeted antibody" means any antibody, which recognizes cell surface antigens on tumor (i.e., cancer) cells. Although such antibodies need not be tumor specific, they are tumor selective, i.e. bind tumor cells more so than it does normal cells.

As used herein, "pharmaceutically acceptable carrier" includes any material which when combined with the antibody retains the antibody's immunogenicity and non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

DETAILED DESCRIPTION OF THE INVENTION AND THE PREFERRED EMBODIMENTS

The present invention provides compositions for delivering therapeutic and diagnostic agents directly to cells involved in a disease or other pathology. The compositions of the invention include reactive therapeutic or diagnostic species and reactive antibodies that specifically bind the therapeutic or diagnostic species and, subsequent to the specific binding event, form a covalent bond via the reactive site of the antibody and the pendant reactive functional group of the therapeutic or diagnostic species. Also provided are methods of treating a patient using the compounds described herein.

The present invention is illustrated by reference to the use of reactive metal chelates as an exemplary embodiment. The use of metal chelates to illustrate the concept of the invention is not intended to define or limit the scope of the invention. Those of skill in the art will readily appreciate that the concepts underlying the compositions and methods described herein are equally applicable to any therapeutic or diagnostic agent to which an antibody can be raised (e.g., antitumor drugs, cytotoxins, etc.).

A. The Compositions

In a first aspect, the present invention provides an antibody comprising an antigen recognition domain that specifically binds to a metal chelate. In some embodiments, the antibody is a mutant antibody comprising a reactive site that is not present in the wild-type of the antibody. The reactive site of the mutant antibody is in a position proximate to or within the antigen recognition domain, such that the chelate and the antibody are able to form an irreversible bond.

1. The Antibodies

The present invention provides antibodies that specifically bind to reactive metal chelates. For preparation of monoclonal or polyclonal antibodies, any technique known in the art can be used (see, e.g., Kohler & Milstein, *Nature* 256: 495-497 (1975); Kozbor et al., *Immunology Today* 4: 72 (1983); Cole et al., pp. 77-96 in MONOCLONAL ANTIBODIES AND CANCER THERAPY, Alan R. Liss, Inc. (1985)).

Methods of producing of polyclonal antibodies are known to those of skill in the art. In an exemplary method, an inbred strain of mice (e.g., BALB/C mice) or rabbits is immunized with the chelate or a close structural analogue using a standard adjuvant, such as Freund's adjuvant, and a standard immunization protocol. Alternatively, or in addition to the use of an adjuvant, the chelate is coupled to a carrier that is itself immunogenic (e.g., keyhole limpit hemocyanin ("KLH"). The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired.

Monoclonal antibodies are obtained by various techniques familiar to those skilled in the art. Briefly, spleen cells from an animal immunized with a desired antigen are immortalized, commonly by fusion with a myeloma cell (see, for example, Kohler & Milstein, *Eur. J. Immunol.* 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246: 1275-1281 (1989).

Monoclonal antibodies and polyclonal sera are collected and titered against the immunogen in an immunoassay, for example, a solid phase immunoassay with the immunogen immobilized on a solid support. Typically, polyclonal antisera with a titer of $10^4$ or greater are selected and tested for cross reactivity against different chelates, using a competitive binding immunoassay. Specific polyclonal antisera and monoclonal antibodies will usually bind with a $K_d$ of at least about 0.1 mM, more usually at least about 1 μM, preferably, at least about 0.1 μM or better, and most preferably, 0.01 μM or better.

Techniques for the production of single chain antibodies (U.S. Pat. No. 4,946,778) can be adapted to produce antibodies to reactive chelates and other diagnostic, analytical and therapeutic agents. Also, transgenic mice, or other organisms such as other mammals, may be used to express humanized antibodies. Alternatively, phage display technology can be used to produce and identify antibodies and heteromeric Fab fragments that specifically bind to selected antigens (see, e.g., McCafferty et al., *Nature* 348: 552-554 (1990); Marks et al., *Biotechnology* 10: 779-783 (1992)).

In an exemplary embodiment, an animal, such as a rabbit or mouse is immunized with a chelate, or an immunogenic construct. The antibodies produced as a result of the immunization are preferably isolated using standard methods.

In a still further preferred embodiment, the antibody is a humanized antibody. "Humanized" refers to a non-human polypeptide sequence that has been modified to minimize immunoreactivity in humans, typically by altering the amino acid sequence to mimic existing human sequences, without substantially altering the function of the polypeptide sequence (see, e.g., Jones et al., *Nature* 321: 522-525 (1986), and published UK patent application No. 8707252).

In another preferred embodiment, the present invention provides an antibody, as described above, further comprising a member selected from detectable labels, biologically active agents and combinations thereof attached to the antibody.

When the antibody is conjugated to a detectable label, the label is preferably a member selected from the group consisting of radioactive isotopes, fluorescent agents, fluorescent agent precursors, chromophores, enzymes and combinations thereof. Methods for conjugating various groups to antibodies are well known in the art. For example, a detectable label that is frequently conjugated to an antibody is an enzyme, such as horseradish peroxidase, alkaline phosphatase, β-galactosidase, and glucose oxidase.

In an exemplary embodiment of the present invention, horseradish peroxidase is conjugated to an antibody raised against a reactive chelate. In this embodiment, the saccharide portion of the horseradish peroxidase is oxidized by periodate and subsequently coupled to the desired immunoglobin via reductive amination of the oxidized saccharide hydroxyl groups with available amine groups on the immunoglobin.

Methods of producing antibodies labeled with small molecules, for example, fluorescent agents, are well known in the art. Fluorescent labeled antibodies can be used in immunohistochemical staining (Osborn et al., *Methods Cell Biol.* 24: 97-132 (1990); in flow cytometry or cell sorting techniques (Ormerod, M. G. (ed.), FLOW CYTOMETRY. A PRACTICAL APPROACH, IRL Press, New York, 1990); for tracking and localization of antigens, and in various double-staining methods (Kawamura, A., Jr., FLUORESCENT ANTIBODY TECHNIQUES AND THEIR APPLICATION, Univ. Tokyo Press, Baltimore, 1977).

Many reactive fluorescent labels are available commercially (e.g., Molecular Probes, Eugene, Oreg.) or they can be synthesized using art-recognized techniques. In an exemplary embodiment, an antibody of the invention is labeled with an amine-reactive fluorescent agent, such as fluorescein isothiocyanate under mildly basic conditions. For other examples of antibody labeling techniques, see, Goding, *J. Immunol. Methods* 13: 215-226 (1976); and in, MONOCLONAL ANTIBODIES: PRINCIPLES AND PRACTICE, pp. 6-58, Academic Press, Orlando (1988).

In some embodiments, the antibodies are mutant antibodies that comprise a reactive site that is not present in the wild type antibody. In an exemplary embodiment, the reactive site is the mutation. Prior to constructing the mutagenized antibodies of the invention, it is often useful to prepare the wild-type anti-chelate antibody from an isolated nucleic acid encoding an antibody or a portion of an antibody of the invention. In a further preferred embodiment, the antibody fragment is an $F_v$ fragment. $F_v$ fragments of antibodies are heterodimers of antibody $V_H$ (variable region of the heavy chain) and $V_L$ domains (variable region of the light chain). They are the smallest antibody fragments that contain all structural information necessary for specific antigen binding. $F_v$ fragments are useful for diagnostic and therapeutic applications such as imaging of tumors or targeted cancer therapy. In particular, because of their small size, $F_v$ fragments are useful in applications that require good tissue or tumor penetration, because small molecules penetrate tissues much faster than large molecules (Yokota et al., *Cancer Res.,* 52: 3402-3408 (1992)).

The heterodimers of heavy and light chain domains that occur in whole IgG, for example, are connected by a disulfide bond, but $F_v$ fragments lack this connection. Although native unstabilized $F_v$ heterodimers have been produced from unusual antibodies (Skerra et al., *Science,* 240: 1038-1041 (1988); Webber et al., *Mol. Immunol.* 4: 249-258 (1995), generally $F_v$ fragments by themselves are unstable because the $V_H$ and $V_L$ domains of the heterodimer can dissociate (Glockshuber et al., *Biochemistry* 29: 1362-1367 (1990)). This potential dissociation results in drastically reduced binding affinity and is often accompanied by aggregation.

Solutions to the stabilization problem have resulted from a combination of genetic engineering and recombinant protein expression techniques. Such techniques are of use in constructing the antibodies of the present invention. The most common method of stabilizing $F_v$s is the covalent connection of $V_H$ and $V_L$ by a flexible peptide linker, which results in single chain $F_v$ molecules (see, Bird et al., *Science* 242: 423-426 (1988); Huston et al., *Proc. Natl. Acad. Sci. USA* 16: 5879-5883 (1988)). The single chain $F_v$s ($scF_v$s) are generally more stable than $F_v$s alone.

Another way to generate stable recombinant $F_v$s is to connect $V_H$ and $V_L$ by an interdomain disulfide bond instead of a linker peptide; this technique results in disulfide stabilized $F_v$, ($dsF_v$). The $dsF_v$s solve many problems that can be associated with $scF_v$s: they are very stable, often show full antigen binding activity, and sometimes have better affinity than $scF_v$s (Reiter et al., *Int. Cancer* 58: 142-149 (1994)). Thus, in another preferred embodiment, the antibody of the invention is a $scF_v$s Peptide linkers, such as those used in the expression of recombinant single chain antibodies, may be employed as the linkers and connectors of the invention. Peptide linkers and their use are well known in the art. (See, e.g., Huston et al., 1988; Bird et al., 1983; U.S. Pat. No. 4,946,778; U.S. Pat. No. 5,132,405; and Stemmer et al., Biotechniques 14:256-265 (1993)). The linkers and connectors are flexible and their sequence can vary. Preferably, the linkers and connectors are long enough to span the distance between the amino acids to be joined without putting strain on the structure. For example, the linker $(Gly_4Ser)_3$ (SEQ ID NO:72) is a useful linker because it is flexible and without a preferred structure (Freund et al., *Biochemistry* 33: 3296-3303 (1994)).

After the stabilized immunoglobin has been designed, a gene encoding at least $F_v$ or a fragment thereof is constructed. Methods for isolating and preparing recombinant nucleic acids are known to those skilled in the art (see, Sambrook et al., *Molecular Cloning. A Laboratory Manual* (2d ed. 1989); Ausubel et al., *Current Protocols in Molecular Biology* (1995)).

The present invention provides for the expression of nucleic acids corresponding to the wild-type of essentially any antibody that can be raised against a metal chelate, and the modification of that antibody to include a reactive site. In a preferred embodiment, the Fab heavy chain of the wild-type antibody is the amino acid sequence set forth in SEQ ID NO:5 (FIG. 1) or is encoded by the nucleic acid sequence set forth in SEQ ID NO:16 (FIG. 3). In another preferred embodiment, the light-chain of the wild-type antibody is the amino acid sequence set forth in SEQ ID NO:1 (FIG. 1) or is encoded by the nucleic acid sequence set forth in SEQ ID NO:25 (FIG. 5). In yet another preferred embodiment, the invention provides a mutant of the light chain of 2D12.5 in which N-53 is substituted by C and that has the amino acid sequence set forth in SEQ ID NO:23 (FIG. 4), or is encoded by the nucleic acid sequence set forth in SEQ ID NO:26 (FIG. 5). In yet another preferred embodiment, the invention provides a mutant of the heavy-chain of 2D12.5 in which N-87 is replaced by D and that has the amino acid sequence set forth in SEQ ID NO:11 (FIG. 2) or is encoded by the nucleic acid sequence set forth in SEQ ID NO:17 (FIG. 3). In yet another preferred embodiment, the invention provides a mutant of the heavy-chain of 2D12.5 in which N-87 is replaced by D and G-53 is replaced by C, and that has the amino acid sequence set forth in SEQ ID NO:12 (FIG. 2) or is encoded by the nucleic acid sequence set forth in SEQ ID NO:18 (FIG. 3). In yet another preferred embodiment, the invention provides a mutant of the heavy-chain of 2D12.5 in which N-87 is replaced by D and G-54 is replaced by C, and that has the amino acid sequence set forth in SEQ ID NO:13 (FIG. 2) or is encoded by the nucleic acid sequence set forth in SEQ ID NO:19 (FIG. 3). In yet another preferred embodiment, the invention provides a mutant of the heavy-chain of 2D12.5 in which N-87 is replaced by D and G-55 is replaced by C, and that has the amino acid sequence set forth in SEQ ID NO:14 (FIG. 2) or is encoded by the nucleic acid sequence set forth in SEQ ID NO:20 (FIG. 3).

Those of skill in the art will understand that substituting selected codons from the above-recited sequences with equivalent codons is within the scope of the invention. Oligonucleotides that are not commercially available are preferably chemically synthesized according to the solid phase phosphoramidite triester method first described by Beaucage & Caruthers, *Tetrahedron Letts.* 22: 1859-1862 (1981), using an automated synthesizer, as described in Van Devanter et. al., *Nucleic Acids Res.* 12: 6159-6168 (1984). Purification of oligonucleotides is preferably by either native acrylamide gel electrophoresis or by anion-exchange HPLC as described in Pearson & Reanier, *J. Chrom.* 255: 137-149 (1983).

The sequence of the cloned genes and synthetic oligonucleotides can be verified after cloning using art-recognized methods, e.g., the chain termination method for sequencing double-stranded templates of Wallace et al., *Gene* 16: 21-26 (1981).

One preferred method for obtaining specific nucleic acid sequences combines the use of synthetic oligonucleotide primers with polymerase extension or ligation on a mRNA or DNA template. Such a method, e.g., RT, PCR, or LCR, amplifies the desired nucleotide sequence, which is often known (see, U.S. Pat. Nos. 4,683,195 and 4,683,202). Restriction endonuclease sites can be incorporated into the primers. Amplified polynucleotides are purified and ligated into an appropriate vector. Alterations in the natural gene sequence can be introduced by techniques such as in vitro mutagenesis and PCR using primers that have been designed to incorporate appropriate mutations.

A particularly preferred method of constructing the immunoglobulin is by overlap extension PCR. In this technique, individual fragments are first generated by PCR using primers that are complementary to the immunoglobulin sequences of choice. These sequences are then joined in a specific order using a second set of primers that are complementary to "overlap" sequences in the first set of primers, thus linking the fragments in a specified order. Other suitable $F_v$ fragments can be identified by those skilled in the art.

The immunoglobulin, e.g., $F_v$, is inserted into an "expression vector," "cloning vector," or "vector." Expression vectors can replicate autonomously, or they can replicate by being inserted into the genome of the host cell. Often, it is desirable for a vector to be usable in more than one host cell, e.g., in *E. coli* for cloning and construction, and in a mammalian cell for expression. Additional elements of the vector can include, for example, selectable markers, e.g., tetracycline resistance or hygromycin resistance, which permit detection and/or selection of those cells transformed with the desired polynucleotide sequences (see, e.g., U.S. Pat. No. 4,704,362). The particular vector used to transport the genetic information into the cell is also not particularly critical. Any suitable vector used for expression of recombinant proteins host cells can be used.

Expression vectors typically have an expression cassette that contains all the elements required for the expression of the polynucleotide of choice in a host cell. A typical expression cassette contains a promoter operably linked to the polynucleotide sequence of choice. The promoter used to direct expression of the nucleic acid depends on the particular application, for example, the promoter may be a prokaryotic or eukaryotic promoter depending on the host cell of choice. The promoter is preferably positioned about the same distance from the heterologous transcription start site as it is from the transcription start site in its natural setting. As is known in the art, however, some variation in this distance can be accommodated without loss of promoter function.

Promoters include any promoter suitable for driving the expression of a heterologous gene in a host cell, including those typically used in standard expression cassettes. In addition to the promoter, the recombinant protein gene will be operably linked to appropriate expression control sequences for each host. For *E. coli* this includes a promoter such as the T7, trp, tac, lac or lambda promoters, a ribosome binding site, and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The vectors can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes. One of skill in the art will appreciate that vectors comprising DNA encoding the $V_L$ chain of an antibody and vectors comprising DNA encoding the $V_H$ chain of an antibody can conveniently be separately transfected into different host cells. Alternately vectors comprising DNA encoding the $V_L$ chain of an antibody and vectors comprising DNA encoding the $V_H$ chain of an antibody may be cotransfected into the same host cells.

The wild-type antichelate-antibodies can be expressed in a variety of host cells, including *E. coli*, other bacterial hosts, yeast, and various higher eukaryotic cells such as the COS, CHO, and HeLa cells lines and myeloma cell lines. Methods for refolding single chain polypeptides expressed in bacteria such as *E. coli* have been described, are well-known and are applicable to the wild-type anti-chelate polypeptides. (See, e.g., Buchner et al., *Analytical Biochemistry* 205: 263-270 (1992); Pluckthun, *Biotechnology* 9: 545 (1991); Huse et al., *Science* 246: 1275 (1989) and Ward et al., *Nature* 341: 544 (1989)).

In a preferred embodiment, the present invention provides a polypeptide that is essentially homologous to the $V_L$ sequence of 2D12.5, with the exception that asparagine-53 is replaced with a cysteine (position 54, if the Kabat standard numbering system is used) (FIG. 4).

In another preferred embodiment, the present invention provides a polypeptide that is essentially homologous to the $V_H$ sequence of 2D12.5, with the exception that aspargine-87 is replaced with a aspartic acid, and the asparagine-53 is replaced with cysteine, the asparagine-54 is replaced with cysteine, or the asparagine-55 is replaced with cysteine (FIG. 5).

Often, functional protein from *E. coli* or other bacteria is generated from inclusion bodies and requires the solubilization of the protein using strong denaturants, and subsequent refolding. In the solubilization step, a reducing agent must be present to dissolve disulfide bonds as is well-known in the art. Renaturation to an appropriate folded form is typically accomplished by dilution (e.g. 100-fold) of the denatured and reduced protein into refolding buffer.

Once expressed, the recombinant proteins can be purified according to standard procedures of the art, including ammonium sulfate precipitation, affinity columns, column chromatography, and the like (see, generally, Scopes, Protein Purification (1982)). Substantially pure compositions of at least about 90 to 95% homogeneity are preferred, and those of 98 to 99% or more homogeneity are most preferred for pharmaceutical uses. Once purified, partially or to homogeneity as desired, the polypeptides may then be used therapeutically and diagnostically.

a. Bispecific Antibodies

In another preferred embodiment, the present invention provides for a reactive antibody that is bispecific for both a metal chelate and a targeting reagent or a target tissue, such as a tumor. Bispecific antibodies (BsAbs) are antibodies that have binding specificities for at least two different antigens. Bispecific antibodies can be derived from full length antibodies or antibody fragments (e.g. $F(ab')_2$ bispecific antibodies). In a preferred embodiment, the bispecific antibody recognizes a reactive $^{111}In$ chelate of the invention and a human carcinoma cell.

Methods for making bispecific antibodies are known in the art. Traditional production of full-length bispecific antibodies is based on the co-expression of two immunoglobulin heavy chain-light chain pairs, where the two chains have different specificities (Millstein and Cuello, *Nature* 305: 537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published May 13, 1993, and in Traunecker et al., *EMBO J.* 10: 3655-3659 (1991)).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies (see, for example, Suresh et al., *Methods in Enzymology* 121: 210 (1986)).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al. (*Science* 229: 81 (1985)) describe a procedure wherein intact antibodies are proteolytically cleaved to generate $F(ab')_2$ fragments. The fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the BsAb. The BsAbs produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Ex. Med., B* 217-225 (1992) describe the production of a fully humanized BsAb $F(ab')_2$ molecule. Each Fab' fragment was separately secreted from *E. coli* and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also, Rodrigues et al., *Int. J. Cancers*, (Suppl.) 7: 45-50 (1992).

Various techniques for making and isolating BsAb fragments directly from recombinant cell culture have also been described and are useful in practicing the present invention. For example, bispecific $F(ab')_2$ heterodimers have been produced using leucine zippers. Kostelny et al., *J. Immunol.,* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci.* (*USA*), 90: 6444-6448 (1993) has provided an alternative mechanism for making BsAb fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single-chain Fv (sFv) dimers has also been reported (see, Gruber et al., *J. Immunol.,* 152: 5368 (1994)). Gruber et al., designed an antibody which comprised the $V_H$ and $V_L$ domains of a first antibody joined by a 25-amino-acid-residue linker to the $V_H$ and $V_L$ domains of a second antibody. The refolded molecule bound to fluorescein and the T-cell receptor and redirected the lysis of human tumor cells that had fluorescein covalently linked to their surface.

In addition to the preparation of wild-type antibodies that specifically bind to metal chelates, the present invention provides mutant antibodies that include a reactive site within their structure. The mutant antibodies are prepared by any method known in the art, most preferably by site directed mutagenesis of a nucleic acid encoding the wild-type antibody.

b. Site-Directed Mutagenesis

The preparation of wild-type antibodies that bind to metal chelates is discussed above. The elements of the discussion above are also broadly applicable to aspects and embodiments of the invention in which site directed mutagenesis is used to produce mutant antibodies. The concept of site-directed mutagenesis as it applies to the present invention is discussed in greater detail to supplement, not to replace the discussion above.

The mutant antibodies are suitably prepared by introducing appropriate nucleotide changes into the DNA encoding the polypeptide of interest, or by in vitro synthesis of the desired mutant antibody. Such mutants include, for example, deletions from, or insertions or substitutions of, residues within the amino acid sequence of the polypeptide of interest so that it contains the proper epitope and is able to form a covalent bond with a reactive metal chelate. Any combination of deletion, insertion, and substitution is made to arrive at the final construct, provided that the final construct possesses the desired characteristics. The amino acid changes also may alter post-translational processes of the polypeptide of interest, such as changing the number or position of glycosylation sites. Moreover, like most mammalian genes, the antibody can be encoded by multi-exon genes.

For the design of amino acid sequence mutants of the antibodies, the location of the mutation site and the nature of the mutation will be determined by the specific polypeptide of interest being modified and the structure of the reactive chelate to which the antibody binds. The sites for mutation can be modified individually or in series, e.g., by: (1) substituting first with conservative amino acid choices and then with more radical selections depending upon the results achieved; (2) deleting the target residue; or (3) inserting residues of the same or a different class adjacent to the located site, or combinations of options 1-3.

A useful method for identification of certain residues or regions of the polypeptide of interest that are preferred locations for mutagenesis is called "alanine scanning mutagenesis," as described by Cunningham and Wells, *Science,* 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis is conducted at the target codon or region and the variants produced are screened for increased reactivity with a particular reactive chelate.

Amino acid sequence deletions generally range from about 1 to 30 residues, more preferably about 1 to 10 residues, and typically they are contiguous. Contiguous deletions ordinarily are made in even numbers of residues, but single or odd numbers of deletions are within the scope hereof. As an example, deletions may be introduced into regions of low homology among LFA-1 antibodies, which share the most sequence identity to the amino acid sequence of the polypeptide of interest to modify the half-life of the polypeptide. Deletions from the polypeptide of interest in areas of substantial homology with one of the binding sites of other ligands will be more likely to modify the biological activity of the polypeptide of interest more significantly. The number of consecutive deletions will be selected so as to preserve the tertiary structure of the polypeptide of interest in the affected domain, e.g., beta-pleated sheet or alpha helix.

Amino acid sequence insertions include amino- and/or carboxyl-terminal fusions ranging in length from one residue to polypeptides containing a hundred or more residues, as well as intra-sequence insertions of single or multiple amino acid residues. Intra-sequence insertions (i.e., insertions within the mature polypeptide sequence) may range generally from about 1 to 10 residues, more preferably 1 to 5, most preferably 1 to 3. Insertions are preferably made in even numbers of residues, but this is not required. Examples of insertions include insertions to the internal portion of the polypeptide of interest, as well as N- or C-terminal fusions with proteins or peptides containing the desired epitope that will result, upon fusion, in an increased reactivity with the chelate.

A third group of variants are amino acid substitution variants. These variants have at least one amino acid residue in the polypeptide molecule removed and a different residue inserted in its place. The sites of greatest interest for substitutional mutagenesis include one or two loops in antibodies. Other sites of interest are those in which particular residues of the polypeptide obtained from various species are identical among all animal species of the polypeptide of interest, this degree of conservation suggesting importance in achieving biological activity common to these molecules. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original | Substitution |
|---|---|
| Ala (A) | val; leu; ile |
| Arg (R) | lys; gln; asn |
| Asn (N) | gln; his; lys |
| Asp (D) | glu |
| Cys (C) | ser |
| Gln (Q) | asn |
| Glu (E) | asp |
| Gly (G) | pro; ala |
| His (H) | asn; gln; lys; arg |
| Ile (I) | leu; vat; met; ala |
| phe; | norleucine |
| Leu (L) | norleucine; ile; val; met; ala; phe |
| Lys (K) | arg; gln; asn |
| Met (M) | leu; phe; ile |
| Phe (F) | leu; val; ile; ala; leu |
| Pro (P) | ala |
| Ser (S) | thr |
| Thr (T) | ser |
| Trp (W) | tyr; phe |
| Tyr (Y) | trp; phe; thr; ser |
| Val (V) | ile; leu; met; phe; ala; norleucine |

In addition to the incorporation of the reactive site in the antibody structure, modifications in the function of the polypeptide of interest can be made by selecting substitutions that differ significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. Naturally occurring residues are divided into groups based on common side-chain properties:

(1) hydrophobic: norleucine, met, ala, vat, leu, ile;

(2) neutral hydrophilic: cys, ser, thr;

(3) acidic: asp, glu;

(4) basic: asn, gin, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

It also may be desirable to inactivate one or more protease cleavage sites that are present in the molecule. These sites are identified by inspection of the encoded amino acid sequence, in the case of trypsin, e.g., for an arginyl or lysinyl residue. When protease cleavage sites are identified, they are rendered inactive to proteolytic cleavage by substituting the targeted residue with another residue, preferably a basic residue such as glutamine or a hydrophilic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1-3 residues are inserted adjacent to such sites.

The nucleic acid molecules encoding amino acid sequence mutations of the antibodies of interest are prepared by a variety of methods known in the art. These methods include, but are not limited to, preparation by oligonucleotide-mediated (or site-directed) mutagenesis, PCR mutagenesis, and cassette mutagenesis of an earlier prepared variant or a non-variant version of the polypeptide on which the variant herein is based.

Oligonucleotide-mediated mutagenesis is a preferred method for preparing substitution, deletion, and insertion antibody mutants herein. This technique is well known in the art as described by Adelman et al., *DNA* 2: 183 (1983). Briefly, the DNA is altered by hybridizing an oligonucleotide encoding the desired mutation to a DNA template, where the template is the single-stranded form of a plasmid or bacteriophage containing the unaltered or native DNA sequence of the polypeptide to be varied. After hybridization, a DNA polymerase is used to synthesize an entire second complementary strand of the template that will thus incorporate the oligonucleotide primer, and will code for the selected alteration in the DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA,* 75: 5765 (1978).

The DNA template can be generated by those vectors that are either derived from bacteriophage M13 vectors (e.g., the commercially available M13 mp18 and M13 mp19 vectors are suitable), or those vectors that contain a single-stranded phage origin of replication as described by Viera et al. *Meth. Enzymol.,* 153: 3 (1987). Thus, the DNA that is to be mutated may be inserted into one of these vectors to generate single-stranded template. Production of the single-stranded template is described in Sections 4.21-4.41 of Sambrook et al., supra. Alternatively, single-stranded DNA template is generated by denaturing double-stranded plasmid (or other) DNA using standard techniques.

Mutations in the $V_H$ and $V_L$ domains may be introduced using a number of methods known in the art. These include site-directed mutagenesis strategies such as overlap extension PCR (see, e.g., Sambrook & Russell, supra; Ausubel et al., supra). Exemplary techniques and primers are provided in Examples 2 and 3.

The PCR products are subcloned into suitable cloning vectors that are well known to those of skill in the art and commercially available. Clones containing the correct size DNA insert are identified, for example, agarose gel electrophoresis. The nucleotide sequence of the heavy or light chain coding regions is then determined from double stranded plasmid DNA using the sequencing primers adjacent to the cloning site. Commercially available kits (e.g., the Sequenase® kit, United States Biochemical Corp., Cleveland, Ohio) are used to facilitate sequencing the DNA.

One of skill will appreciate that, utilizing the sequence information provided for the variable regions, nucleic acids encoding these sequences are obtained using a number of methods well known to those of skill in the art. Thus, DNA encoding the variable regions is prepared by any suitable method, including, for example, amplification techniques such as ligase chain reaction (LCR) (see, e.g., Wu & Wallace (1989) *Genomics* 4:560, Landegren, et al. (1988) *Science* 241:1077, and Barringer, et al. (1990) *Gene* 89:117), transcription amplification (see, e.g., Kwoh, et al. (1989) *Proc. Natl. Acad. Sci. USA* 86:1173), and self-sustained sequence replication (see, e.g., Guatelli, et al. (1990) *Proc. Natl. Acad. Sci. USA* 87:1874), cloning and restriction of appropriate sequences or direct chemical synthesis by methods such as the phosphotriester method of Narang, et al., (1979) *Meth. Enzymol.* 68:90; the phosphodiester method of Brown, et al., (1979) *Meth. Enzymol.* 68:109; the diethylphosphoramidite method of Beaucage, et al., (1981) *Tetra. Lett.* 22:1859; and the solid support method of U.S. Pat. No. 4,458,066.

The nucleic acid sequences that encode the single chain antibodies, or variable domains, are identified by techniques well known in the art (see, Sambrook, et al., supra). Briefly, the DNA products described above are separated on an electrophoretic gel. The contents of the gel are transferred to a suitable membrane (e.g., Hybond-N®, Amersham) and hybridized to a suitable probe under stringent conditions. The probe should comprise a nucleic acid sequence of a fragment embedded within the desired sequence.

If the DNA sequence is synthesized chemically, a single stranded oligonucleotide will result. This may be converted into double stranded DNA by hybridization with a complementary sequence, or by polymerization with a DNA polymerase using the single strand as a template. While it is possible to chemically synthesize an entire single chain Fv region, it is preferable to synthesize a number of shorter sequences (about 100 to 150 bases) that are later ligated together.

Alternatively, subsequences may be cloned and the appropriate subsequences cleaved using appropriate restriction enzymes. The fragments may then be ligated to produce the desired DNA sequence.

Nucleic acids encoding monoclonal antibodies or variable domains thereof are typically cloned into intermediate vectors before transformation into prokaryotic or eukaryotic cells for replication and/or expression. These intermediate vectors are typically prokaryote vectors, e.g., plasmids, or shuttle vectors. Isolated nucleic acids encoding therapeutic proteins comprise a nucleic acid sequence encoding a therapeutic protein and subsequences, interspecies homologues, alleles and polymorphic variants thereof.

To obtain high level expression of a cloned gene, such as those cDNAs encoding a suitable monoclonal antibody, one typically subclones the gene encoding the monoclonal antibody into an expression vector that contains a strong promoter to direct transcription, a transcription/translation terminator, and if for a nucleic acid encoding a protein, a ribosome binding site for translational initiation. Suitable promoters are well known in the art and described, e.g., in Sambrook et al., supra and Ausubel et al., supra. Eukaryotic expression systems for mammalian cells are well known in the art and are also commercially available. Kits for such expression systems are commercially available.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

The nucleic acid comprises a promoter to facilitate expression of the nucleic acid within a cell. Suitable promoters include strong, eukaryotic promoter such as, for example promoters from cytomegalovirus (CMV), mouse mammary tumor virus (MMTV), Rous sarcoma virus (RSV), and adenovirus. More specifically, suitable promoters include the promoter from the immediate early gene of human CMV (Boshart et al., (1985) *Cell* 41:521) and the promoter from the long terminal repeat (LTR) of RSV (Gorman et al., (1982) *Proc. Natl. Acad. Sci. USA* 79:6777).

For eukaryotic expression, the construct may comprise at a minimum a eukaryotic promoter operably linked to a nucleic acid operably linked to a polyadenylation sequence. The polyadenylation signal sequence may be selected from any of a variety of polyadenylation signal sequences known in the art, such as, for example, the SV40 early polyadenylation signal sequence. The construct may also include one or more introns, which can increase levels of expression of the nucleic acid of interest, particularly where the nucleic acid of interest is a cDNA (e.g., contains no introns of the naturally-occurring sequence). Any of a variety of introns known in the art may be used.

Other components of the construct may include, for example, a marker (e.g., an antibiotic resistance gene (such as an ampicillin resistance gene)) to aid in selection of cells containing and/or expressing the construct, an origin of replication for stable replication of the construct in a bacterial cell (preferably, a high copy number origin of replication), a nuclear localization signal, or other elements which facilitate production of the nucleic acid construct, the protein encoded thereby, or both.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence and signals required for efficient polyadenylation of the transcript, ribosome binding sites, and translation termination. The nucleic acid sequence may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette may also contain a transcription termination region downstream of the structural gene to provide for efficient termination. The termination region may be obtained from the same gene as the promoter sequence or may be obtained from different genes.

Some expression systems have markers that provide gene amplification such as thymidine kinase, hygromycin B phosphotransferase, and dihydrofolate reductase.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells.

Standard transfection methods are used to produce bacterial, mammalian, yeast, insect, or plant cell lines that express large quantities of the antibody or variable region domains, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the monoclonal antibody or a variable domain thereof.

After the expression vector is introduced into the cells, the transfected cells are cultured under conditions favoring expression of the monoclonal antibody or ariable domain region. The expressed protein is recovered from the culture using standard techniques known to those of skill in the art.

The monoclonal antibody or variable domain region may be purified to substantial purity by standard techniques known to those of skill in the art, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

c. Covalent Modifications of Polypeptide Variants

Covalent modifications of polypeptide variants are included within the scope of this invention. The modifications are made by chemical synthesis or by enzymatic or chemical cleavage or elaboration of the antibody of the invention. Other types of covalent modifications of the polypeptide variant are introduced into the molecule by reacting targeted amino acid residues of the polypeptide variant with an organic derivatizing agent that is capable of reacting with selected side chains or the N- or C-terminal residues.

The modifications of the antibody of the invention include the attachment of agents to, for example, enhance antibody stability, water-solubility, in vivo half-life and to target the antibody to a desired target tissue. Targeting the antibody preferably utilizes the covalent attachment of one or more moieties that recognize a structure on the surface of the cell to which the antibody is targeted. Exemplary targeting species include, but are not limited to, antibodies, hormones, lectins, and ligands for cell-surface receptors. Many methods are known in the art for derivatizing both the antibodies of the invention and useful targeting agents. The discussion that follows is illustrative of reactive groups found on the mutant antibody and on the targeting agent and methods of forming conjugates between the mutant antibody and the targeting agent. The use of homo- and hetero-bifunctional derivatives of each of the reactive functionalities discussed below to link the antibody to the targeting moiety is within the scope of the present invention.

Cysteinyl residues most commonly are reacted with agents that include α-haloacetates (and corresponding amines), such as chloroacetic acid or chloroacetamide, to give carboxymethyl or carboxyamidomethyl derivatives. Cysteinyl residues also are derivatized by reaction with bromotrifluoroketones, α-bromo-β-(5-imidozoyl)carboxylic acids, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with, for example, groups that include pyrocarbonate at pH 5.5-7.0 because this agent is relatively specific for the histidyl side chain. Para-bromophenacyl halides also are useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine site. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$, to prepare labeled proteins for use in radioimmunoassay, the chloramine T method described above being suitable.

Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl)carbodiimide or 1-ethyl-3-(4-azo-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W. H. Freeman & Co., San Francisco, pp. 79-86 (1983)), acetylation of the N-terminal amine, and amidation of any C-terminal carboxyl group.

Another type of covalent modification of the polypeptide variant included within the scope of this invention comprises altering the original glycosylation pattern of the polypeptide variant. By altering is meant deleting one or more carbohydrate moieties found in the polypeptide variant, and/or adding one or more glycosylation sites that are not present in the polypeptide variant.

Glycosylation of the antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original polypeptide variant (for O-linked glycosylation sites). For ease, the polypeptide variant amino acid sequence is preferably altered through changes at the DNA level, particularly by mutating the DNA encoding the polypeptide variant at preselected bases such that codons are generated that will translate into the desired amino acids. The DNA mutation(s) may be made using methods described above.

Another means of increasing the number of carbohydrate moieties on the antibody is by chemical or enzymatic coupling of glycosides to the polypeptide variant. These procedures are advantageous in that they do not require production of the polypeptide variant in a host cell that has glycosylation capabilities for N- or O-linked glycosylation. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston, CRC CRIT. REV. BIOCHEM., pp. 259-306 (1981).

Removal of any carbohydrate moieties present on the antibody is accomplished either chemically or enzymatically. Chemical deglycosylation requires exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the mutant antibody intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Another type of covalent modification of the polypeptide variant comprises linking the polypeptide variant to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or U.S. Pat. No. 4,179,337. The polymers are added to alter the properties of the mutant antibody or, alternatively, they serve as spacer groups between the targeting agent and the mutant antibody.

d. Preparation of the Antibody-Targeting Moiety Conjugate

The targeted antibodies of the invention are exemplified in the discussion that follows by a class of antibodies of the invention that are targeted by attachment to tissue-specific antibodies. Antibodies that are reactive with surface antigens on many human cells are known in the art. In a preferred embodiment, the targeting antibody is one that binds to human carcinoma cells. Antibody-targeting moiety conjugates can be prepared by covalent modification of the antibody and the targeting agent to link them together as described in in Hellstrom et al., U.S. Pat. No. 6,020,145, for example. Alternatively, the antibody-targeting moiety conjugates can be generated as fusion proteins.

Preparation of the immunoconjugate for the present targeting system includes attachment of an enzymatic or component (AC) to an antibody and forming a stable complex without compromising the activity of either component. An exemplary strategy involves incorporation of a protected sulfhydryl onto the AC using the heterobifunctional crosslinker SPDP (n-succinimidyl-3-(2-pyridyldithio)propionate and then deprotecting the sulfhydryl for formation of a disulfide bond with another sulfhydryl on the antibody. In another exemplary embodiment, new sulfhydryls are preferably incorporated onto a mutant antibody using SPDP. In the protected form, the SPDP generated sulfhydryls on the antibody react with the free sulfhydryls incorporated onto the AC forming the required disulfide bonds. By optimizing reaction conditions, the degree of SPDP modification of each component is controlled, thus maintaining maximum activity of each component. SPDP reacts with primary amines and the incorporated sulfhydryl is protected by 2-pyridylthione.

If SPDP should affect the activities of either the antibody (e.g., the moiety binding to the reactive chelate) or the AC, there are a number of additional crosslinkers such as 2-iminothiolane or N-succinimidyl S-acetylthioacetate (SATA), available for forming disulfide bonds. 2-iminothiolane reacts with primary amines, instantly incorporating an unprotected sulfhydryl onto the protein. SATA also reacts with primary amines, but incorporates a protected sulfhydryl, which is later deacetaylated using hydroxylamine to produce a free sulfhydryl. In each case, the incorporated sulfhydryl is free to react with other sulfhydryls or protected sulfhydryl, like SPDP, forming the required disulfide bond.

The above-described strategy is exemplary and not limiting of linkers of use in the invention. Other crosslinkers are available that can be used in different strategies for crosslinking the targeting agent to the antibody. For example, TPCH (S-(2-thiopyridyl)-L-cysteine hydrazide and TPMPH ((S-(2-thiopyridyl) mercapto-propionohydrazide) react at the carbohydrate moieties of glycoproteins that have been previously oxidized by mild periodate treatment, thus forming a hydrazone bond between the hydrazide portion of the crosslinker and the periodate generated aldehydes. The placement of this crosslinker on the antibody is beneficial since the modification is site-specific and will not interfere with the antigen binding site of the antibody. TPCH and TPMPH introduce a 2-pyridylthione protected sulfhydryl group onto the antibody, which can be deprotected with DTT and then subsequently used for conjugation, such as forming disulfide bonds between components.

If disulfide bonding is found unsuitable for producing stable conjugates, other crosslinkers may be used that incorporate more stable bonds between components. The heterobifunctional crosslinkers GMBS (N-gamma-maleimidobutyryloxy)succinimide) and SMCC (succinimidyl 4-(N-maleimido-methyl)cyclohexane) react with primary amines, thus introducing a maleimide group onto the component. This maleimide group can subsequently react with sulfhydryls on the other component, which can be introduced by previously mentioned crosslinkers, thus forming a stable thioether bond between the components. If steric hindrance between components interferes with either component's activity, crosslinkers can be used which introduce long spacer arms between components and include derivatives of some of the previously mentioned crosslinkers (i.e., SPDP). Thus there is an abundance of suitable crosslinkers, which are useful; each of which is selected depending on the effects it has on optimal immunoconjugate production.

A variety of reagents are used to modify the components of the conjugate with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (J. S. Holcenberg, and J. Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred useful crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

e. Preferred Specific Sites in Crosslinking Reagents

1. Amino-Reactive Groups

In one preferred embodiment, the sites are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of the affinity component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the conjugate components. At a pH between 7 and 10, imidoesters react only with primary amines. Primary amines attack imidates nucleophilically to produce an intermediate that breaks down to amidine at high pH or to a new imidate at low Ph. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of mono- and dicarboxylic acids are also useful amino-reactive groups. Although the reagent specificity is not very high, α- and ε-amino groups appear to react most rapidly.

Aldehydes such as glutaraldehyde react with primary amines of the conjugate components (e.g., ε-amino group of lysine residues). Glutaraldehyde, however, displays also reactivity with several other amino acid side chains including those of cysteine, histidine, and tyrosine. Since dilute glutaraldehyde solutions contain monomeric and a large number of polymeric forms (cyclic hemiacetal) of glutaraldehyde, the distance between two crosslinked groups within the affinity component varies. Although unstable Schiff bases are formed upon reaction of the protein amino groups with the aldehydes of the polymer, glutaraldehyde is capable of modifying the affinity component with stable crosslinks. At pH 6-8, the pH of typical crosslinking conditions, the cyclic polymers undergo a dehydration to form α,β-unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the conjugate components, but reaction with the amino groups is the most important, resulting in a stable sulfonamide linkage.

2. Sulfhydryl-Reactive Groups

In another preferred embodiment, the sites are sulfhydryl-reactive groups. Useful non-limiting examples of sulfhydryl-reactive groups include maleimides, alkyl halides, pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form also disulfides.

3. Guanidino-Reactive Groups

In another embodiment, the sites are guanidino-reactive groups. A useful non-limiting example of a guanidino-reactive group is phenylglyoxal. Phenylglyoxal reacts primarily with the guanidino groups of arginine residues in the affinity component. Histidine and cysteine also react, but to a much lesser extent.

4. Indole-Reactive Groups

In another embodiment, the sites are indole-reactive groups. Useful non-limiting examples of indole-reactive groups are sulfenyl halides. Sulfenyl halides react with tryptophan and cysteine, producing a thioester and a disulfide, respectively. To a minor extent, methionine may undergo oxidation in the presence of sulfenyl chloride.

5. Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage (Yamada et al., *Biochemistry* 20: 4836-4842, 1981) teach how to modify a protein with carbodiimde.

f. Preferred Nonspecific Sites in Crosslinking Reagents

In addition to the use of site-specific reactive moieties, the present invention contemplates the use of non-specific reactive groups to link the antibody to the targeting moiety. Non-specific groups include photoactivatable groups, for example.

In another preferred embodiment, the sites are photoactivatable groups. Photoactivatable groups, completely inert in the dark, are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, and C═C. Although three types of azides (aryl, alkyl, and acyl derivatives) may be employed, arylazides are presently preferrred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein crosslinks.

g. Homobifunctional Reagents

1. Homobifunctional Crosslinkers Reactive with Primary Amines

Synthesis, properties, and applications of such reagents are described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy) ethylsulfone (BSOCOES), bis-2-(sulfosuccinimidooxycarbonyloxy)ethylsulfone (sulfo-BSOCOES), ethylene glycolbis(succinimidylsuccinate) (EGS), ethylene glycolbis (sulfosuccinimidylsuccinate) (sulfo-EGS), dithiobis (succinimidylpropionate (DSP), and dithiobis (sulfosuccinimidylpropionate (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3,3'-(tetramethylenedioxy)dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and .alpha.-naphthol-2,4-disulfonyl chloride.

Preferred, non-limiting examples of additional amino-reactive homobifunctional reagents include erythritolbiscarbonate which reacts with amines to give biscarbamates.

2. Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene)bismaleimide, N,N'-(1,2-phenylene)bismaleimide, azophenyldimaleimide, and bis(N-maleimidomethyl) ether. Preferred, non-limiting examples of homobifunctional pyridyl disulfides include 1,4-di->3'-(2'-pyridyldithio)propionamidobutane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α,α'-dibromo-p-xylenesulfonic acid, N,N'-bis(b-bromoethyl)benzylamine, N,N'-di(bromoacetyl)phenylthydrazine, and 1,2-di (bromoacetyl)amino-3-phenylpropane.

3. Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-b-(4-azidosalicylamido)ethyldisulfide (BASED), di-N-(2-nitro-4-azidophenyl)-cystamine-S,S-dioxide (DNCO), and 4,4'-dithiobisphenylazide.

h. Hetero-Bifunctional Reagents

1. Amino-Reactive Hetero-Bifunctional Reagents with a Pyridyl Disulfide Moiety

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio) propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-a-methyl-α-(2-pyridyldithio) toluene (SMPT), and sulfosuccinimidyl 6-a-methyl-α-(2-pyridyldithio)toluamidohexanoate (sulfo-LC-SMPT).

2. Amino-Reactive Hetero-Bifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

3. Amino-Reactive Hetero-Bifunctional Reagents with an Alkyl Halide Moiety

Synthesis, properties, and applications of such reagents are described in the literature. Preferred, non-limiting examples of hetero-bifunctional reagents with an alkyl halide moiety and an amino-reactive NHS ester include N-succinimidyl-(4-iodoacetyl)aminobenzoate (SLAB), sulfosuccinimidyl-(4-iodoacetyl)aminobenzoate (sulfo-SLAB), succinimidyl-6-(iodoacetyl)aminohexanoate (SLAX), succinimidyl-6-(6-((iodoacetyl)-amino)hexanoylamino)hexanoate (SIAXX), succinimidyl-6-(((4-(iodoacetyl)-amino)-methyl)-cyclohexane-1-carbonyl)aminohexanoate (SIACX), and succinimidyl-4((iodoacetyl)-amino)methylcyclohexane-1-carboxylate (SIAC).

A preferred example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety for primary amino groups is controlled by the reaction temperature (McKenzie et al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

4. Photoactivatable Arylazide-Containing Hetero-Bifunctional Reagents with a NHS Ester Moiety Synthesis, properties, and applications of such reagents are described in the literature. Preferred, non-limiting examples of photoactivatable arylazide-containing hetero-bifunctional reagents with an amino-reactive NHS ester include N-hydroxysuccinimidyl-4-azidosalicylic acid (NHS-ASA), N-hydroxysulfosuccinimidyl-4-azidosalicylic acid (sulfo-NHS-ASA), sulfosuccinimidyl-(4-azidosalicylamido)hexanoate (sulfo-NHS-LC-ASA), N-hydroxysuccinimidyl N-(4-azidosalicyl)-6-aminocaproic acid (NHS-ASC), N-hydroxysuccinimidyl-4-azidobenzoate (HSAB), N-hydroxysulfosuccinimidyl-4-azidobenzoate (sulfo-HSAB), sulfosuccinimidyl-4-(p-azidophenyl)butyrate (sulfo-SAPB), N-5-azido-2-nitrobenzoyloxy-succinimide (ANB-NOS), N-succinimidyl-6-(4'-azido-2'-nitrophenyl-amino)hexanoate (SANPAH), sulfosuccinimidyl-6-(4'-azido-2'-nitrophenylamino)hexanoate (sulfo-SANPAH), N-succinimidyl 2-(4-azidophenyl)dithioacetic acid (NHS-APDA), N-succinimidyl-(4-azidophenyl)1,3'-dithiopropionate (SADP), sulfosuccinimidyl-(4-azidophenyl)-1,3'-dithiopropionate (sulfo-SADP), sulfosuccinimidyl-2-(m-azido-o-nitrobenzamido) ethyl-1,3'-dithiopropionate (SAND), sulfosuccinimidyl-2-(p-azidosalicylamido)ethyl-1,3'-dithiopropionate (SASD), N-hydroxysuccinimidyl 4-azidobenzoylglycyltyrosine (NHS-ABGT), sulfosuccinimidyl-2-(7-azido-4-4-methylcoumarin-3-acetamide)ethyl-1,3'-dithiopropionate (SAED), and sulfosuccinimidyl-7-azido-4-methylcoumarin-3-acetate (sulfo-SAMCA).

Other cross-linking agents are known to those of skill in the art (see, for example, Pomato et al., U.S. Pat. No. 5,965,106.

i. Linker Groups

In addition to the embodiments set forth above, wherein the cross-linking moiety is attached directly to a site on the antibody and on the targeting moiety, the present invention also provides constructs in which the cross-linking moiety is bound to a site present on a linker group that is bound to either the antibody or the targeting moiety or both. In certain embodiments, it is advantageous to tether the antibody and the targeting moiety by a group that provides flexibility and increases the distance between the antibody and the targeting moiety. Using linker groups, the properties of the oligonucleotide adjacent to the stabilizing moiety can be modulated. Properties that are usefully controlled include, for example, hydrophobicity, hydrophilicity, surface-activity and the distance of the targeting moiety from the oligonucleotide.

In an exemplary embodiment, the linker serves to distance the antibody from the targeting moiety. Linkers with this characteristic have several uses. For example, a targeting moiety held too closely to the antibody may not interact with its complementary group, or it may interact with too low of an affinity. Similarly, a targeting moiety held to closely to the antibody may prevent the antibody from binding the reactive chelate. Thus, it is within the scope of the present invention to utilize linker moieties to, inter alia, vary the distance between the antibody and the targeting moiety.

In yet a further embodiment, the linker group is provided with a group that can be cleaved to release the mutant antibody from the targeting moiety. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover, a broad range of cleavable, bifunctional (both homo- and hetero-bifunctional) linker groups are commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to their being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

In the discussion set forth above, examples are set forth in which the linkers are located between the mutant antibody and a targeting moiety. Those of skill will appreciate that linkers can also be interposed between the chelating agent and the reactive functional group having reactivity complementary to the reactivity of the reactive site on the mutant antibody.

j. Fusion Proteins

In a preferred form, the antibodies are recombinantly produced as fusion proteins with a second, antitumor antibody that acts to target the fusion protein to an antigen of a targeted tumor. Dozens of antitumor antigens and antibodies against them are known in the art, many of which are in clinical trials. Examples include AMD-Fab, LDP-02, aCD-11a, aCD-18, a-VEGF, a-IgE, and Herceptin, from Genentech, ABX-CBL, ABX-EGF, and ABX-IL8, from Abgenix, and aCD3, Smart 195 and Zenepax from Protein Design Labs. In preferred forms, the antibody is HMFG1, L6, or Lym-1, with Lym-1 being the most preferred. In preferred embodiments, an scFv or dsFv form of the antibody is employed. Formation of scFvs and dsFvs is known in the art. Formation of a scFv of Lym-1, for example, is taught Bin Song et al., *Biotechnol Appl Biochem* 28(2):163-7 (1998). See, also *Cancer Immunol. Immunother.* 43: 26-30 (1996). The two antibodies can be linked directly or, more commonly, are connected by a short peptide linker, such as $Gly_4Ser$ repeated 3 times (SEQ ID NO:72).

2. The Chelates

In addition to the antibodies and mutant antibodies described in detail above, the invention also provides reactive chelates that are specifically recognized by the antibody antigen recognition domain and which form covalent bonds with the reactive group on the mutant antibody.

In an exemplary embodiment, there is provided a metal chelate that is recognized by the antigen recognition domain of an antibody. The antibody includes a reactive site not present in the wildtype of the antibody and the reactive site is in a position proximate to or within the antigen recognition domain. In some embodiments, the metal chelate comprises four nitrogen atoms.

In a preferred embodiment, the chelate includes a substituted or unsubstituted ethyl bridge that covalently links at least two of the nitrogen atoms. An exemplary ethyl bridge is shown in the formula below:

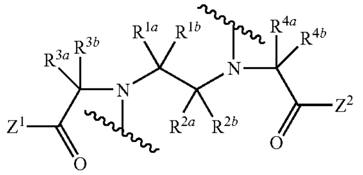

wherein $Z^1$ and $Z^2$ are members independently selected from OR and $NR^3R^4$, in which $R^3$ and $R^4$ are members independently selected from H, substituted or unsubstituted alkyl and substituted or unsubstituted heteroalkyl. The symbols $R^{1a}$, $R^{1b}$, $R^{2a}$, $R^{2b}$, $R^{3a}$, $R^{3b}$, $R^{4a}$ and $R^{4b}$ represent members independently selected from H, substituted or unsubstituted alkyl, substituted or unsubstituted heteroalkyl, substituted or unsubstituted aryl and linker moieties.

In another exemplary embodiment, the chelate has the formula:

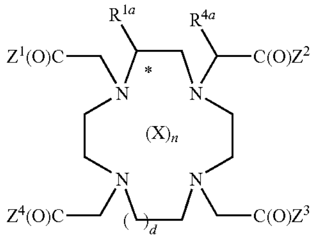

wherein $Z^1$, $Z^2$, $Z^3$ and $Z^4$ are members independently selected from $OR^1$ and $NR^1R^2$, in which $R^1$ and $R^2$ are members independently selected from H, substituted or unsubstituted alkyl and substituted or unsubstituted heteroalkyl. The symbol X represents a member selected from a lanthanide, an actinide, an alkaline earth metal, a group IIIb transition metal, or a metal. The symbol n represents 0 or 1; and d is 1 or 2. In a preferred embodiment, the carbon atom marked * is of S configuration.

In another exemplary embodiment, the chelate includes a moiety having the formula:

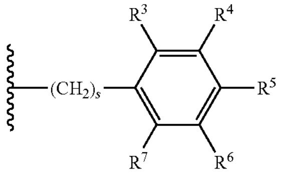

wherein $R^3$, $R^4$, $R^5$, $R^6$ and $R^7$ are members independently selected from H, halogen, $NO_2$, CN, $X^1R^8$, $NR^9R^{10}$, and $C(X^2)R^{11}$. The symbol $X^1$ represents a member selected from O, NH and S. The symbols $R^8$ and $R^9$ are members independently selected from H, substituted or unsubstituted alkyl, substituted or unsubstituted heteroalkyl and $C(Z^3)R^{12}$, in which $X^3$ is a member selected from O, S and NH. $R^{12}$ is a member selected from substituted or unsubstituted alkyl, substituted or unsubstituted heteroalkyl and $OR^{13}$, in which $R^{13}$ is a member selected from substituted or unsubstituted alkyl, substituted or unsubstituted heteroalkyl, substituted or unsubstituted aryl and substituted or unsubstituted heteroaryl. The symbol $R^{10}$ is a member selected from H, substituted or unsubstituted alkyl, substituted or unsubstituted heteroalkyl and OH, and $R^9$ and $R^{10}$, taken together are optionally (=C=S). $X^2$ is a member selected from O, S and NH. The symbol R11 represents a member selected from H, halogen, substituted or unsubstituted alkyl, substituted or unsubstituted heteroalkyl, $OR^{14}$, $NR^{15}R^{16}$. $R^{14}$ is a member selected from H, substituted or unsubstituted alkyl, substituted or unsubstituted heteroalkyl, and $C(O)R^{17}$. $R^{17}$ is a member selected from substituted or unsubstituted alkyl and substituted or unsubstituted heteroalkyl; and $R^{15}$ and $R^{16}$ are members independently selected from H, substituted or unsubstituted alkyl and substituted or unsubstituted heteroalkyl.

In practicing the present invention, the structure of the metal binding portion of the chelate is selected from an array of structures known to complex metal ions. Exemplary chelating agents of use in the present invention include, but are not limited to, reactive chelating groups capable of chelating radionuclides include macrocycles, linear, or branched moieties. Examples of macrocyclic chelating moieties include polyaza- and polyoxamacrocycles, polyether macrocycles, crown ether macrocycles, and cryptands (see, e.g., Synthesis of Macrocycles: the Diesgn of Selective Complexing Agents (Izatt and Christensen ed., 1987) and The Chemistry of Macrocyclic Ligand Complexes (Lindoy, 1989)). Examples of polyazarnacrocyclic moieties include those derived from compounds such at 1,4,7,10-tetraazacyclododecane-N,N',N'',N'''-tetraacetic acid ("DOTA"); 1,4,7,10-tetraazacyclotridecane-N,N',N'',N'''-tetraacetic acid ("TRITA"); 1,4,8,11-tetraazacyclotetradecane-N,N',N'',N'''-tetraacetic acid ("TETA"); and 1,5,9,13-tetraazacyclohexadecane-N,N',N'',N'''-tetraacetic acid (abbreviated herein abbreviated as HETA). In a presently preferred embodiment, the chelating agent includes four nitrogen atoms. Other embodiments in which the chelate includes oxygen atoms or mixtures of oxygen and nitrogen atoms are within the scope of the present invention.

Chelating moieties having carboxylic acid groups, such as DOTA, TRITA, HETA, and HEXA, may be derivatized to convert one or more carboxylic acid groups to reactive groups. Alternatively, a methylene group adjacent to an amine or a carboxylic acid group can be derivatized with a reactive functional group. Additional exemplary chelates of use in the present invention are set forth in Meares et al., U.S. Pat. No. 5,958,374.

The preparation of chelates useful in practicing the present invention is accomplished using art-recognized methodologies or modifications thereof. In a preferred embodiment of the invention, a reactive derivative of DOTA is used. Preparation of DOTA is described in, e.g., Moi et al., *J. Am. Chem. Soc.* 110:6266-67 (1988) and Renn and Meares, *Bioconjugate Chem.* 3:563-69 (1992).

The chelate that is linked to the antibody or growth factor targeting agent will, of course, depend on the ultimate application of the invention. Where the aim is to provide an image of the tumor, one will desire to use a diagnostic agent that is detectable upon imaging, such as a paramagnetic, radioactive or fluorogenic agent. Many diagnostic agents are known in the art to be useful for imaging purposes, as are methods for their attachment to antibodies (see, e.g., U.S. Pat. Nos. 5,021,236 and 4,472,509, both incorporated herein by reference). In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III). Moreover, in the case of radioactive isotopes for therapeutic and/or diagnostic application, presently preferred isotopes include $iodine^{131}$, $iodine^{123}$, $technicium^{99m}$, $indium^{111}$, $rhenium^{188}$, $rhenium^{186}$, $gallium^{67}$, $copper^{67}$, $yttrium^{90}$, $iodine^{125}$ or $astatine^{211}$.

Antibody-Chelate Bond Formation

In some exemplary embodiments, after the formation of the antibody-antigen (chelate) complex, the reactive chelate and mutant antibody of the invention are linked together through the use of reactive groups, which are typically transformed by the linking process into a new organic functional group or unreactive species. The chelate reactive functional group(s), is located at any position on the metal chelate. Reactive groups and classes of reactions useful in practicing the present invention are generally those that are well known in the art of bioconjugate chemistry. Currently favored classes of reactions available with reactive chelates are those that proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Useful reactive pendant functional groups include, for example:

(a) carboxyl groups and various derivatives thereof including, but not limited to, N-hydroxysuccinimide esters, N-hydroxybenztriazole esters, acid halides (e.g., I, Br, Cl), acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the reactive chelates. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

B. The Methods

In addition to the compositions of the invention, the present invention provides methods for using the compositions. Thus, in a fourth aspect, the invention provides a method of using the compositions of the invention to treat a patient for a disease or condition (e.g., cancer or autoimmune diseases, such as diabetes, arthritis, systemic lupus erythematosus) or to diagnose a condition or disease. The method comprising the steps of: (a) administering to the patient an antibody comprising; (i) an antigen recognition domain that specifically binds to the metal chelate and (ii) a targeting moiety that binds specifically to a cell by binding with a surface group (e.g., cell surface receptors and cell surface antigens), thereby forming a complex between the antibody and the cell. Following step (a), the metal chelate is administered to the patient. Thus, the chelate and the antibody bind to form an antibody-antigen (chelate) pair, the reactive groups of which subsequently react to form an irreversible bond between the antibody and the antigen. In some embodiments, the antibody is a mutant antibody comprising a reactive site not present in the wild-type of the antibody, wherein the reactive site is in a position proximate to or within the antigen recognition domain. The reactive site of said mutant antibody has a reactivity complementary to a reactive functional group on the metal chelate. As discussed above, the techniques relevant to raising antibodies and preparing chelates useful in the above-recited method are well known in the art.

The present invention provides antibodies raised against essentially any chelate of any metal ion. In a preferred embodiment, the antibody used for pretargeting is 2D12.5, a monoclonal antibody that binds metal chelates of DOTA and to similar structures.

In addition to the method described above, the present invention also provides a method in which the tissue is pretargeted with an antibody of the invention. This pretargeting method of treating a patient with a metal chelate comprises the steps of: (a) administering to a patient an antibody comprising (i) an antigen recognition domain that specifically binds to the metal chelate; and (ii) a recognition moiety that binds specifically with the pretargeting reagent, thereby forming a complex between the cells and the antibody. After the antibody has localized in the desired tissue, a metal chelate is administered to the patient. The chelate specifically binds to the antibody of the invention, forming an antibody-metal chelate complex.

In some embodiments, the antibody is a mutant antibody comprising a reactive site not present in the wild-type of the antibody (the reactive site is in a position proximate to or within the antigen recognition domain) and the chelate comprises a reactive functional group having a reactivity that is preferably complementary to the reactivity of the reactive site on the mutant antibody such that a covalent bond is formed via reaction of the reactive functional group of the chelate and the reactive site of the mutant antibody. After the antibody-antigen complex is formed, the reactive site of the antibody and that of the metal chelate react to form a covalent bond between the mutant antibody and the metal chelate.

Pretargeting methods have been developed to increase the target:background ratios of the detection or therapeutic agents. Examples of pre-targeting and biotin/avidin approaches are described, for example, in Goodwin et al., U.S. Pat. No. 4,863,713; Goodwin et al., *J. Nucl. Med.* 29: 226 (1988); Hnatowich et al., *J. Nucl. Med.* 28: 1294 (1987); Oehr et al., *J. Nucl. Med.* 29: 728 (1988); Klibanov et al., *J. Nucl. Med.* 29: 1951 (1988); Sinitsyn et al., *J. Nucl. Med.* 30: 66 (1989); Kalofonos et al., *J. Nucl. Med.* 31: 1791 (1990); Schechter et al., *Int. J. Cancer* 48:167 (1991); Paganelli et al., *Cancer Res.* 51:5960 (1991); Paganelli et al., *Nucl. Med. Commun.* 12: 211 (1991); Stickney et al., *Cancer Res.* 51: 6650 (1991); and Yuan et al., *Cancer Res.* 51:3119, 1991; all of which are incorporated by reference herein in their entirety.

In both of the above-described aspects of the invention, it is preferable that a significant proportion of the antibodies used remain on the cell surface to be accessible to a later introduced moiety containing the radioactive agent. Thus, it is generally preferable to choose antigens that are not rapidly endocytosed or otherwise internalized by the cell upon antibody binding. Preferably, at least one-quarter of the bound antibody should remain on the cell surface and not be internalized. In some cases, however, even less of the bound antibody may remain on the cell surface. For example, for a particular tumor type, an antigen which has a high rate of internalization may still be used for pretargeting if there is no known antigen with a lower internalization rate (or for which an antibody is available) with which to image tumor locations. The suitability of a particular antigen can be determined by simple assays known in the art.

1. Clearing Agents

Clearing agents known in the art may be used in accordance with the present invention. In a preferred embodiment, the clearing agent is an antibody that binds the binding site of the targeting species, where the targeting species can be an antibody, an antigen binding antibody fragment or a non-antibody targeting species. In a more preferred embodiment, the clearing agent is a MAb that is anti-idiotypic to the MAb of the conjugate used in the first step, as described in U.S. application Ser. No. 08/486,166. In another preferred embodiment, the clearing agent is substituted with multiple residues of carbohydrate, such as galactose, which allow the clearing agent to be cleared quickly from circulation by asialoglycoprotein receptors in the liver.

In a more preferred embodiment, the clearing agent is an anti-idiotypic MAb substituted with galactose and small numbers of biotin residues. Different purposes are being accomplished here. The anti-idiotypic MAb clears the first antibody conjugate (radioiodinated MAb-SAv) from circulation and deposits this into the hepatocytes. Because the anti-idiotypic MAb binds to the Mab binding region of the first antibody, it does not remove first antibody conjugate already localized at the tumor sites.

The multiple galactose substitution ensures the rapid clearance of the anti-idiotypic MAb into the liver hepatocytes, usually within minutes. Because the anti-idiotypic MAb is galactosylated and cleared rapidly, it does not have a chance to competitively remove the tumor-localized first antibody conjugate from the tumor over time. Also, there is very little myelotoxicity since almost all circulating radioactivity has been removed from the blood.

2. Blocking Agents

Blocking agents known in the art may be used in accordance with the present invention. In an exemplary embodiment, a blocking agent (e.g., an agent that reduces the uptake of metal chelates into unwanted targets), metal chelate conjugate (see, e.g., Karacay et al., *Bioconjugate Chem.* 13:1054-1070 (2002)). Suitable blocking agents include, for example, DOTA-conjugated to bovine serum albimun (BSA), DOTA conjugated to immunoglobulin, and DOTA conjugated to peptides.

The materials, methods and devices of the present invention are further illustrated by the examples that follow. These examples are offered to illustrate, but not to limit the claimed invention.

EXAMPLES

Example 1 sets forth the use of rational computer-aided design to develop mutants of the monoclonal antibody 2D12.5. Example 2 describes construction of chimeric constructs comprising the variable domain of 2D12.5 and human antibody specific for tetanus toxoid. Example 3 demonstrates that the monoclonal antibody 2D12.5 has broad specificity and high affinity for all rare earth metal DOTA complexes.

Example 1

This Example sets forth the use of rational computer-aided design to develop mutants of the monoclonal antibody 2D12.5.

Evaluation of the crystal structure of 2D12.5 bound to its hapten, Y-DOTA in conjunction with molecular modeling software (InsightII, Biosym/MSI) identified two specific side-arm orientations of the chelate in the binding pocket. This observation led to the design and engineering of four separate cysteine mutants (three heavy chain and one light chain). Specifically, cysteine residues were substituted at positions 53, 54, and 55 (positions 54, 55, and 55 if the Kabat standard numbering system is used) of the heavy chain variable domain and position 53 (position 54 if the Kabat standard numbering system is used) of the light chain variable domain. These mutants can conveniently be used in experiments to evaluate the ability of the mutants to irreversible bind suitably derived electrophilic chelates. Additional mutants can conveniently be generated based on the evaluation of the crysal structure of 2D12.5 bound to its hapten.

Example 2

The following example describes the methodology used to prepare chimeric heavy and light chain Fab genes for expression in *Drosophila* Schneider (S2) cells.

As explained above, after inspection of the crystal structure we chose to introduce cysteine residues at positions 53, 54, and 55 (positions 54, 55, and 55 if the Kabat standard numbering system is used) of the heavy chain variable domain and position 53 (position 54 if the Kabat standard numbering system is used) of the light chain variable domain.

2D12.5 hybridoma cells were grown in RPMI 1640 supplemented with 10% FCS and used as a source of genetic template. Poly A mRNA was extracted with the Oligotex Direct mRNA Extraction kit (Qiagen). Complementary DNA synthesis and PCR amplification of the variable domain genes was accomplished using Novagen's Mouse Ig-Primer kit which incorporates degenerate 3' constant domain primers specific to mouse IgG genes. Double stranded DNA was obtained from cDNA using degenerate 5' and 3' primers provided in the Mouse Ig-Primer kit. The heavy and light chain variable genes, each with an unpaired 3' terminal A, were cloned separately into a pT7Blue T-vector and sequenced. The variable domains were then used to prepare expression constructs.

Figure 10E:
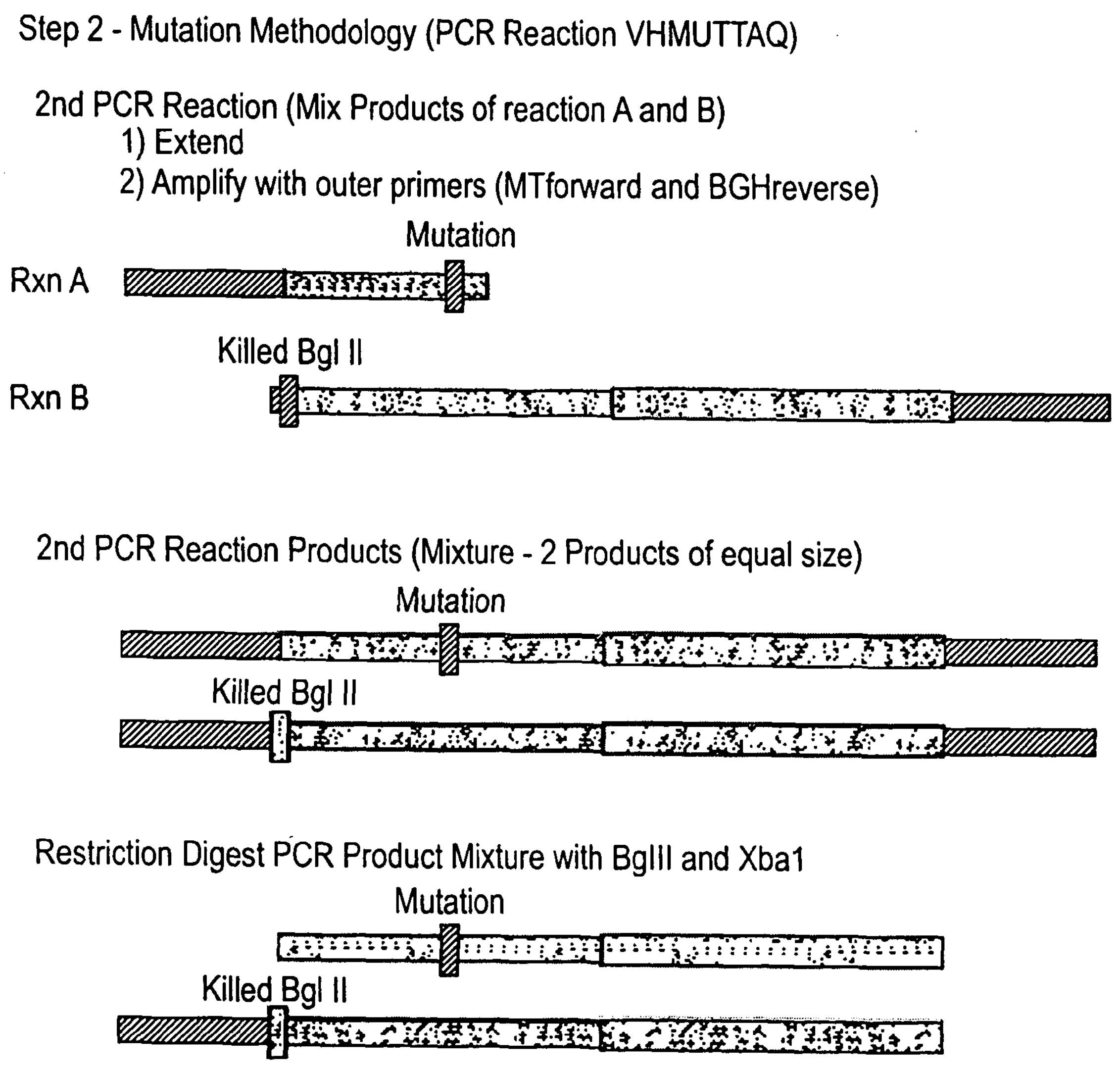
FIG. 10 is a diagram depicting the strategy for assembly of the chimeric $V_H$ chain of 2D12.5 fused to the CH1 chain of a human anti-tetanus toxoid antibody.
FIG. 10A Primers=SEO ID NOS:49-52.
FIG. 10B Primers=SEQ ID NOS:49 and 52.
Figure 11A:
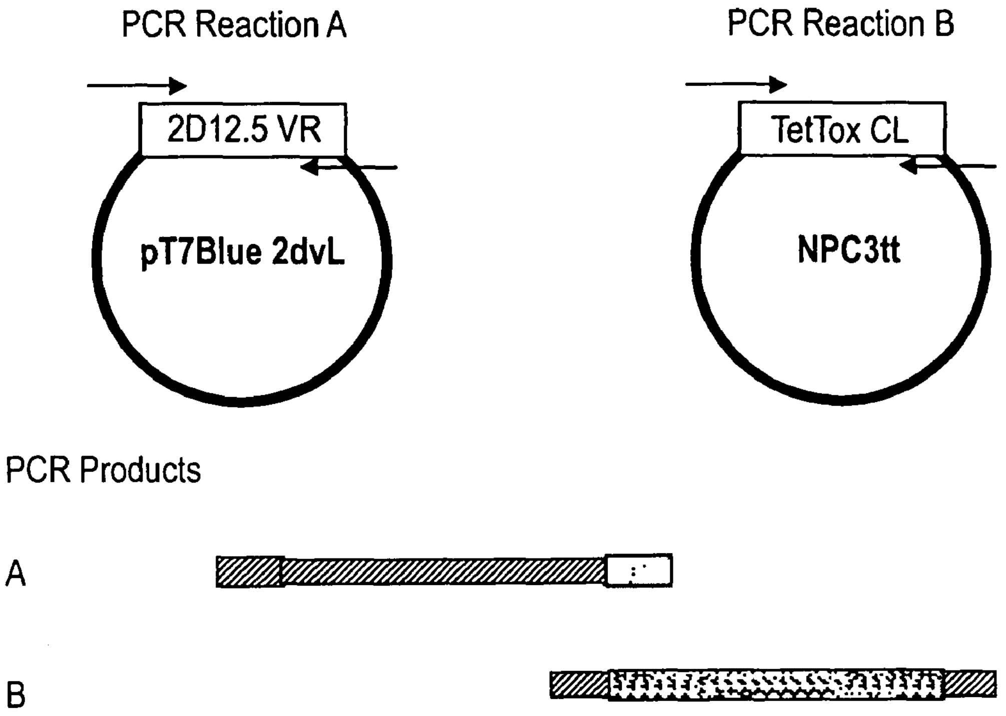
FIG. 11A Primers=SEQ ID NOS: 64-67.
Figure 11C:
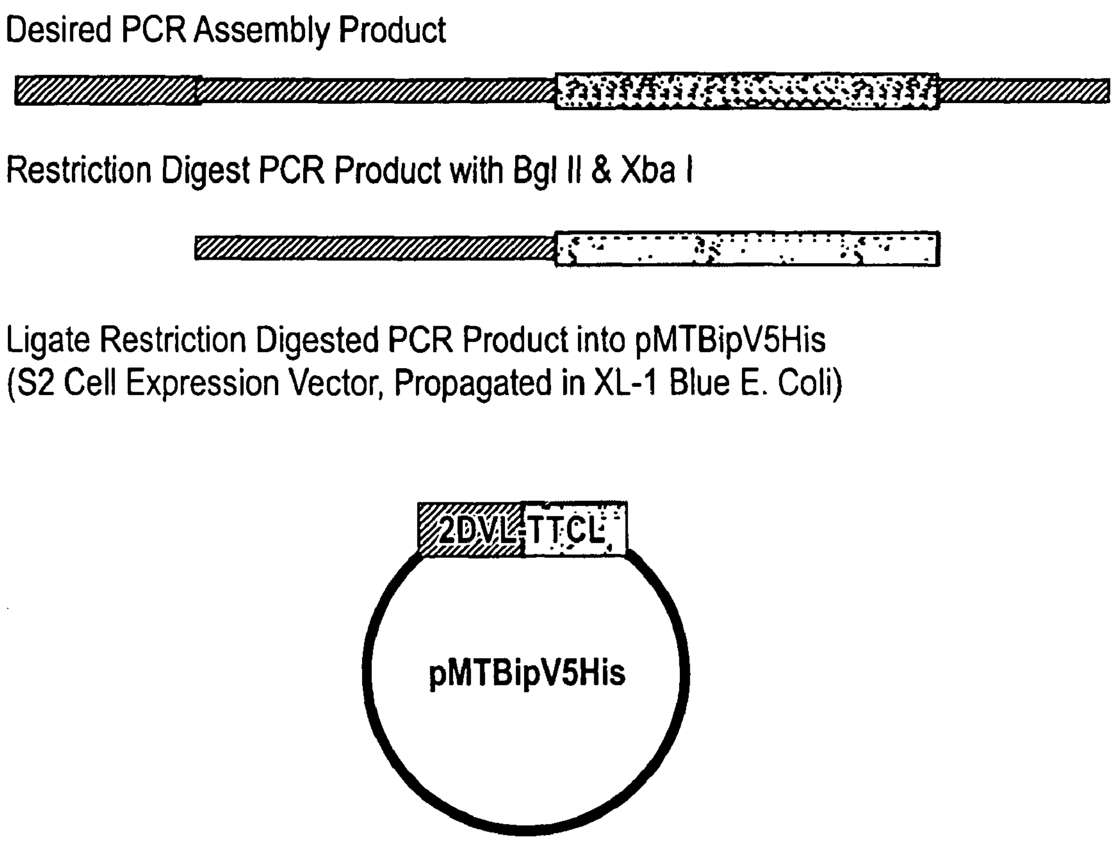
FIG. 11 is a diagram depicting the strategy for assembly of the chimeric $V_L$ chain of 2D12.5 fused to the $C_L$ kappa chain of a human anti-tetanus toxoid antibody.
FIG. 11B Primers=SEQ ID NOS: 64 and 67.
FIG. 11D Mutation Methodology sequences=SEQ ID NOS:53, 54, 68 and 56.
FIG. 11F Primers=SEQ ID NOS:57, 65, 66 and 67.
Figure 11E:
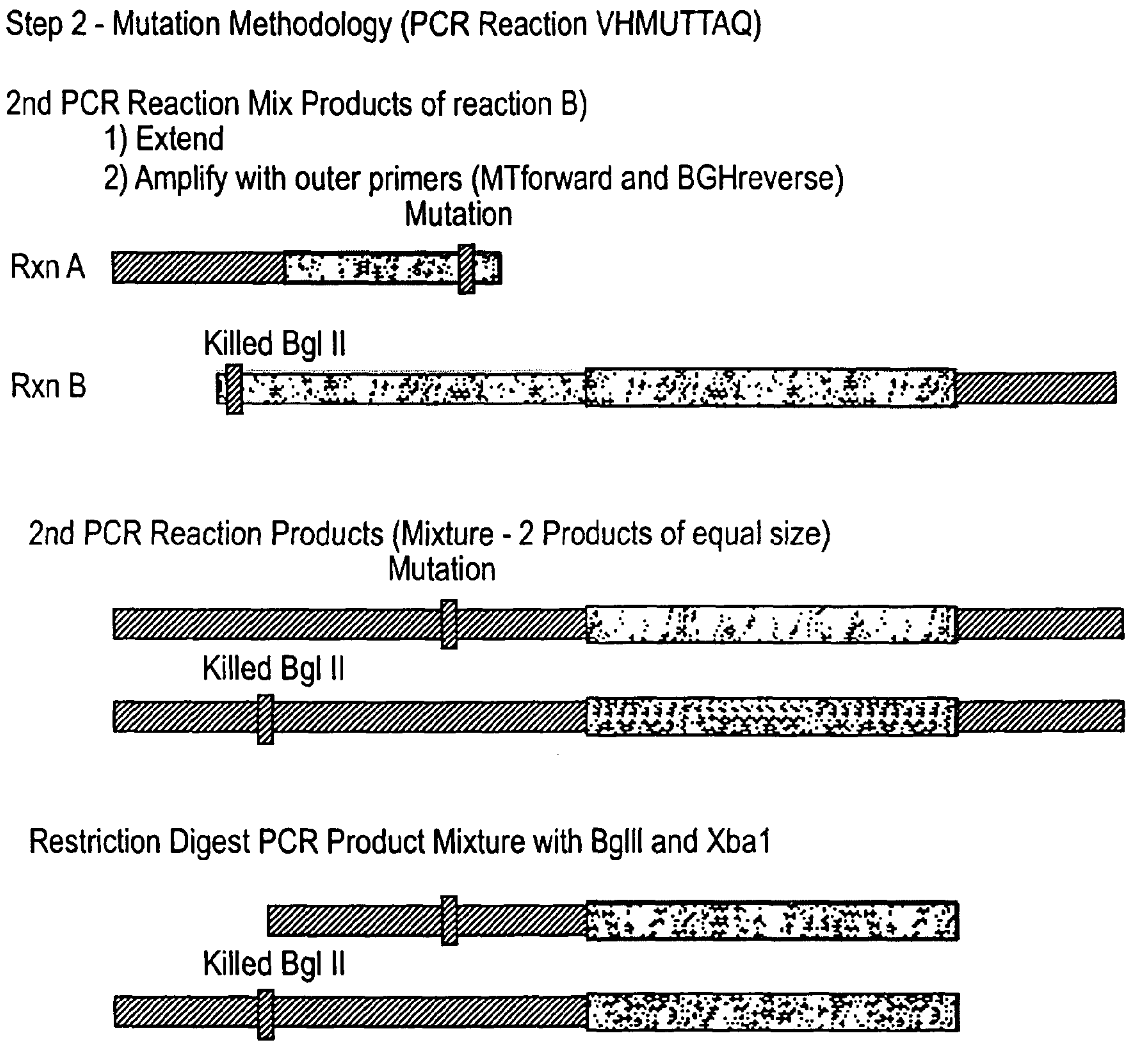
Figure 11G:
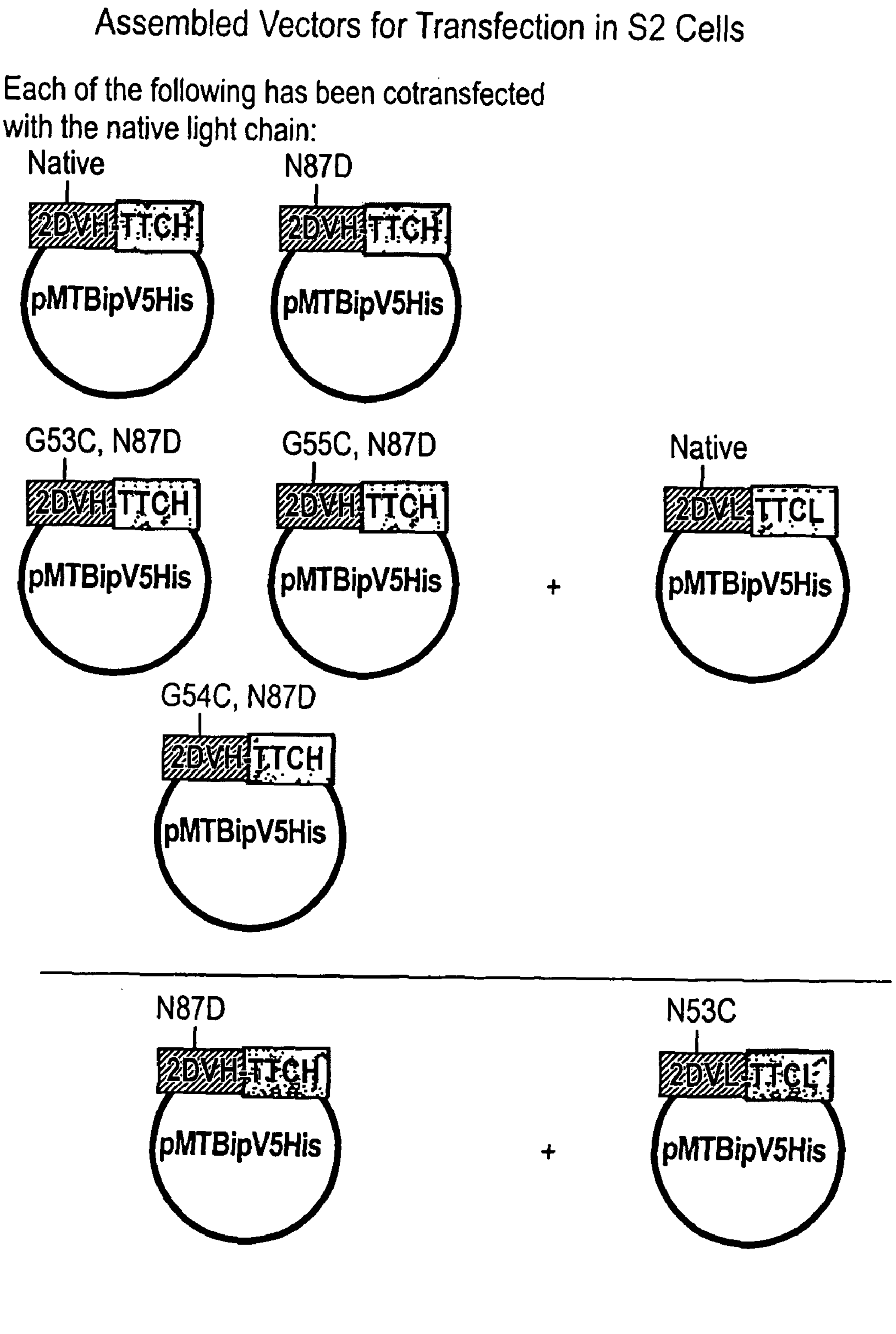

Assembly of the chimeric constructs is shown in FIG. 10 (heavy chain) and FIG. 11 (light chain). Chimeric constructs of the murine 2D12.5 variable (light and heavy) domains and human anti-tetanus toxoid antibody CL and CH1 domains were assembled by two-step overlap extension (see, e.g., Pont-Kingdon, *Biotechniques* 16:1010-1011 (1994) and erratum 18:636 (1995)) and as shown in FIGS. 10 and 11. A BglII restriction site was introduced onto the 5' end of heavy and light chain genes and a XbaI restriction site was introduced onto the 3' end of the tetanus toxin CH1 chain or $C_L$K chain during overlap extension, and were used to introduce each chimeric gene construct into the pMT/Bip/V5/His plasmid cassette for propagation in *E. coli* and expression in *Drosophila* S2 cells. Heavy and light chain genes were placed into separate plasmids. Site directed substitution of aspartic acid at position 87 (N87D) of the heavy chain was accomplished as described in Ito et al., *Gene* 102: 67-70 (1991). Site directed substitution of cysteine at positions 53 (G53C), 54 (G54C), and 55 (G55C) of the heavy chain and position 53 (N53C) of the light chain was also accomplished as described in Ito et al., 1991, supra. Mutations were prepared using MT and BGH sequencing primers as well as a killed BglII primer, and site-specific mutation primers. As shown in FIGS. 10 and 11, four primers and two PCR steps are required to install a mutation in a gene by this method. The primers for site-directed substitution at positions 53 (G53C), 54 (G54C), and 55 (G55C) of the heavy chain are shown in FIG. 10 and the primers for site-directed substitution at position position 53 (N53C) of the light chain is shown in FIG. 11, as are exemplary PCR conditions and reaction mixtures.

Heavy and light chain containing plasmids were cotransfected into *Drosophila* S2 cells using precipitating calcium phosphate. Cells were induced using 500 μM $CUSO_4$. Stable cell lines were produced by cotransfecting a plasmid containing the hygromycin B phosphotransferase gene along with heavy and light chain DNA. Selection proceeded for 3-4 weeks post-transfection with 300 μg/mL hygromycin B.

Each of the heavy chains were cotransfected with the native light chain in *Drosophila* S2 cells. Also, the N87D heavy chain was cotransfected with the N53C light chain. Stably transfected *Drosophila* S2 cells were induced (native as well as 4 cysteine mutants), and the media was assayed for gene expression by denaturing, nonreducing SDS gel separation followed by Western Blot analysis. Goat anti-human-K and anti-V5 epitope antibodies (alkaline phosphatase (AP) conjugates) were used to detect for light and heavy chains, respectively. It is clear from the blots that there is heterogeneous glycosylation of the heavy chain. The glycoprotein bands are not present in heavy chains incorporating the N87D mutation, yielding a homogeneous product that is preferable for future applications.

Figure 12:
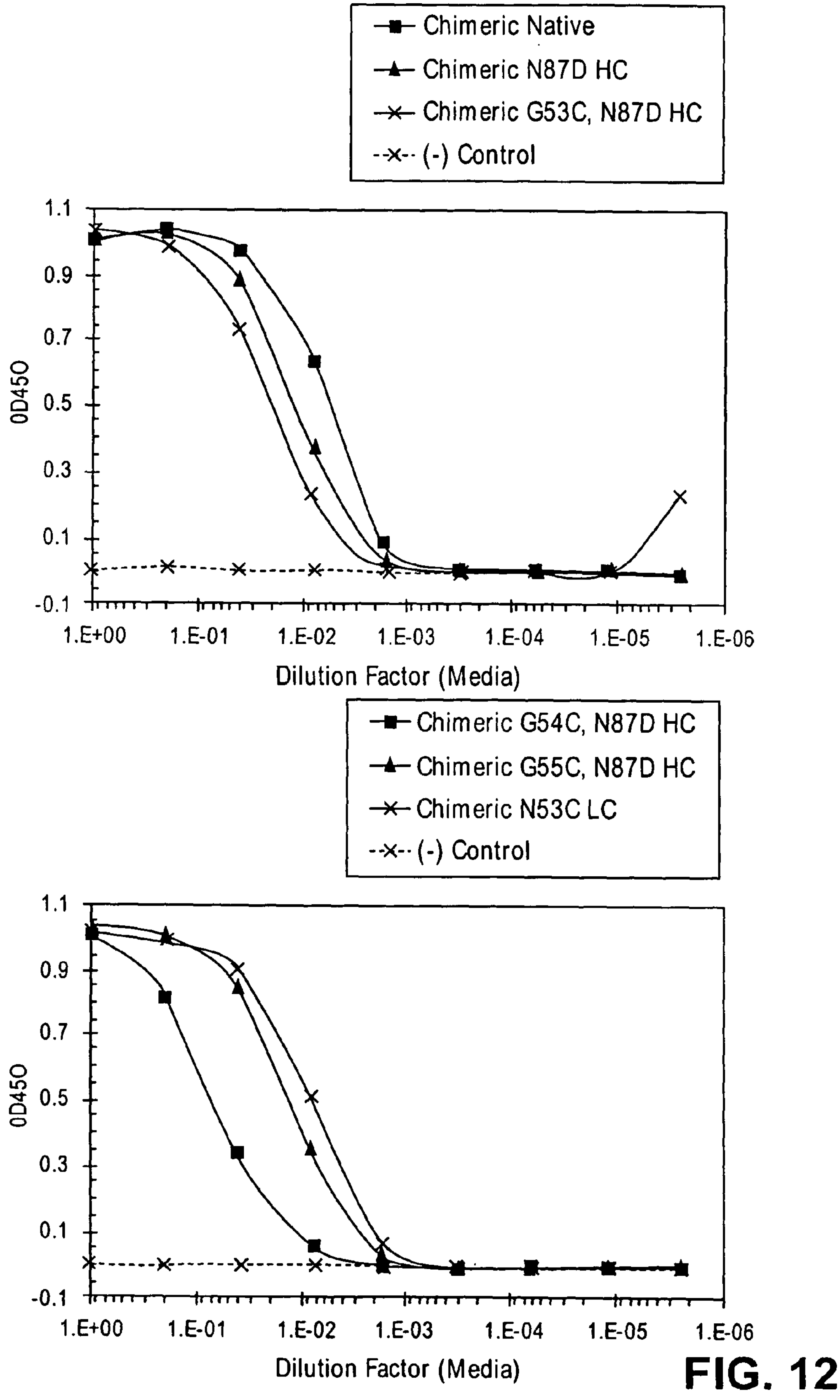
FIG. 12 is a graphical display showing binding of stably transfected *Drosophila* S2 cells expressing the chimeric 2D12.5 Fab gene products (native and site-directed cysteine mutants) to Y-DOTA. Binding curves were determined from non-competitive ELISA assays incorporating dilutions of media containing expressed gene products. The relative amound of expressed chimeric Fab were measured using anti-V5 epitope-HRP conjugate and a chemiluminescent substrate.

Stably transfected *Drosophila* S2 cells expressing the chimeric 2D12.5 FaB gene products (native and site-directed cysteine mutants) were evaluated for their ability to bind Y-DOTA. Binding curves were determined from non-competitive ELISA assays incorporating dilutions of media containing expressed gene products. The relative amound of expressed chimeric Fab were measured using anti-V5 epitope-HRP conjugate and a chemiluminescent substrate. The results are shown in FIG. 12.

Example 3

To determine the metal selectivity of the antibody 2D12.5, a competitive immunoassays was used to measure the binding constants of multiple metal-DOTA complexes relative to $Y^{3+}$-DOTA.

We examined the monoclonal antibody 2D12.5, initially developed to bind specifically to Y-DOTA for targeted radiotherapy (see, e.g., Goodwin et al., *Cancer Res.* 54: 5937-5946 (1994)), in order to determine the scope of its activity. To assess the metal selectivity of antibody 2D12.5, a competitive immunoassay to measure the binding constants of various metal-DOTA complexes relative to the original $Y^{3+}$ complex was developed (FIG. 12). Briefly, 2D12.5 was incubated at 37° C. in the presence of immobilized Y-DOTA and a soluble metal-DOTA competitor. The metal-DOTA concentration was varied from μM to pM in order to determine the relative binding affinity of 2D12.5 for each metal chelate in comparison to Y-DOTA. Binding was measured by standard methods known to those of skill in the art. The DOTA analog used to evaluate binding was [S]-2-(p-nitrobenzyl)-DOTA, which is similar to the original antigen.

We found that 2D12.5 binds not only Y-DOTA but also DOTA complexes of all the lanthanides. Surprisingly, some metal chelates such as Gd-DOTA bind more tightly than the original $Y^{3+}$ complex; overall, the dissociation constants fall within a factor of 3 above or below the Kd=10 nM value for Y-DOTA. Other antibodies that bind metal chelates do so with a strong preference for one or possibly two metals (see, e.g., Love et al., *Biochemistry* 32: 10950-10959 (1993) and Khosraviani et al., *Bioconjugate Chem.* 11: 267-277 (2000)).

Figure 13:
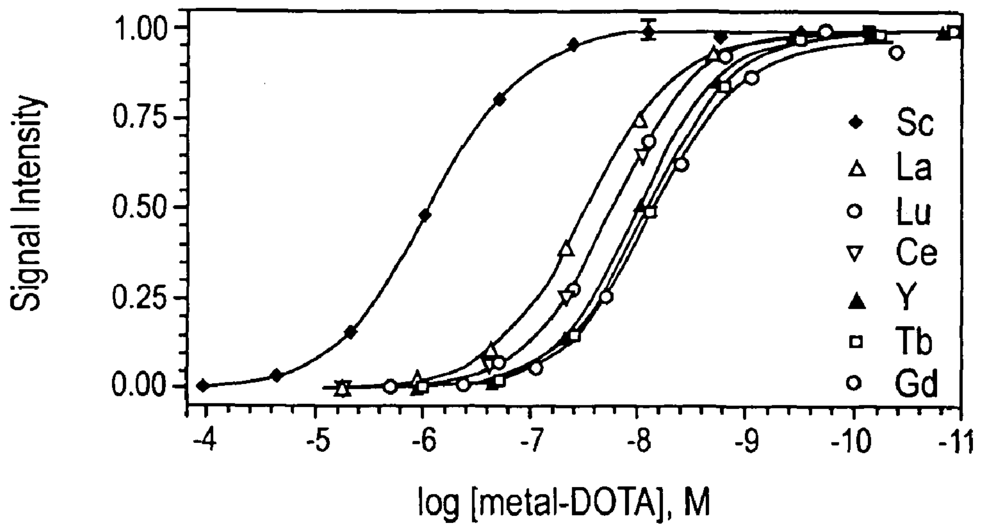
FIG. 13 is graphical display showing the relative binding of metal-DOTA complexes to antibody 2D12.5. A representative set of competitive binding curves obtained from ELISA experiments described in Example 3 below. Error bars (representing the standard error of the mean) are shown, but are generally smaller than the data points.
Figure 14:
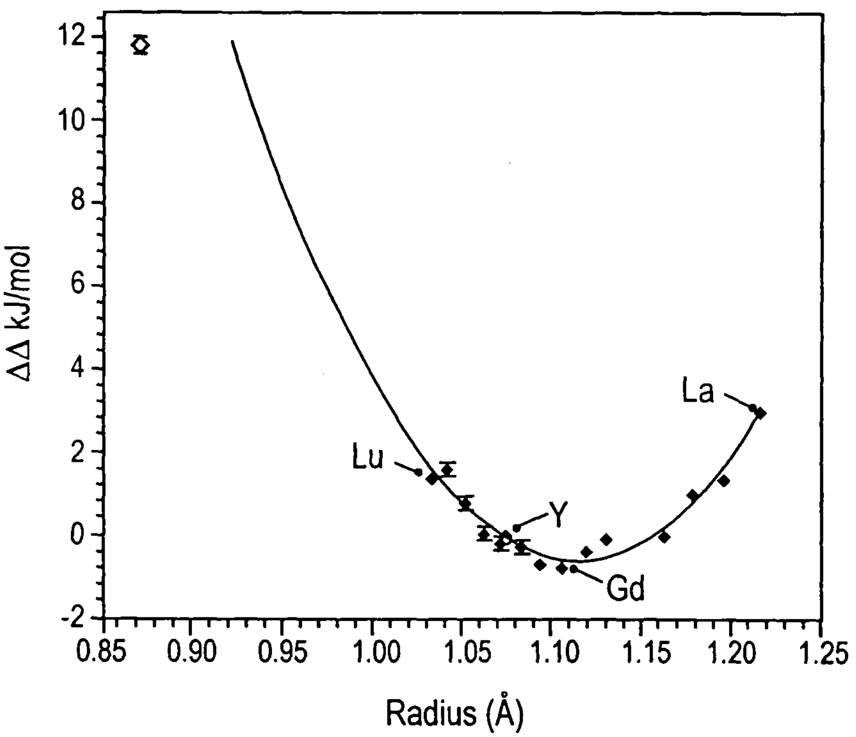
FIG. 14 is a graphical display showing the dependence of the standard Gibbs Free Energy of binding on rare earth ionic radius shows thermodynamically elastic binding behavior between antibody 2D12.5 and rare earth-DOTA complexes. Elements plotted in the order Sc (open circle), Lu, Yb, Tm, Er, Ho, Y (open diamond), Dy, Th, Gd, Eu, Sm, Nd, Pr, Ce, La. $\Delta\Delta G$ values relative to Y-DOTA, set at 0. Error bars represent standard error of the mean.
Figure 15:
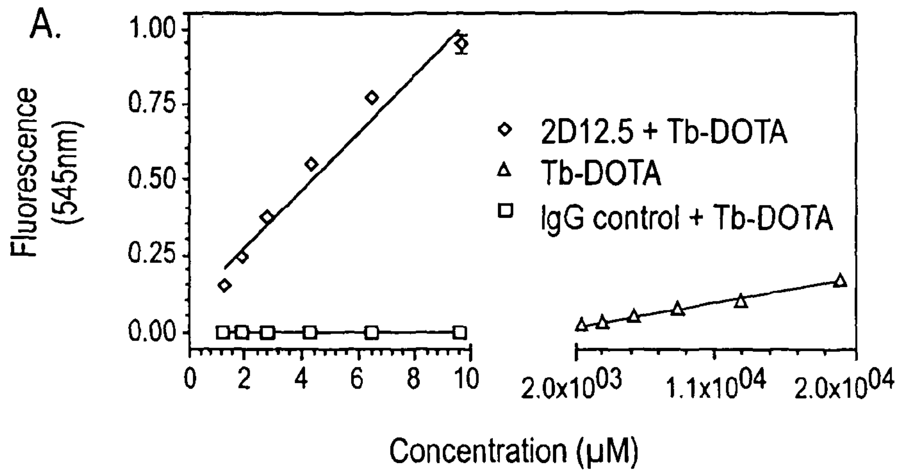
FIG. 15 is a graphical display showing that time-resolved 280 nm excitation yields a marked, linear enhancement in the green 545 nm emission of the Th-DOTA bound to 2D12.5. The enhancement is not observed for Tb-DOTA and a non-binding IgG control.
Figure 16:
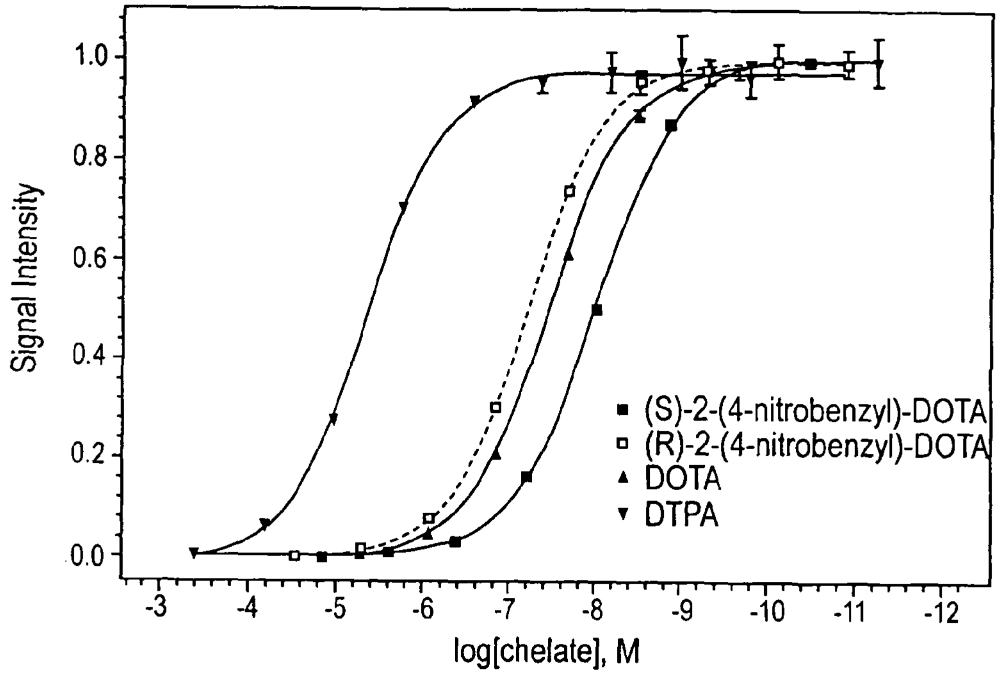
FIG. 16 is a graphical display showing the relative binding curves of 2D12.5 for Y-DOTA isomers and Y-DPTA. 2D12.5 binds both the (R)- and (S) isomers of 2-(4-nitrobenzyl)-DOTA when the coordinated metal is $Y^{3+}$ (the same behavior is expected for the other rare earths). The (S)-isomer confers Λ-helicity, while the (R)-isomer with Δ-helicity, to the acetate arms. The Λ-helicity is observed in the crystal structure for 2D12.5 and is the preferred isomer for binding. However, the antibody tolerates the (R)-isomer with A-helicity, and the affinity decreases less than an order of magnitude as compared to the (S),Λ isomer. Y-DOTA (no-sidearm) exists is solution as a racemic mixutre of the corrdinatoin isomers. As expected, the binding affinity for racemic Y-DOTA is between that observed for the (S)- and (R)-isomers of 2-(4-nitrobenzyl)-DOTA.
Figure 17:
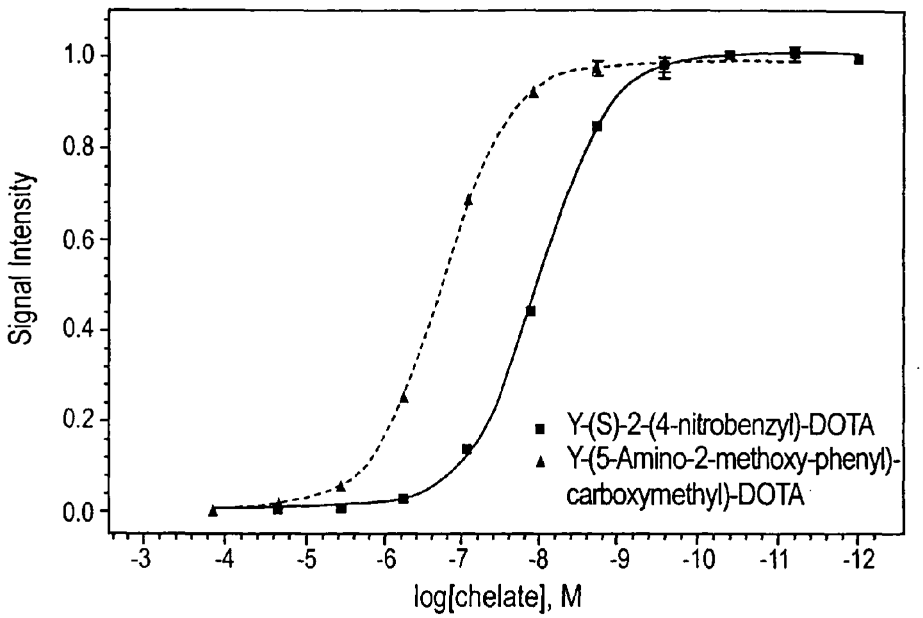
FIG. 17 is a graphical display showing the relative binding curves of Y-DOTA molecules with different sidechain locations. Changing the location of the sidechain of DOTA causes a decrease in the binding affinity, but the affinity of the (5-Amino-2-methoxy-phenyl)-carboxymethyl)-DOTA is still sufficiently strong to consider for further applications. Evaluation of the crystal structure seems to indicate that shorter substitutions at this position may bind with higher affinity. Substitutions at the other locations may yield reasonably high affinities as well. The (5-Amino-2methoxy-phenyl)-carboxymenthyl)-DOTA analyzed in this experiment was racemic, so it is not clear which isomer binds with higher affinity. The low pKa of the carboxymethyl proton makes it difficult to prepare a chirally pure molecule. Substitution as observed in the (S)-2(4-nitrobenzyl)-DOTA is clearly stronger.

The relative binding affinities determined for each rare earth DOTA complex relative to Y-DOTA are plotted as ΔΔG values in FIG. 13. Out of 15 ions tested, we found six rare earth complexes with ΔΔG values more favorable for binding than the original $Y^{3+}$ complex. The radii of the nonacoordinate trivalent lanthanide ions vary in small increments across the series from 1.21 Å ($La^{3+}$) to 1.03 Å ($Lu^{3+}$) (see, e.g., Shannon, R. D. *Acta Crystallogr., Sect. A: Found. Crystallogr. A*32: 751-767 (1976)). Our results show that when the shape of the DOTA complex is perturbed by either increasing or decreasing the radius of the lanthanide ion, the stability of the protein-ligand complex changes in a regular fashion. The effect of the change in ion radius on the standard ΔG of binding should be described approximately by an equation of the form $$\frac{d\Delta G}{dr} = k(r - r_0), \text{ which integrates to } \Delta\Delta G = \frac{1}{2}k(r - r_0)^2.$$

The behavior of ΔΔG as a function of ionic radius fits a parabola, as might be expected for a system that behaves in a thermodynamically elastic way, obeying Hooke's law over a small range of perturbations. The quantitative binding differences allow us to assess the system's flexibility expressed as the force constant k, whose value is ≅50 Nm−1, comparable to a chemical bond. The optimal ionic radius $r_0$ predicted from the parabolic fit to the binding data is 1.11 Å, close to the strongest binders $Tb^{3+}$, $Gd^{3+}$, and $Eu^{3+}$ (1.095, 1.107, and 1.120 Å).

Both Y-DOTA and Gd-DOTA are generally regarded as nonacoordinate, with 4 nitrogens and 4 oxygens from DOTA plus a single coordinated water molecule, in a capped square antiprism arrangement (denoted M). At equilibrium, rare earth DOTA complexes at either end of the lanthanide series differ in the layout of the acetate arms, and mixtures of isomers ranging from M to a distorted inverted antiprism (m) are observed for some. The ionic radius and geometry of the complex also affect the accessibility of the ninth coordination site for water (see, e.g., Aime et al., *Inorg. Chem.* 36: 2059-2068 (1997) and Cosentino et al., *Am. Chem. Soc.* 124: 4901-4909 (2002)). Large La-DOTA is almost exclusively isomer m, while small Lu-DOTA is predominantly isomer M. We suspect that these conformational equilibria play a role in the different binding affinities observed here. Even though $Sc^{3+}$ generally exhibits similar coordination geometries to the rare earths (see, e.g., Zhang et al., *Acta Crystallogr., Sect. C: Cryst. Struct. Commun.* 55: 1418-1420 (1999), Sc-DOTA does not fit well on the optimal parabola for the lanthanides, perhaps because it has a much smaller ionic radius (0.867 Å) (see, e.g., Meehan et al. *Chem. Rev.* 181: 121-145 (1999)).

The broad specificity and high affinity of this antibody for all rare earth-DOTA complexes make it particularly interesting for applications that take advantage of the unique characteristics of lanthanides. For example, Simeonov et al. have recently described blue-fluorescent antibodies, potential sensors that change the emission of a stilbene ligand upon antibody binding (see, Simeonov, et al., *Science* 290: 307-313 (2000)). UV excitation of the Tb-DOTA-2D12.5 complex leads to energy transfer from aromatic side chains of the antibody to bound Tb-DOTA, enhancing green terbium luminescence by approximately four orders of magnitude relative to unbound Tb-DOTA (FIG. 3). The enhancement is comparable to that observed for $Ca^{2+}$ binding proteins, which also transfer energy from aromatic side chains to $Tb^{3+}$ ions bound in $Ca^{2+}$ sites (see, e.g., Hogue et al., *J. Biol. Chem.* 267: 13340-13347 (1992)). Sensors based on lanthanide luminescence exhibit millisecond emission lifetimes, which makes them useful for a number of biological applications (see, e.g., Parker et al., *Chem. Rev.,* 102: 1977-2010 (2002)).

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A method of treating a subject with cancer by administration of a macrocyclic metal chelate, said method comprising the steps of:

(a) administering to said subject an antibody comprising an antigen recognition domain that recognizes said macrocyclic metal chelate, wherein said antibody comprises:

i) a light chain comprising:

a) a first CDR having the sequence of SEQ ID NO:2;

b) a second CDR having a sequence selected from the group consisting of:

i) SEQ ID NO:3; and ii) SEQ ID NO:3 containing a cysteine substitution wherein position 2 is substituted by a cysteine;

c) a third CDR having the sequence of SEQ ID NO:4;

ii) a heavy chain comprising:

a) a first CDR having the sequence of SEQ ID NO:6;

b) a second CDR having a sequence selected from the group consisting of:

i) SEQ ID NO:7;

ii) SEQ ID NO: 7 containing a cysteine substitution wherein position 5 has been substituted by a cysteine;

iii) SEQ ID NO:7 containing a cysteine substitution wherein position 6 has been substituted by a cysteine; and iv) SEQ ID NO:7 containing a cysteine substitution wherein position 7 has been substituted by a cysteine;

c) a third CDR having the sequence of SEQ ID NO:8; wherein said antibody comprises at least one of said cysteine substitutions, and wherein said antibody binds substituted or unsubstituted 1,4,7,10-tetraazacyclododecane-N,N',N",N'"-tetraacetic acid (DOTA); and a targeting moiety that binds specifically to a cancer cell by binding with a member selected from a cell surface receptor and cell surface antigen, thereby forming a cell-antibody complex; and (b) administering to said subject said macrocyclic metal chelate, wherein the macrocyclic metal chelate is a substituted or unsubstituted 1,4,7,10-tetraazacyclododecane-N,N',N"N'"-tetraacetic acid (DOTA) complexed to a metal ion.

2. The method of claim 1, wherein said substituted or unsubstituted 1,4,7,10-tetraazacyclododecane-N,N',N",N'"-tetraacetic acid (DOTA) has the formula:

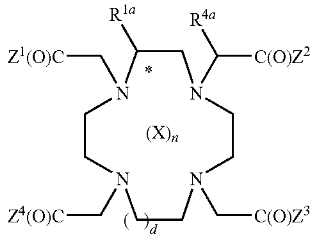

wherein $R^{1a}$ and $R^{4a}$ are members independently selected from H, substituted or unsubstituted alkyl, substituted or unsubstituted heteroalkyl, substituted or unsubstituted aryl and linker moieties;

X is a member selected from a lanthanide ion, an actinide ion, an alkaline earth metal ion, and a group IIIb transition metal ion;

$Z^1$, $Z^2$, $Z^3$ and $Z^4$ are members independently selected from $OR^1$ and $NR^1R^2$ in which $R^1$ and $R^2$ are members independently selected from H, substituted or unsubstituted alkyl and substituted or unsubstituted heteroalkyl;

n is a member selected from 0 and 1.

3. The method of claim 2, wherein the carbon atom marked * is of S configuration.

4. The method of claim 1, wherein said targeting moiety binds specifically to said cell surface antigen.

5. The method of claim 1, wherein the targeting moiety is covalently attached to said antibody.

6. The method of claim 4, wherein the targeting moiety is a second antibody.

7. The method of claim 5, wherein the targeting moiety specifically binds to a protein on a cancer cell.

8. The method of claim 1, wherein the subject is a mammal.

9. The method of claim 8, wherein the mammal is a human.

10. The method according to claim 1 wherein said antibody has the structure:

$$(Ab)_{n'}\text{-L-T}$$

wherein, n' is an integer selected from 1 to 10;

Ab represents said antibody;

L is a member selected from a chemical bond and a linking group that may contain one or more functional groups; and T is said targeting moiety.

11. The method of claim 10, wherein said targeting moiety is a second antibody that binds specifically to a cell surface antigen.

12. The method according to claim 10 wherein said antibody is administered to said subject as a pharmaceutical composition comprising said antibody and a pharmaceutically acceptable carrier.

13. The method according to claim 2, wherein $R^{1a}$ and $R^{4a}$ are H;

$Z^1$, $Z^2$, $Z^3$ and $Z^4$ are OH;

and n is 1.

14. The method according to claim 13, wherein said targeting moiety is a second antibody that binds specifically to a cell surface antigen.

15. The method according to claim 14, wherein said targeting moiety is anti-CEA.

16. The method according to claim 13, wherein said targeting moiety is anti-CEA.

17. The method according to claim 2, wherein $R^{1a}$ is a member independently selected from substituted or unsubstituted alkyl, substituted or unsubstituted heteroalkyl, substituted or unsubstituted aryl and linker moieties.

18. The method according to claim 2, wherein $R^{4a}$ is a member independently selected from substituted or unsubstituted alkyl, substituted or unsubstituted heteroalkyl, substituted or unsubstituted aryl and linker moieties.

19. The method according to claim 2, wherein said DOTA further comprises an arylalkyl moiety having a structure according to the formula:

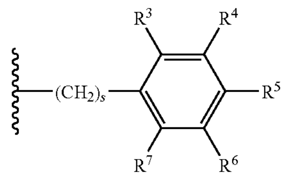

wherein $R^c$ is an unsubstituted unbranched alkyl linker;

$R^3$, $R^4$, $R^5$, $R^6$ and $R^7$ are members independently selected from H, halogen, $NO_2$, CN, $X^1R^8$, $NR^9R^{10}$, and $C(X^2)R^{11}$, wherein $X^1$ is a member selected from O, NH, and S;

$X^2$ is a member selected from O, S, and NH;

$R^8$ and $R^9$ are members independently selected from H, substituted or unsubstituted alkyl, substituted or unsubstituted heteroalkyl, substituted or unsubstituted heteroalkyl and $C(Z^3)R^{12}$ wherein $Z^3$ is a member selected from O, S and NH;

$R^{12}$ is a member selected from substituted or unsubstituted alkyl, substituted or unsubstituted heteroalkyl and $OR^{13}$ wherein $R^{13}$ is a member selected from substituted or unsubstituted alkyl, substituted or unsubstituted heteroalkyl, substituted or unsubstituted aryl, and substituted or unsubstituted heteroaryl;

$R^{10}$ is a member selected from H, substituted or unsubstituted alkyl, substituted or unsubstituted heteroalkyl, and OH, and $R^9$ and $R^{10}$ taken together are optionally (=C=S);

$R^{11}$ is a member selected from H, halogen, substituted or unsubstituted alkyl, substituted or unsubstituted heteroalkyl, $OR^{14}$, and $NR^{15}R^{16}$, wherein $R^{14}$ is a member selected from H, substituted or unsubstituted alkyl, substituted or unsubstituted heteroalkyl, and $C(O)R^{17}$, wherein $R^{17}$ is a member selected from substituted or unsubstituted alkyl, and substituted or unsubstituted heteroalkyl; and $R^{15}$ and $R^{16}$ are members independently selected from H, substituted or unsubstituted alkyl, and substituted or unsubstituted heteroalkyl.

* * * * *

SEQUENCE LISTING

```
<160> NUMBER OF SEQ ID NOS: 72

<210> SEQ ID NO 1
<211> LENGTH: 110
<212> TYPE: PRT
<213> ORGANISM: Mus musculus
```

-continued

<220> FEATURE:
<223> OTHER INFORMATION: murine monoclonal antibody 2D12.5 light chain
variable domain (VL)

<400> SEQUENCE: 1

Gln Ala Val Val Thr Gln Glu Ser Ala Leu Thr Thr Ser Pro Gly Glu
1 5 10 15

Thr Val Thr Leu Thr Cys Arg Ser Ser Thr Gly Ala Val Thr Thr Ser
20 25 30

Asn Tyr Ala Asn Trp Val Gln Glu Lys Pro Asp His Leu Phe Thr Gly
35 40 45

Leu Ile Gly Gly Asn Asn Asn Arg Pro Pro Gly Val Pro Ala Arg Phe
50 55 60

Ser Gly Ser Leu Ile Gly Asp Lys Ala Ala Leu Thr Ile Ala Gly Thr
65 70 75 80

Gln Thr Glu Asp Glu Ala Ile Tyr Phe Cys Ala Leu Trp Tyr Ser Asn
85 90 95

His Trp Val Phe Gly Gly Gly Thr Arg Leu Thr Val Leu Gly
100 105 110

<210> SEQ ID NO 2
<211> LENGTH: 14
<212> TYPE: PRT
<213> ORGANISM: Mus musculus
<220> FEATURE:
<223> OTHER INFORMATION: murine monoclonal antibody 2D12.5 light chain
variable domain (VL) complementarity
determining region 1 (CDR1)

<400> SEQUENCE: 2

Arg Ser Ser Thr Gly Ala Val Thr Thr Ser Asn Tyr Ala Asn
1 5 10

<210> SEQ ID NO 3
<211> LENGTH: 7
<212> TYPE: PRT
<213> ORGANISM: Mus musculus
<220> FEATURE:
<223> OTHER INFORMATION: murine monoclonal antibody 2D12.5 light chain
variable domain (VL) complementarity
determining region 2 (CDR2)

<400> SEQUENCE: 3

Gly Asn Asn Asn Arg Pro Pro
1 5

<210> SEQ ID NO 4
<211> LENGTH: 9
<212> TYPE: PRT
<213> ORGANISM: Mus musculus
<220> FEATURE:
<223> OTHER INFORMATION: murine monoclonal antibody 2D12.5 light chain
variable domain (VL) complementarity
determining region 3 (CDR3)

<400> SEQUENCE: 4

Ala Leu Trp Tyr Ser Asn His Trp Val
1 5

<210> SEQ ID NO 5
<211> LENGTH: 119
<212> TYPE: PRT
<213> ORGANISM: Mus musculus -continued
<220> FEATURE:
<223> OTHER INFORMATION: murine monoclonal antibody 2D12.5 heavy chain
variable domain (VH)

<400> SEQUENCE: 5

Gln Val Lys Leu Gln Glu Ser Gly Pro Gly Leu Val Gln Pro Ser Gln
1 5 10 15

Ser Leu Ser Ile Thr Cys Thr Val Ser Gly Phe Ser Leu Thr Asp Tyr
20 25 30

Gly Val His Trp Val Arg Gln Ser Pro Gly Lys Gly Leu Glu Trp Leu
35 40 45

Gly Val Ile Trp Ser Gly Gly Gly Thr Ala Tyr Thr Ala Ala Phe Ile
50 55 60

Ser Arg Leu Asn Ile Tyr Lys Asp Asn Ser Lys Asn Gln Val Phe Phe
65 70 75 80

Glu Met Asn Ser Leu Gln Ala Asn Asp Thr Ala Met Tyr Tyr Cys Ala
85 90 95

Arg Arg Gly Ser Tyr Pro Tyr Asn Tyr Phe Asp Val Trp Gly Gln Gly
100 105 110

Thr Thr Val Thr Val Ser Ser
115

<210> SEQ ID NO 6
<211> LENGTH: 5
<212> TYPE: PRT
<213> ORGANISM: Mus musculus
<220> FEATURE:
<223> OTHER INFORMATION: murine monoclonal antibody 2D12.5 heavy chain
variable domain (VH) complementarity
determining region 1 (CDR1)

<400> SEQUENCE: 6

Asp Tyr Gly Val His
1 5

<210> SEQ ID NO 7
<211> LENGTH: 16
<212> TYPE: PRT
<213> ORGANISM: Mus musculus
<220> FEATURE:
<223> OTHER INFORMATION: murine monoclonal antibody 2D12.5 heavy chain
variable domain (VH) complementarity
determining region 2 (CDR2)

<400> SEQUENCE: 7

Val Ile Trp Ser Gly Gly Gly Thr Ala Tyr Thr Ala Ala Phe Ile Ser
1 5 10 15

<210> SEQ ID NO 8
<211> LENGTH: 11
<212> TYPE: PRT
<213> ORGANISM: Mus musculus
<220> FEATURE:
<223> OTHER INFORMATION: murine monoclonal antibody 2D12.5 heavy chain
variable domain (VH) complementarity
determining region 3 (CDR3)

<400> SEQUENCE: 8

Arg Gly Ser Tyr Pro Tyr Asn Tyr Phe Asp Val
1 5 10

-continued

<210> SEQ ID NO 9
<211> LENGTH: 118
<212> TYPE: PRT
<213> ORGANISM: Mus musculus
<220> FEATURE:
<223> OTHER INFORMATION: native hybridoma murine 2D12.5 heavy chain variable region (VH)

<400> SEQUENCE: 9

```
Val Lys Leu Gln Glu Ser Gly Pro Gly Leu Val Gln Pro Ser Gln Ser
  1               5                  10                  15

Leu Ser Ile Thr Cys Thr Val Ser Gly Phe Ser Leu Thr Asp Tyr Gly
             20                  25                  30

Val His Trp Val Arg Gln Ser Pro Gly Lys Gly Leu Glu Trp Leu Gly
         35                  40                  45

Val Ile Trp Ser Gly Gly Gly Thr Ala Tyr Thr Ala Ala Phe Ile Ser
     50                  55                  60

Arg Leu Asn Ile Tyr Lys Asp Asn Ser Lys Asn Gln Val Phe Phe Glu
 65                  70                  75                  80

Met Asn Ser Leu Gln Ala Asn Asp Thr Ala Met Tyr Tyr Cys Ala Arg
                 85                  90                  95

Arg Gly Ser Tyr Pro Tyr Asn Tyr Phe Asp Val Trp Gly Gln Gly Thr
            100                 105                 110

Thr Val Thr Val Ser Ser
        115
```

<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence:native cloned hybridoma murine 2D12.5 heavy chain variable region (VH)

<400> SEQUENCE: 10

```
Val Lys Leu Gln Glu Ser Gly Pro Gly Leu Val Gln Pro Ser Gln Ser
  1               5                  10                  15

Leu Ser Ile Thr Cys Thr Val Ser Gly Phe Ser Leu Thr Asp Tyr Gly
             20                  25                  30

Val His Trp Val Arg Gln Ser Pro Gly Lys Gly Leu Glu Trp Leu Gly
         35                  40                  45

Val Ile Trp Ser Gly Gly Gly Thr Ala Tyr Thr Ala Ala Phe Ile Ser
     50                  55                  60

Arg Leu Asn Ile Tyr Lys Asp Asn Ser Lys Asn Gln Val Phe Phe Glu
 65                  70                  75                  80

Met Asn Ser Leu Gln Ala Asn Asp Thr Ala Met Tyr Tyr Cys Ala Arg
                 85                  90                  95

Arg Gly Ser Tyr Pro Tyr Asn Tyr Phe Asp Val Trp Gly Gln Gly Thr
            100                 105                 110

Thr Val Thr Val Ser Ala
        115
```

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence:N87D cloned mutant murine 2D12.5 heavy chain variable region (VH)

-continued

<400> SEQUENCE: 11

```
Val Lys Leu Gln Glu Ser Gly Pro Gly Leu Val Gln Pro Ser Gln Ser
  1               5                  10                  15

Leu Ser Ile Thr Cys Thr Val Ser Gly Phe Ser Leu Thr Asp Tyr Gly
             20                  25                  30

Val His Trp Val Arg Gln Ser Pro Gly Lys Gly Leu Glu Trp Leu Gly
         35                  40                  45

Val Ile Trp Ser Gly Gly Gly Thr Ala Tyr Thr Ala Ala Phe Ile Ser
     50                  55                  60

Arg Leu Asn Ile Tyr Lys Asp Asn Ser Lys Asn Gln Val Phe Phe Glu
 65                  70                  75                  80

Met Asn Ser Leu Gln Ala Asp Asp Thr Ala Met Tyr Tyr Cys Ala Arg
                 85                  90                  95

Arg Gly Ser Tyr Pro Tyr Asn Tyr Phe Asp Val Trp Gly Gln Gly Thr
            100                 105                 110

Thr Val Thr Val Ser Ala
        115
```

<210> SEQ ID NO 12
<211> LENGTH: 118
<212> TYPE: PRT
<213> ORGANISM: Artificial Sequence
<220> FEATURE:
<223> OTHER INFORMATION: Description of Artificial Sequence:N87D G53C cloned mutant murine 2D12.5 heavy chain variable region (VH)

<400> SEQUENCE: 12

```
Val Lys Leu Gln Glu Ser Gly Pro Gly Leu Val Gln Pro Ser Gln Ser
  1               5                  10                  15

Leu Ser Ile Thr Cys Thr Val Ser Gly Phe Ser Leu Thr Asp Tyr Gly
             20                  25                  30

Val His Trp Val Arg Gln Ser Pro Gly Lys Gly Leu Glu Trp Leu Gly
         35                  40                  45

Val Ile Trp Ser Cys Gly Gly Thr Ala Tyr Thr Ala Ala Phe Ile Ser
     50                  55                  60

Arg Leu Asn Ile Tyr Lys Asp Asn Ser Lys Asn Gln Val Phe Phe Glu
 65                  70                  75                  80

Met Asn Ser Leu Gln Ala Asp Asp Thr Ala Met Tyr Tyr Cys Ala Arg
                 85                  90                  95

Arg Gly Ser Tyr Pro Tyr Asn Tyr Phe Asp Val Trp Gly Gln Gly Thr
            100                 105                 110

Thr Val Thr Val Ser Ala
        115
```

<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence:N87D G54C cloned mutant murine 2D12.5 heavy chain variable region (VH)

<400> SEQUENCE: 13

```
Val Lys Leu Gln Glu Ser Gly Pro Gly Leu Val Gln Pro Ser Gln Ser
  1               5                  10                  15

Leu Ser Ile Thr Cys Thr Val Ser Gly Phe Ser Leu Thr Asp Tyr Gly
             20                  25                  30
```

-continued

```
Val His Trp Val Arg Gln Ser Pro Gly Lys Gly Leu Glu Trp Leu Gly
        35                  40                  45

Val Ile Trp Ser Gly Cys Gly Thr Ala Tyr Thr Ala Ala Phe Ile Ser
    50                  55                  60

Arg Leu Asn Ile Tyr Lys Asp Asn Ser Lys Asn Gln Val Phe Phe Glu
65                  70                  75                  80

Met Asn Ser Leu Gln Ala Asp Asp Thr Ala Met Tyr Tyr Cys Ala Arg
                85                  90                  95

Arg Gly Ser Tyr Pro Tyr Asn Tyr Phe Asp Val Trp Gly Gln Gly Thr
            100                 105                 110

Thr Val Thr Val Ser Ala
        115
```

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence:N87D G55C cloned mutant murine 2D12.5 heavy chain variable region (VH)

<400> SEQUENCE: 14

```
Val Lys Leu Gln Glu Ser Gly Pro Gly Leu Val Gln Pro Ser Gln Ser
1               5                   10                  15

Leu Ser Ile Thr Cys Thr Val Ser Gly Phe Ser Leu Thr Asp Tyr Gly
            20                  25                  30

Val His Trp Val Arg Gln Ser Pro Gly Lys Gly Leu Glu Trp Leu Gly
        35                  40                  45

Val Ile Trp Ser Gly Gly Cys Thr Ala Tyr Thr Ala Ala Phe Ile Ser
    50                  55                  60

Arg Leu Asn Ile Tyr Lys Asp Asn Ser Lys Asn Gln Val Phe Phe Glu
65                  70                  75                  80

Met Asn Ser Leu Gln Ala Asp Asp Thr Ala Met Tyr Tyr Cys Ala Arg
                85                  90                  95

Arg Gly Ser Tyr Pro Tyr Asn Tyr Phe Asp Val Trp Gly Gln Gly Thr
            100                 105                 110

Thr Val Thr Val Ser Ala
        115
```

<210> SEQ ID NO 15
<211> LENGTH: 354
<212> TYPE: DNA
<213> ORGANISM: Mus musculus
<220> FEATURE:
<223> OTHER INFORMATION: native hybridoma murine 2D12.5 heavy chain variable region (VH)

<400> SEQUENCE: 15

```
gtgaagctgc aggagtcagg acctggccta gtgcagccct cacagagcct gtccatcacc     60

tgcacggtct ctggtttctc attaactgac tatggtgtac actgggttcg ccagtctcca    120

ggaaagggtc tggaatggct gggagtgata tggagtggtg gaggcacggc ctatactgcg    180

gcgttcatat ccagactgaa catctacaag gacaattcca agaaccaagt tttctttgaa    240

atgaacagtc tgcaagctaa tgacacagcc atgtattact gtgccagaag gggtagctac    300

ccttacaact acttcgatgt ctggggccaa gggaccacag tcaccgtctc ctca          354
```

-continued

<210> SEQ ID NO 16
<211> LENGTH: 354
<212> TYPE: DNA
<213> ORGANISM: Artificial Sequence
<220> FEATURE:
<223> OTHER INFORMATION: Description of Artificial Sequence:native cloned hybridoma murine 2D12.5 heavy chain variable region (VH)

<400> SEQUENCE: 16

```
gtgaagctgc aggagtctgg acctggccta gtgcagccct cacagagcct gtccatcacc     60

tgcacggtct ctggtttctc attaactgac tatggtgtac actgggttcg ccagtctcca    120

ggaaagggtc tggaatggct gggagtgata tggagtggtg gaggcacggc ctatactgcg    180

gcgttcatat ccagactgaa catctacaag gacaattcca agaaccaagt tttctttgaa    240

atgaacagtc tgcaagctaa tgacacagcc atgtattact gtgccagaag gggtagctac    300

ccttacaact acttcgatgt ctggggccaa gggaccacgg tcaccgtctc cgca          354
```

<210> SEQ ID NO 17
<211> LENGTH: 354
<212> TYPE: DNA
<213> ORGANISM: Artificial Sequence
<220> FEATURE:
<223> OTHER INFORMATION: Description of Artificial Sequence:N87D cloned mutant murine 2D12.5 heavy chain variable region (VH)

<400> SEQUENCE: 17

```
gtgaagctgc aggagtctgg acctggccta gtgcagccct cacagagcct gtccatcacc     60

tgcacggtct ctggtttctc attaactgac tatggtgtac actgggttcg ccagtctcca    120

ggaaagggtc tggaatggct gggagtgata tggagtggtg gaggcacggc ctatactgcg    180

gcgttcatat ccagactgaa catctacaag gacaattcca agaaccaagt tttctttgaa    240

atgaacagtc tgcaagctga tgacacagcc atgtattact gtgccagaag gggtagctac    300

ccttacaact acttcgatgt ctggggccaa gggaccacgg tcaccgtctc cgca          354
```

<210> SEQ ID NO 18
<211> LENGTH: 354
<212> TYPE: DNA
<213> ORGANISM: Artificial Sequence
<220> FEATURE:
<223> OTHER INFORMATION: Description of Artificial Sequence:N87D G53C cloned mutant murine 2D12.5 heavy chain variable region (VH)

<400> SEQUENCE: 18

```
gtgaagctgc aggagtctgg acctggccta gtgcagccct cacagagcct gtccatcacc     60

tgcacggtct ctggtttctc attaactgac tatggtgtac actgggttcg ccagtctcca    120

ggaaagggtc tggaatggct gggagtgata tggagttgtg gaggcacggc ctatactgcg    180

gcgttcatat ccagactgaa catctacaag gacaattcca agaaccaagt tttctttgaa    240

atgaacagtc tgcaagctga tgacacagcc atgtattact gtgccagaag gggtagctac    300

ccttacaact acttcgatgt ctggggccaa gggaccacgg tcaccgtctc cgca          354
```

<210> SEQ ID NO 19
<211> LENGTH: 354
<212> TYPE: DNA
<213> ORGANISM: Artificial Sequence
<220> FEATURE:
<223> OTHER INFORMATION: Description of Artificial Sequence:N87D G54C cloned mutant murine 2D12.5 heavy chain variable region (VH)

-continued

<400> SEQUENCE: 19
gtgaagctgc aggagtctgg gcctggccta gtgcagccct cacagagcct gtccatcacc 60
tgcacggtct ctggtttctc attaactgac tatggtgtac actgggttcg ccagtctcca 120
ggaaagggtc tggaatggct gggagtgata tggagtggtt gtggcacggc ctatactgcg 180
gcgttcatat ccagactgaa catctacaag gacaattcca agaaccaagt tttctttgaa 240
atgaacagtc tgcaagctga tgacacagcc atgtattact gtgccagaag ggtagctac 300 ccttacaact acttcgatgt ctggggccaa gggaccacgg tcaccgtctc cgca 354

<210> SEQ ID NO 20
<211> LENGTH: 354
<212> TYPE: DNA
<213> ORGANISM: Artificial Sequence
<220> FEATURE:
<223> OTHER INFORMATION: Description of Artificial Sequence:N87D G55C cloned mutant murine 2D12.5 heavy chain variable region (VH)

<400> SEQUENCE: 20
gtgaagctgc aggagtctgg acctggccta gtgcagccct cacagagcct gtccatcacc 60
tgcacggtct ctggtttctc attaactgac tatggtgtac actgggttcg ccagtctcca 120
ggaaagggtc tggaatggct gggagtgata tggagtggtg gatgcacggc ctatactgcg 180
gcgttcatat ccagactgaa catctacaag gacaattcca agaaccaagt tttctttgaa 240
atgaacagtc tgcaagctga tgacacagcc atgtattact gtgccagaag ggtagctac 300 ccttacaact acttcgatgt ctggggccaa gggaccacgg tcaccgtctc cgca 354

<210> SEQ ID NO 21
<211> LENGTH: 109
<212> TYPE: PRT
<213> ORGANISM: Mus musculus
<220> FEATURE:
<223> OTHER INFORMATION: native hybridoma murine 2D12.5 light chain variable region (VL)

<400> SEQUENCE: 21

Ala Val Val Thr Gln Glu Ser Ala Leu Thr Thr Ser Pro Gly Glu Thr
1 5 10 15

Val Thr Leu Thr Cys Arg Ser Ser Thr Gly Ala Val Thr Thr Ser Asn
20 25 30

Tyr Ala Asn Trp Val Gln Glu Lys Pro Asp His Leu Phe Thr Gly Leu
35 40 45

Ile Gly Gly Asn Asn Asn Arg Pro Pro Gly Val Pro Ala Arg Phe Ser
50 55 60

Gly Ser Leu Ile Gly Asp Lys Ala Ala Leu Thr Ile Ala Gly Thr Gln
65 70 75 80

Thr Glu Asp Glu Ala Ile Tyr Phe Cys Ala Leu Trp Tyr Ser Asn His
85 90 95

Trp Val Phe Gly Gly Gly Thr Arg Leu Thr Val Leu Gly
100 105

<210> SEQ ID NO 22
<211> LENGTH: 109
<212> TYPE: PRT
<213> ORGANISM: Artificial Sequence
<220> FEATURE:
<223> OTHER INFORMATION: Description of Artificial Sequence:native cloned hybridoma murine 2D12.5 light chain variable region (VL)

-continued

<400> SEQUENCE: 22

```
Ala Val Val Thr Gln Glu Ser Ala Leu Thr Thr Ser Pro Gly Glu Thr
  1             5                  10                  15

Val Thr Leu Thr Cys Arg Ser Ser Thr Gly Ala Val Thr Thr Ser Asn
             20                  25                  30

Tyr Ala Asn Trp Val Gln Glu Lys Pro Asp His Leu Phe Thr Gly Leu
         35                  40                  45

Ile Gly Gly Asn Asn Asn Arg Pro Pro Gly Val Pro Ala Arg Phe Ser
     50                  55                  60

Gly Ser Leu Ile Gly Asp Lys Ala Ala Leu Thr Ile Ala Gly Thr Gln
 65                  70                  75                  80

Thr Glu Asp Glu Ala Ile Tyr Phe Cys Ala Leu Trp Tyr Ser Asn His
                 85                  90                  95

Trp Val Phe Gly Gly Gly Thr Lys Leu Thr Val Leu Ser
            100                 105
```

<210> SEQ ID NO 23
<211> LENGTH: 109
<212> TYPE: PRT
<213> ORGANISM: Artificial Sequence
<220> FEATURE:
<223> OTHER INFORMATION: Description of Artificial Sequence:N53C cloned mutant murine 2D12.5 light chain variable region (VL)

<400> SEQUENCE: 23

```
Ala Val Val Thr Gln Glu Ser Ala Leu Thr Thr Ser Pro Gly Glu Thr
  1             5                  10                  15

Val Thr Leu Thr Cys Arg Ser Ser Thr Gly Ala Val Thr Thr Ser Asn
             20                  25                  30

Tyr Ala Asn Trp Val Gln Glu Lys Pro Asp His Leu Phe Thr Gly Leu
         35                  40                  45

Ile Gly Gly Cys Asn Asn Arg Pro Pro Gly Val Pro Ala Arg Phe Ser
     50                  55                  60

Gly Ser Leu Ile Gly Asp Lys Ala Ala Leu Thr Ile Ala Gly Thr Gln
 65                  70                  75                  80

Thr Glu Asp Glu Ala Ile Tyr Phe Cys Ala Leu Trp Tyr Ser Asn His
                 85                  90                  95

Trp Val Phe Gly Gly Gly Thr Lys Leu Thr Val Leu Ser
            100                 105
```

<210> SEQ ID NO 24
<211> LENGTH: 327
<212> TYPE: DNA
<213> ORGANISM: Mus musculus
<220> FEATURE:
<223> OTHER INFORMATION: native hybridoma murine 2D12.5 light chain variable region (VL)

<400> SEQUENCE: 24

```
gctgttgtga ctcaggaatc tgcactcacc acatcacctg gtgaaacagt cacactcact     60

tgtcgctcaa gtactggggc tgttacgact agtaactatg ccaactgggt ccaagagaaa    120

ccagatcatt tattcactgg tctaataggt ggtaataata accgacctcc aggtgttcct    180

gccagattct caggctccct gattggagac aaggctgccc tcaccatcgc agggacacag    240

actgaggatg aggcaatata tttctgtgct ctatggtaca gcaaccattg ggtgttcggt    300

ggaggaacca gactgactgt cctaggc                                        327
```

<210> SEQ ID NO 25
<211> LENGTH: 327
<212> TYPE: DNA
<213> ORGANISM: Artificial Sequence
<220> FEATURE:
<223> OTHER INFORMATION: Description of Artificial Sequence:native cloned hybridoma murine 2D12.5 light chain variable region (VL)

<400> SEQUENCE: 25

```
gctgttgtga ctcaggaatc tgcactcacc acatcacctg gtgaaacagt cacactcact     60

tgtcgctcaa gtactggggc tgttacgact agtaactatg ccaactgggt ccaagagaaa    120

ccagatcatt tattcactgg tctaataggt ggtaataata accgacctcc aggtgttcct    180

gccagattct caggctccct gattggagac aaggctgccc tcaccatcgc agggacacag    240

actgaggatg aggcaatata tttctgtgct ctatggtaca gcaaccattg ggtgttcggt    300

gggggaacca aactgactgt cctaagc                                        327
```

<210> SEQ ID NO 26
<211> LENGTH: 327
<212> TYPE: DNA
<213> ORGANISM: Artificial Sequence
<220> FEATURE:
<223> OTHER INFORMATION: Description of Artificial Sequence:N53C cloned mutant murine 2D12.5 light chain variable region (VL)

<400> SEQUENCE: 26

```
gctgttgtga ctcaggaatc tgcactcacc acatcacctg gtgaaacagt cacactcact     60

tgtcgctcaa gtactggggc tgttacgact agtaactatg ccaactgggt ccaagagaaa    120

ccagatcatt tattcactgg tctaataggt ggttgtaata accgacctcc aggtgttcct    180

gccagattct caggctccct gattggagac aaggctgccc tcaccatcgc agggacacag    240

actgaggatg aggcaatata tttctgtgct ctatggtaca gcaaccattg ggtgttcggt    300

gggggaacca aactgactgt cctaagc                                        327
```

<210> SEQ ID NO 27
<211> LENGTH: 218
<212> TYPE: PRT
<213> ORGANISM: Artificial Sequence
<220> FEATURE:
<223> OTHER INFORMATION: Description of Artificial Sequence:native cloned chimeric murine 2D12.5 light chain variable region (VL) fused to human anti-tetanus toxin antibody kappa light chain constant region (TTCL)

<400> SEQUENCE: 27

```
Arg Ser Ala Val Val Thr Gln Glu Ser Ala Leu Thr Thr Ser Pro Gly
  1               5                  10                  15

Glu Thr Val Thr Leu Thr Cys Arg Ser Ser Thr Gly Ala Val Thr Thr
             20                  25                  30

Ser Asn Tyr Ala Asn Trp Val Gln Glu Lys Pro Asp His Leu Phe Thr
         35                  40                  45

Gly Leu Ile Gly Gly Asn Asn Asn Arg Pro Pro Gly Val Pro Ala Arg
     50                  55                  60

Phe Ser Gly Ser Leu Ile Gly Asp Lys Ala Ala Leu Thr Ile Ala Gly
 65                  70                  75                  80

Thr Gln Thr Glu Asp Glu Ala Ile Tyr Phe Cys Ala Leu Trp Tyr Ser
                 85                  90                  95

Asn His Trp Val Phe Gly Gly Gly Thr Lys Leu Thr Val Leu Ser Arg
            100                 105                 110
```

-continued

```
Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Leu Pro
        195                 200                 205

Val Thr Lys Ser Phe Asn Arg Gly Glu Cys
    210                 215


<210> SEQ ID NO 28
<211> LENGTH: 218
<212> TYPE: PRT
<213> ORGANISM: Artificial Sequence
<220> FEATURE:
<223> OTHER INFORMATION: Description of Artificial Sequence:N53C cloned
      mutant chimeric murine 2D12.5 light chain variable
      region (VL) fused to human anti-tetanus toxin
      antibody kappa light chain constant region (TTCL)

<400> SEQUENCE: 28

Arg Ser Ala Val Val Thr Gln Glu Ser Ala Leu Thr Thr Ser Pro Gly
  1               5                  10                  15

Glu Thr Val Thr Leu Thr Cys Arg Ser Ser Thr Gly Ala Val Thr Thr
            20                  25                  30

Ser Asn Tyr Ala Asn Trp Val Gln Glu Lys Pro Asp His Leu Phe Thr
        35                  40                  45

Gly Leu Ile Gly Gly Cys Asn Asn Arg Pro Pro Gly Val Pro Ala Arg
     50                  55                  60

Phe Ser Gly Ser Leu Ile Gly Asp Lys Ala Ala Leu Thr Ile Ala Gly
 65                  70                  75                  80

Thr Gln Thr Glu Asp Glu Ala Ile Tyr Phe Cys Ala Leu Trp Tyr Ser
                 85                  90                  95

Asn His Trp Val Phe Gly Gly Gly Thr Lys Leu Thr Val Leu Ser Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Leu Pro
        195                 200                 205

Val Thr Lys Ser Phe Asn Arg Gly Glu Cys
    210                 215
```

-continued

<210> SEQ ID NO 29
<211> LENGTH: 109
<212> TYPE: PRT
<213> ORGANISM: Mus musculus
<220> FEATURE:
<223> OTHER INFORMATION: native hybridoma murine 2D12.5 light chain variable region (VL)

<400> SEQUENCE: 29

```
Ala Val Val Thr Gln Glu Ser Ala Leu Thr Thr Ser Pro Gly Glu Thr
  1               5                  10                  15

Val Thr Leu Thr Cys Arg Ser Ser Thr Gly Ala Val Thr Thr Ser Asn
             20                  25                  30

Tyr Ala Asn Trp Val Gln Glu Lys Pro Asp His Leu Phe Thr Gly Leu
         35                  40                  45

Ile Gly Gly Asn Asn Asn Arg Pro Pro Gly Val Pro Ala Arg Phe Ser
     50                  55                  60

Gly Ser Leu Ile Gly Asp Lys Ala Ala Leu Thr Ile Ala Gly Thr Gln
 65                  70                  75                  80

Thr Glu Asp Glu Ala Ile Tyr Phe Cys Ala Leu Trp Tyr Ser Asn His
                 85                  90                  95

Trp Val Phe Gly Gly Gly Thr Arg Leu Thr Val Leu Gly
            100                 105
```

<210> SEQ ID NO 30
<211> LENGTH: 107
<212> TYPE: PRT
<213> ORGANISM: Homo sapiens
<220> FEATURE:
<223> OTHER INFORMATION: human anti-tetanus toxin antibody kappa light chain constant region (TTCL) template

<400> SEQUENCE: 30

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Leu
                 85                  90                  95

Pro Val Thr Lys Ser Phe Asn Arg Gly Glu Cys
            100                 105
```

<210> SEQ ID NO 31
<211> LENGTH: 664
<212> TYPE: DNA
<213> ORGANISM: Artificial Sequence
<220> FEATURE:
<223> OTHER INFORMATION: Description of Artificial Sequence:native cloned chimeric murine 2D12.5 light chain variable region (VL) fused to human anti-tetanus toxin antibody kappa light chain constant region (TTCL)

<400> SEQUENCE: 31

```
agatctgctg ttgtgactca ggaatctgca ctcaccacat cacctggtga aacagtcaca      60

ctcacttgtc gctcaagtac tggggctgtt acgactagta actatgccaa ctgggtccaa     120
```

-continued

```
gagaaaccag atcatttatt cactggtcta ataggtggta ataataaccg acctccaggt    180

gttcctgcca gattctcagg ctccctgatt ggagacaagg ctgccctcac catcgcaggg    240

acacagactg aggatgaggc aatatatttc tgtgctctat ggtacagcaa ccattgggtg    300

ttcggtgggg gaaccaaact gactgtccta agccgaactg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctt gcccgtcaca aagagcttca acaggggaga gtgttaattc    660

taga                                                                 664
```

<210> SEQ ID NO 32
<211> LENGTH: 664
<212> TYPE: DNA
<213> ORGANISM: Artificial Sequence
<220> FEATURE:
<223> OTHER INFORMATION: Description of Artificial Sequence:N53C cloned mutant chimeric murine 2D12.5 light chain variable region (VL) fused to human anti-tetanus toxin antibody kappa light chain constant region (TTCL)

<400> SEQUENCE: 32

```
agatctgctg ttgtgactca ggaatctgca ctcaccacat cacctggtga aacagtcaca     60

ctcacttgtc gctcaagtac tggggctgtt acgactagta actatgccaa ctgggtccaa    120

gagaaaccag atcatttatt cactggtcta ataggtggtt gtaataaccg acctccaggt    180

gttcctgcca gattctcagg ctccctgatt ggagacaagg ctgccctcac catcgcaggg    240

acacagactg aggatgaggc aatatatttc tgtgctctat ggtacagcaa ccattgggtg    300

ttcggtgggg gaaccaaact gactgtccta agccgaactg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gtctgagctt gcccgtcaca aagagcttca acaggggaga gtgttaattc    660

taga                                                                 664
```

<210> SEQ ID NO 33
<211> LENGTH: 327
<212> TYPE: DNA
<213> ORGANISM: Mus musculus
<220> FEATURE:
<223> OTHER INFORMATION: native hybridoma murine 2D12.5 light chain variable region (VL)

<400> SEQUENCE: 33

```
gctgttgtga ctcaggaatc tgcactcacc acatcacctg gtgaaacagt cacactcact     60

tgtcgctcaa gtactggggc tgttacgact agtaactatg ccaactgggt ccaagagaaa    120

ccagatcatt tattcactgg tctaataggt ggtaataata accgacctcc aggtgttcct    180

gccagattct caggctccct gattggagac aaggctgccc tcaccatcgc agggacacag    240

actgaggatg aggcaatata tttctgtgct ctatggtaca gcaaccattg ggtgttcggt    300

ggaggaacca gactgactgt cctaggc                                        327
```

-continued

<210> SEQ ID NO 34
<211> LENGTH: 322
<212> TYPE: DNA
<213> ORGANISM: Homo sapiens
<220> FEATURE:
<223> OTHER INFORMATION: human anti-tetanus toxin antibody kappa light chain constant region (TTCL) template

<400> SEQUENCE: 34

```
cgaactgtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcagc accctgacgc tgagcaaagc agactacgag     240

aaacacaaag tctacgcctg cgaagtcacc catcagggcc tgagcttgcc cgtcacaaag     300

agcttcaaca ggggagagtg tt                                              322
```

<210> SEQ ID NO 35
<211> LENGTH: 227
<212> TYPE: PRT
<213> ORGANISM: Artificial Sequence
<220> FEATURE:
<223> OTHER INFORMATION: Description of Artificial Sequence:native cloned chimeric murine 2D12.5 heavy chain variable region (VH) fused to human anti-tetanus toxin antibody CH1 heavy chain constant region (TTCH)

<400> SEQUENCE: 35

```
Arg Ser Val Lys Leu Gln Glu Ser Gly Pro Gly Leu Val Gln Pro Ser
  1               5                  10                  15

Gln Ser Leu Ser Ile Thr Cys Thr Val Ser Gly Phe Ser Leu Thr Asp
             20                  25                  30

Tyr Gly Val His Trp Val Arg Gln Ser Pro Gly Lys Gly Leu Glu Trp
         35                  40                  45

Leu Gly Val Ile Trp Ser Gly Gly Gly Thr Ala Tyr Thr Ala Ala Phe
     50                  55                  60

Ile Ser Arg Leu Asn Ile Tyr Lys Asp Asn Ser Lys Asn Gln Val Phe
 65                  70                  75                  80

Phe Glu Met Asn Ser Leu Gln Ala Asn Asp Thr Ala Met Tyr Tyr Cys
                 85                  90                  95

Ala Arg Arg Gly Ser Tyr Pro Tyr Asn Tyr Phe Asp Val Trp Gly Gln
            100                 105                 110

Gly Thr Thr Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Ala Glu Pro Lys Ser Cys Asp
    210                 215                 220

Lys Ser Arg
225
```

-continued

<210> SEQ ID NO 36
<211> LENGTH: 227
<212> TYPE: PRT
<213> ORGANISM: Artificial Sequence
<220> FEATURE:
<223> OTHER INFORMATION: Description of Artificial Sequence:N87D cloned
mutant chimeric murine 2D12.5 heavy chain variable
region (VH) fused to human anti-tetanus toxin
antibody CH1 heavy chain constant region (TTCH)

<400> SEQUENCE: 36

```
Arg Ser Val Lys Leu Gln Glu Ser Gly Pro Gly Leu Val Gln Pro Ser
  1               5                  10                  15

Gln Ser Leu Ser Ile Thr Cys Thr Val Ser Gly Phe Ser Leu Thr Asp
             20                  25                  30

Tyr Gly Val His Trp Val Arg Gln Ser Pro Gly Lys Gly Leu Glu Trp
         35                  40                  45

Leu Gly Val Ile Trp Ser Gly Gly Gly Thr Ala Tyr Thr Ala Ala Phe
     50                  55                  60

Ile Ser Arg Leu Asn Ile Tyr Lys Asp Asn Ser Lys Asn Gln Val Phe
 65                  70                  75                  80

Phe Glu Met Asn Ser Leu Gln Ala Asp Asp Thr Ala Met Tyr Tyr Cys
                 85                  90                  95

Ala Arg Arg Gly Ser Tyr Pro Tyr Asn Tyr Phe Asp Val Trp Gly Gln
            100                 105                 110

Gly Thr Thr Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Ala Glu Pro Lys Ser Cys Asp
    210                 215                 220

Lys Ser Arg
225
```

<210> SEQ ID NO 37
<211> LENGTH: 227
<212> TYPE: PRT
<213> ORGANISM: Artificial Sequence
<220> FEATURE:
<223> OTHER INFORMATION: Description of Artificial Sequence:N87D G53C
cloned mutant chimeric murine 2D12.5 heavy chain
variable region (VH) fused to human anti-tetanus
toxin antibody CH1 heavy chain constant region
(TTCH)

<400> SEQUENCE: 37

```
Arg Ser Val Lys Leu Gln Glu Ser Gly Pro Gly Leu Val Gln Pro Ser
  1               5                  10                  15

Gln Ser Leu Ser Ile Thr Cys Thr Val Ser Gly Phe Ser Leu Thr Asp
             20                  25                  30

Tyr Gly Val His Trp Val Arg Gln Ser Pro Gly Lys Gly Leu Glu Trp
         35                  40                  45
```

-continued

```
Leu Gly Val Ile Trp Ser Cys Gly Gly Thr Ala Tyr Thr Ala Ala Phe
     50                  55                  60

Ile Ser Arg Leu Asn Ile Tyr Lys Asp Asn Ser Lys Asn Gln Val Phe
 65                  70                  75                  80

Phe Glu Met Asn Ser Leu Gln Ala Asp Asp Thr Ala Met Tyr Tyr Cys
                 85                  90                  95

Ala Arg Arg Gly Ser Tyr Pro Tyr Asn Tyr Phe Asp Val Trp Gly Gln
            100                 105                 110

Gly Thr Thr Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Ala Glu Pro Lys Ser Cys Asp
    210                 215                 220

Lys Ser Arg
225


<210> SEQ ID NO 38
<211> LENGTH: 227
<212> TYPE: PRT
<213> ORGANISM: Artificial Sequence
<220> FEATURE:
<223> OTHER INFORMATION: Description of Artificial Sequence:N87D G54C
      cloned mutant chimeric murine 2D12.5 heavy chain
      variable region (VH) fused to human anti-tetanus
      toxin antibody CH1 heavy chain constant region
      (TTCH)

<400> SEQUENCE: 38

Arg Ser Val Lys Leu Gln Glu Ser Gly Pro Gly Leu Val Gln Pro Ser
  1               5                  10                  15

Gln Ser Leu Ser Ile Thr Cys Thr Val Ser Gly Phe Ser Leu Thr Asp
             20                  25                  30

Tyr Gly Val His Trp Val Arg Gln Ser Pro Gly Lys Gly Leu Glu Trp
        35                  40                  45

Leu Gly Val Ile Trp Ser Gly Cys Gly Thr Ala Tyr Thr Ala Ala Phe
     50                  55                  60

Ile Ser Arg Leu Asn Ile Tyr Lys Asp Asn Ser Lys Asn Gln Val Phe
 65                  70                  75                  80

Phe Glu Met Asn Ser Leu Gln Ala Asp Asp Thr Ala Met Tyr Tyr Cys
                 85                  90                  95

Ala Arg Arg Gly Ser Tyr Pro Tyr Asn Tyr Phe Asp Val Trp Gly Gln
            100                 105                 110

Gly Thr Thr Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

-continued

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Ala Glu Pro Lys Ser Cys Asp
    210                 215                 220

Lys Ser Arg
225
```

<210> SEQ ID NO 39
<211> LENGTH: 227
<212> TYPE: PRT
<213> ORGANISM: Artificial Sequence
<220> FEATURE:
<223> OTHER INFORMATION: Description of Artificial Sequence:N87D G55C cloned mutant chimeric murine 2D12.5 heavy chain variable region (VH) fused to human anti-tetanus toxin antibody CH1 heavy chain constant region (TTCH)

<400> SEQUENCE: 39

```
Arg Ser Val Lys Leu Gln Glu Ser Gly Pro Gly Leu Val Gln Pro Ser
  1               5                  10                  15

Gln Ser Leu Ser Ile Thr Cys Thr Val Ser Gly Phe Ser Leu Thr Asp
             20                  25                  30

Tyr Gly Val His Trp Val Arg Gln Ser Pro Gly Lys Gly Leu Glu Trp
         35                  40                  45

Leu Gly Val Ile Trp Ser Gly Gly Cys Thr Ala Tyr Thr Ala Ala Phe
     50                  55                  60

Ile Ser Arg Leu Asn Ile Tyr Lys Asp Asn Ser Lys Asn Gln Val Phe
 65                  70                  75                  80

Phe Glu Met Asn Ser Leu Gln Ala Asp Asp Thr Ala Met Tyr Tyr Cys
                 85                  90                  95

Ala Arg Arg Gly Ser Tyr Pro Tyr Asn Tyr Phe Asp Val Trp Gly Gln
            100                 105                 110

Gly Thr Thr Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Ala Glu Pro Lys Ser Cys Asp
    210                 215                 220

Lys Ser Arg
225
```

<210> SEQ ID NO 40
<211> LENGTH: 227
<212> TYPE: PRT
<213> ORGANISM: Artificial Sequence -continued
<220> FEATURE:
<223> OTHER INFORMATION: Description of Artificial Sequence:chimeric
      murine 2D12.5 heavy chain variable region (VH) fused to
      human anti-tetanus toxin antibody CH1 heavy chain
      constant region (TTCH) expected sequence

<400> SEQUENCE: 40

```
Arg Ser Val Lys Leu Gln Glu Ser Gly Pro Gly Leu Val Gln Pro Ser
  1               5                  10                  15

Gln Ser Leu Ser Ile Thr Cys Thr Val Ser Gly Phe Ser Leu Thr Asp
             20                  25                  30

Tyr Gly Val His Trp Val Arg Gln Ser Pro Gly Lys Gly Leu Glu Trp
         35                  40                  45

Leu Gly Val Ile Trp Ser Gly Gly Gly Thr Ala Tyr Thr Ala Ala Phe
     50                  55                  60

Ile Ser Arg Leu Asn Ile Tyr Lys Asp Asn Ser Lys Asn Gln Val Phe
 65                  70                  75                  80

Phe Glu Met Asn Ser Leu Gln Ala Asn Asp Thr Ala Met Tyr Tyr Cys
                 85                  90                  95

Ala Arg Arg Gly Ser Tyr Pro Tyr Asn Tyr Phe Asp Val Trp Gly Gln
            100                 105                 110

Gly Thr Thr Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Ala Glu Pro Lys Ser Cys Asp
    210                 215                 220

Lys Ser Arg
225
```

<210> SEQ ID NO 41
<211> LENGTH: 118
<212> TYPE: PRT
<213> ORGANISM: Mus musculus
<220> FEATURE:
<223> OTHER INFORMATION: native hybridoma murine 2D12.5 heavy chain
      variable region (VH)

<400> SEQUENCE: 41

```
Val Lys Leu Gln Glu Ser Gly Pro Gly Leu Val Gln Pro Ser Gln Ser
  1               5                  10                  15

Leu Ser Ile Thr Cys Thr Val Ser Gly Phe Ser Leu Thr Asp Tyr Gly
             20                  25                  30

Val His Trp Val Arg Gln Ser Pro Gly Lys Gly Leu Glu Trp Leu Gly
         35                  40                  45

Val Ile Trp Ser Gly Gly Gly Thr Ala Tyr Thr Ala Ala Phe Ile Ser
     50                  55                  60

Arg Leu Asn Ile Tyr Lys Asp Asn Ser Lys Asn Gln Val Phe Phe Glu
 65                  70                  75                  80
```

-continued

```
Met Asn Ser Leu Gln Ala Asn Asp Thr Ala Met Tyr Tyr Cys Ala Arg
                85                  90                  95

Arg Gly Ser Tyr Pro Tyr Asn Tyr Phe Asp Val Trp Gly Gln Gly Thr
            100                 105                 110

Thr Val Thr Val Ser Ser
        115
```

<210> SEQ ID NO 42
<211> LENGTH: 681
<212> TYPE: DNA
<213> ORGANISM: Artificial Sequence
<220> FEATURE:
<223> OTHER INFORMATION: Description of Artificial Sequence:native cloned chimeric murine 2D12.5 heavy chain variable region (VH) fused to human anti-tetanus toxin antibody CH1 heavy chain constant region (TTCH)

<400> SEQUENCE: 42

```
agatctgtga agctgcagga gtctggacct ggcctagtgc agccctcaca gagcctgtcc     60

atcacctgca cggtctctgg tttctcatta actgactatg gtgtacactg ggttcgccag    120

tctccaggaa agggtctgga atggctggga gtgatatgga gtggtggagg cacggcctat    180

actgcggcgt tcatatccag actgaacatc tacaaggaca attccaagaa ccaagttttc    240

tttgaaatga acagtctgca agctaatgac acagccatgt attactgtgc cagaaggggt    300

agctaccctt acaactactt cgatgtctgg ggccaaggga ccacggtcac cgtctccgca    360

gcctccacca agggcccatc ggtcttcccc ctggcaccct cctccaagag cacctctggg    420

ggcacagcgg ccctgggctg cctggtcaag gactacttcc ccgaaccggt gacggtgtct    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagaa agcagagccc    660

aaatcttgtg acaaatctag a                                              681
```

<210> SEQ ID NO 43
<211> LENGTH: 681
<212> TYPE: DNA
<213> ORGANISM: Artificial Sequence
<220> FEATURE:
<223> OTHER INFORMATION: Description of Artificial Sequence:N87D cloned mutant chimeric murine 2D12.5 heavy chain variable region (VH) fused to human anti-tetanus toxin antibody CH1 heavy chain constant region (TTCH)

<400> SEQUENCE: 43

```
agatctgtga agctgcagga gtctggacct ggcctagtgc agccctcaca gagcctgtcc     60

atcacctgca cggtctctgg tttctcatta actgactatg gtgtacactg ggttcgccag    120

tctccaggaa agggtctgga atggctggga gtgatatgga gtggtggagg cacggcctat    180

actgcggcgt tcatatccag actgaacatc tacaaggaca attccaagaa ccaagttttc    240

tttgaaatga acagtctgca agctgatgac acagccatgt attactgtgc cagaaggggt    300

agctaccctt acaactactt cgatgtctgg ggccaaggga ccacggtcac cgtctccgca    360

gcctccacca agggcccatc ggtcttcccc ctggcaccct cctccaagag cacctctggg    420

ggcacagcgg ccctgggctg cctggtcaag gactacttcc ccgaaccggt gacggtgtct    480

tggaactcag gcgccctgac cagcggcgtg cacaccttcc cggctgtcct acagtcctca    540

ggactctact ccctcagcag cgtggtgacc gtgccctcca gcagcttggg cacccagacc    600
```

-continued

```
tacatctgca acgtgaatca caagcccagc aacaccaagg tggacaagaa agcagagccc    660

aaatcttgtg acaaatctag a                                              681


<210> SEQ ID NO 44
<211> LENGTH: 681
<212> TYPE: DNA
<213> ORGANISM: Artificial Sequence
<220> FEATURE:
<223> OTHER INFORMATION: Description of Artificial Sequence:N87D G53C
      cloned mutant chimeric murine 2D12.5 heavy chain
      variable region (VH) fused to human anti-tetanus
      toxin antibody CH1 heavy chain constant region
      (TTCH)

<400> SEQUENCE: 44

agatctgtga agctgcagga gtctggacct ggcctagtgc agccctcaca gagcctgtcc     60

atcacctgca cggtctctgg tttctcatta actgactatg gtgtacactg ggttcgccag    120

tctccaggaa agggtctgga atggctggga gtgatatgga gttgtggagg cacggcctat    180

actgcggcgt tcatatccag actgaacatc tacaaggaca attccaagaa ccaagttttc    240

tttgaaatga acagtctgca agctgatgac acagccatgt attactgtgc cagaaggggt    300

agctaccctt acaactactt cgatgtctgg ggccaaggga ccacggtcac cgtctccgca    360

gcctccacca agggcccatc ggtcttcccc ctggcaccct cctccaagag cacctctggg    420

ggcacagcgg ccctgggctg cctggtcaag gactacttcc ccgaaccggt gacggtgtct    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagaa agcagagccc    660

aaatcttgtg acaaatctag a                                              681


<210> SEQ ID NO 45
<211> LENGTH: 681
<212> TYPE: DNA
<213> ORGANISM: Artificial Sequence
<220> FEATURE:
<223> OTHER INFORMATION: Description of Artificial Sequence:N87D G54C
      cloned mutant chimeric murine 2D12.5 heavy chain
      variable region (VH) fused to human anti-tetanus
      toxin antibody CH1 heavy chain constant region
      (TTCH)

<400> SEQUENCE: 45

agatctgtga agctgcagga gtctgggcct ggcctagtgc agccctcaca gagcctgtcc     60

atcacctgca cggtctctgg tttctcatta actgactatg gtgtacactg ggttcgccag    120

tctccaggaa agggtctgga atggctggga gtgatatgga gtggttgtgg cacggcctat    180

actgcggcgt tcatatccag actgaacatc tacaaggaca attccaagaa ccaagttttc    240

tttgaaatga acagtctgca agctgatgac acagccatgt attactgtgc cagaaggggt    300

agctaccctt acaactactt cgatgtctgg ggccaaggga ccacggtcac cgtctccgca    360

gcctccacca agggcccatc ggtcttcccc ctggcaccct cctccaagag cacctctggg    420

ggcacagcgg ccctgggctg cctggtcaag gactacttcc ccgaaccggt gacggtgtct    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagaa agcagagccc    660

aaatcttgtg acaaatctag a                                              681
```

-continued

<210> SEQ ID NO 46
<211> LENGTH: 681
<212> TYPE: DNA
<213> ORGANISM: Artificial Sequence
<220> FEATURE:
<223> OTHER INFORMATION: Description of Artificial Sequence:N87D G55C
cloned mutant chimeric murine 2D12.5 heavy chain
variable region (VH) fused to human anti-tetanus
toxin antibody CH1 heavy chain constant region
(TTCH)

<400> SEQUENCE: 46
agatctgtga agctgcagga gtctggacct ggcctagtgc agccctcaca gagcctgtcc 60
atcacctgca cggtctctgg tttctcatta actgactatg gtgtacactg ggttcgccag 120
tctccaggaa agggtctgga atggctggga gtgatatgga gtggtggatg cacggcctat 180
actgcggcgt tcatatccag actgaacatc tacaaggaca attccaagaa ccaagttttc 240
tttgaaatga acagtctgca agctgatgac acagccatgt attactgtgc cagaaggggt 300
agctaccctt acaactactt cgatgtctgg ggccaaggga ccacggtcac cgtctccgca 360
gcctccacca agggcccatc ggtcttcccc ctggcaccct cctccaagag cacctctggg 420
ggcacagcgg ccctgggctg cctggtcaag gactacttcc ccgaaccggt gacggtgtct 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agcagagccc 660
aaatcttgtg acaaatctag a 681

<210> SEQ ID NO 47
<211> LENGTH: 681
<212> TYPE: DNA
<213> ORGANISM: Artificial Sequence
<220> FEATURE:
<223> OTHER INFORMATION: Description of Artificial Sequence:chimeric
murine 2D12.5 heavy chain variable region (VH) fused to
human anti-tetanus toxin antibody CH1 heavy chain
constant region (TTCH) expected sequence

<400> SEQUENCE: 47
agatctgtga agctgcagga gtctggacct ggcctagtgc agccctcaca gagcctgtcc 60
atcacctgca cggtctctgg tttctcatta actgactatg gtgtacactg ggttcgccag 120
tctccaggaa agggtctgga atggctggga gtgatatgga gtggtggagg cacggcctat 180
actgcggcgt tcatatccag actgaacatc tacaaggaca attccaagaa ccaagttttc 240
tttgaaatga acagtctgca agctaatgac acagccatgt attactgtgc cagaaggggt 300
agctaccctt acaactactt cgatgtctgg ggccaaggga ccacggtcac cgtctccgca 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agcagagccc 660
aaatcttgtg acaaatctag a 681

<210> SEQ ID NO 48
<211> LENGTH: 354
<212> TYPE: DNA
<213> ORGANISM: Mus musculus -continued
<220> FEATURE:
<223> OTHER INFORMATION: native hybridoma murine 2D12.5 heavy chain
variable region (VH)

<400> SEQUENCE: 48
gtgaagctgc aggagtcagg acctggccta gtgcagccct cacagagcct gtccatcacc 60
tgcacggtct ctggtttctc attaactgac tatggtgtac actgggttcg ccagtctcca 120
ggaaagggtc tggaatggct gggagtgata tggagtggtg gaggcacggc ctatactgcg 180
gcgttcatat ccagactgaa catctacaag gacaattcca agaaccaagt tttctttgaa 240
atgaacagtc tgcaagctaa tgacacagcc atgtattact gtgccagaag gggtagctac 300
ccttacaact acttcgatgt ctggggccaa gggaccacag tcaccgtctc ctca 354

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence:VH2D5' BglII
primer

<400> SEQUENCE: 49
gaagatctgt gaagctgcag gagtctggac c 31

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence:CHTT2DMi
primer

<400> SEQUENCE: 50
ccacggtcac cgtctccgca gcctccacca agggc 35

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence:VH2DTTMi
primer

<400> SEQUENCE: 51
gcccttggtg gaggctgcgg agacggtgac cgtgg 35

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence:TTCH3' Xba
primer

<400> SEQUENCE: 52
cgatctagat ttgtcacaag atttgggctc tgc 33

<210> SEQ ID NO 53
<211> LENGTH: 140
<212> TYPE: DNA
<213> ORGANISM: Artificial Sequence
<220> FEATURE:
<223> OTHER INFORMATION: Description of Artificial Sequence:heavy chain
chimeric construct PCR reaction MT-VENT -continued <220> FEATURE:
<221> NAME/KEY: CDS
<222> LOCATION: (81)..(134)
<223> OTHER INFORMATION: BiP signal sequence

<400> SEQUENCE: 53

```
gccaatgtgc atcagttgtg gtcagcagca aaatcaagtg aatcatctca gtgcaactaa      60

aggggggatc cgatctcaat atg aag tta tgc ata tta ctg gcc gtc gtc gcc    113
                      Met Lys Leu Cys Ile Leu Leu Ala Val Val Ala
                        1               5                  10

ttt gtt ggc ctc tcg ctc ggg agatct                                   140
Phe Val Gly Leu Ser Leu Gly
             15
```

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence:BiP signal sequence

<400> SEQUENCE: 54

```
Met Lys Leu Cys Ile Leu Leu Ala Val Val Ala Phe Val Gly Leu Ser
  1               5                  10                  15

Leu Gly
```

<210> SEQ ID NO 55
<211> LENGTH: 140
<212> TYPE: DNA
<213> ORGANISM: Artificial Sequence
<220> FEATURE:
<223> OTHER INFORMATION: Description of Artificial Sequence:heavy chain chimeric construct PCR reaction MT-VENT
<220> FEATURE:
<221> NAME/KEY: CDS
<222> LOCATION: (19)..(90)
<223> OTHER INFORMATION: V5 epitope and polyhistidine region

<400> SEQUENCE: 55

```
tctagagggc ccttcgaa ggt aag cct atc cct aac cct ctc ctc ggt ctc       51
                    Gly Lys Pro Ile Pro Asn Pro Leu Leu Gly Leu
                      1               5                  10

gat tct acg cgt acc ggt cat cat cac cat cac cat tga gtttaaaccc       100
Asp Ser Thr Arg Thr Gly His His His His His His
             15                  20

gctgatcagc ctcgactgtg ccttctaagg cctgagctcg                          140
```

<210> SEQ ID NO 56
<211> LENGTH: 23
<212> TYPE: PRT
<213> ORGANISM: Artificial Sequence
<220> FEATURE:
<223> OTHER INFORMATION: Description of Artificial Sequence:V5 epitope and polyhistidine region

<400> SEQUENCE: 56

```
Gly Lys Pro Ile Pro Asn Pro Leu Leu Gly Leu Asp Ser Thr Arg Thr
  1               5                  10                  15

Gly His His His His His His
             20
```

-continued

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence:MTforward sequencing primer

<400> SEQUENCE: 57
catctcagtg caactaaa 18

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence:2dvhN87D_pMTBip primer

<400> SEQUENCE: 58
catggctgtg tcatcagctt gcagactgtt c 31

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence:G53C noncoding 2dG53c_pMT primer

<400> SEQUENCE: 59
cgtgcctcca caactccata tcac 24

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence:G54C noncoding 2dG54c_pMT primer

<400> SEQUENCE: 60
ccgtgccaca accactccat atc 23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence:G55C noncoding 2dG55c_pMT primer

<400> SEQUENCE: 61
ccgtgcatcc accactccat atc 23

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence:2dvhKBglII_pMTBip primer

<400> SEQUENCE: 62
gctcgggaga tgtgtgaagc tg 22

-continued

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence:BGHreverse
sequencing primer

<400> SEQUENCE: 63
tagaaggcac agtcgagg 18

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence:2dVL5'Bgl
primer

<400> SEQUENCE: 64
gaagatctgc tgttgtgact caggaatct 29

<210> SEQ ID NO 65
<211> LENGTH: 42
<212> TYPE: DNA
<213> ORGANISM: Artificial Sequence
<220> FEATURE:
<223> OTHER INFORMATION: Description of Artificial Sequence:2dVLMiTop
primer

<400> SEQUENCE: 65
accaaactga ctgtcctaag ccgaactgtg gctgcaccat ct 42

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence:2dVLMiBot
primer

<400> SEQUENCE: 66
agatggtgca gccacagttc ggcttaggac agtcagtttg gt 42

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence:TTCL3' Xba
primer

<400> SEQUENCE: 67
cgatctagaa ttaacactct cccctg 26

<210> SEQ ID NO 68
<211> LENGTH: 138
<212> TYPE: DNA
<213> ORGANISM: Artificial Sequence
<220> FEATURE:
<223> OTHER INFORMATION: Description of Artificial Sequence:light chain
chimeric construct PCR reaction MT-VENT
<220> FEATURE:
<221> NAME/KEY: CDS
<222> LOCATION: (17)..(88)
<223> OTHER INFORMATION: V5 epitope and polyhistidine region -continued

```
<400> SEQUENCE: 68

tagagggccc ttcgaaggta agcctatccc taaccctctc ctcggtctcg attctacgcg     60

taccggtcat catcaccatc accattgagt ttaaacccgc tgatcagcct cgactgtgcc    120

ttctaaggcc tgagctcg                                                  138


<210> SEQ ID NO 69
<211> LENGTH: 25
<212> TYPE: DNA
<213> ORGANISM: Artificial Sequence
<220> FEATURE:
<223> OTHER INFORMATION: Description of Artificial
      Sequence:2dvL_S48G_pMTBip primer

<400> SEQUENCE: 69

cacctattag accagtgaat aaatg                                           25


<210> SEQ ID NO 70
<211> LENGTH: 38
<212> TYPE: DNA
<213> ORGANISM: Artificial Sequence
<220> FEATURE:
<223> OTHER INFORMATION: Description of Artificial
      Sequence:S48G_N53C_pMTBip primer

<400> SEQUENCE: 70

cggttattac aaccacctat tagaccagtg aataaatg                             38


<210> SEQ ID NO 71
<211> LENGTH: 22
<212> TYPE: DNA
<213> ORGANISM: Artificial Sequence
<220> FEATURE:
<223> OTHER INFORMATION: Description of Artificial
      Sequence:2dvLKBglII_pMTBip primer

<400> SEQUENCE: 71

gctcgggaga tgtgctgttg tg                                              22


<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence:flexible
      linker

<400> SEQUENCE: 72

Gly Gly Gly Ser Gly Gly Gly Ser Gly Gly Gly Ser
  1               5                  10
```